US010982212B2

(12) United States Patent
Pachuk et al.

(10) Patent No.: US 10,982,212 B2
(45) Date of Patent: Apr. 20, 2021

(54) CONSERVED HBV AND HCV SEQUENCES USEFUL FOR GENE SILENCING

(71) Applicant: ALNYLAM PHARMACEUTICALS, INC., Cambridge, MA (US)

(72) Inventors: Catherine J Pachuk, Cambridge, MA (US); Chandrasekhar Satishchandran, Cambridge, MA (US); Vincent R. Zurawski, Cambridge, MA (US); Liat Mintz, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/965,309

(22) Filed: Apr. 27, 2018

(65) Prior Publication Data

US 2019/0100757 A1 Apr. 4, 2019

Related U.S. Application Data

(63) Continuation of application No. 14/921,510, filed on Oct. 23, 2015, now Pat. No. 9,982,263, which is a continuation of application No. 14/043,272, filed on Oct. 1, 2013, now Pat. No. 9,200,281, which is a continuation of application No. 13/065,601, filed on Dec. 12, 2005, now Pat. No. 8,575,327, which is a continuation-in-part of application No. PCT/US2004/019229, filed on Jun. 10, 2004.

(60) Provisional application No. 60/478,076, filed on Jun. 12, 2003, provisional application No. 60/638,294, filed on Dec. 22, 2004.

(51) Int. Cl.
*C12N 15/113* (2010.01)
*A61K 31/713* (2006.01)

(52) U.S. Cl.
CPC ........ *C12N 15/1131* (2013.01); *A61K 31/713* (2013.01); *C12N 2310/14* (2013.01); *C12N 2310/531* (2013.01); *C12N 2320/30* (2013.01); *C12N 2320/32* (2013.01); *C12N 2730/10122* (2013.01); *C12N 2770/24222* (2013.01)

(58) Field of Classification Search
CPC ....... A61K 31/713; A61K 38/00; A61P 31/20; C12N 15/1131; C12N 2310/14; C12N 2320/30
USPC .... 435/6.1, 91.1, 91.31, 455, 458; 536/23.1, 536/24.5
See application file for complete search history.

(56) References Cited

U.S. PATENT DOCUMENTS

| | | | |
|---|---|---|---|
| 5,571,026 A | 11/1996 | Kahre | |
| 5,604,118 A | 2/1997 | Giri et al. | |
| 5,610,050 A | 3/1997 | Blum et al. | |
| 5,629,153 A | 5/1997 | Urdea | |
| 5,843,770 A | 12/1998 | Ill et al. | |
| 5,981,274 A | 11/1999 | Tyrrell et al. | |
| 5,998,203 A | 12/1999 | Matulic-Adamic et al. | |
| 6,001,990 A | 12/1999 | Wands et al. | |
| 6,057,153 A | 5/2000 | George et al. | |
| 6,287,770 B1 | 9/2001 | Weston et al. | |
| 6,503,533 B1 | 1/2003 | Korba et al. | |
| 6,518,417 B1 | 2/2003 | Sczakiel et al. | |
| 6,558,954 B1 | 5/2003 | Takle et al. | |
| 6,573,048 B1 | 6/2003 | VanAtta et al. | |
| 7,829,691 B2 | 11/2010 | Anthony et al. | |
| 7,985,581 B2 | 7/2011 | Pachuk et al. | |
| 8,450,467 B2 | 5/2013 | Manoharan et al. | |
| 8,575,327 B2 | 11/2013 | Pachuk et al. | |
| 8,598,334 B2 | 12/2013 | Hamatake | |
| 8,618,277 B2 | 12/2013 | Beigelman et al. | |
| 9,034,841 B2 | 5/2015 | Swayze et al. | |
| 9,982,263 B2 * | 5/2018 | Pachuk | A61P 31/20 |
| 10,407,682 B2 | 9/2019 | Bartz et al. | |
| 10,513,703 B2 | 12/2019 | Hinkle et al. | |
| 10,662,428 B2 | 5/2020 | Beigelman et al. | |
| 10,793,860 B2 | 10/2020 | Bartz et al. | |
| 2002/0086356 A1 | 7/2002 | Tuschl et al. | |
| 2002/0155124 A1 | 10/2002 | Sallberg et al. | |
| 2003/0083294 A1 | 5/2003 | Sullenger et al. | |
| 2003/0087855 A1 | 5/2003 | Ward et al. | |
| 2003/0143732 A1 | 7/2003 | Fosnaugh et al. | |
| 2003/0190659 A1 | 10/2003 | LaCasse et al. | |
| 2004/0180351 A1 | 9/2004 | Giese et al. | |
| 2004/0259247 A1 | 12/2004 | Tuschl et al. | |
| 2005/0020521 A1 | 1/2005 | Rana | |
| 2005/0080246 A1 | 4/2005 | Allerson et al. | |
| 2007/0031844 A1 | 2/2007 | Khvorova et al. | |

(Continued)

FOREIGN PATENT DOCUMENTS

| | | | | |
|---|---|---|---|---|
| CN | 1566131 * | 1/2005 | C12N 15/1131 | |
| DE | 197 25 803 C1 | 2/1999 | | |

(Continued)

OTHER PUBLICATIONS

Andino, "RNAi puts a lid on virus replication," *Nature Biotechnology 21*(6):629-630, 2003.

(Continued)

*Primary Examiner* — Jane J Zara
(74) *Attorney, Agent, or Firm* — Seed Intellectual Property Law Group LLP

(57) ABSTRACT

Conserved consensus sequences from known hepatitis B virus strains and known hepatitis C virus strains, which are useful in inhibiting the expression of the viruses in mammalian cells, are provided. These sequences are useful to silence the genes of HBV and HCV, thereby providing therapeutic utility against HBV and HCV viral infection in humans.

10 Claims, 16 Drawing Sheets

Specification includes a Sequence Listing.

(56) References Cited

U.S. PATENT DOCUMENTS

| | | | | |
|---|---|---|---|---|
| 2012/0035240 | A1* | 2/2012 | Pachuk | A61P 31/20 514/44 A |
| 2019/0233821 | A1 | 8/2019 | Beigelman et al. | |
| 2020/0038506 | A1 | 2/2020 | Sepp-Lorenzino et al. | |

FOREIGN PATENT DOCUMENTS

| | | | | |
|---|---|---|---|---|
| EP | 2 071 030 | A2 | 6/2009 | |
| JP | 5-507203 | A | 10/1993 | |
| JP | 7-303485 | A | 11/1995 | |
| JP | 2002-335968 | A | 11/2002 | |
| JP | 2011-224013 | A | 11/2011 | |
| WO | 96/03152 | A1 | 2/1996 | |
| WO | 97/33991 | A1 | 9/1997 | |
| WO | 98/58055 | A2 | 12/1998 | |
| WO | 99/13886 | A1 | 3/1999 | |
| WO | 01/40279 | A2 | 6/2001 | |
| WO | 01/75164 | A2 | 10/2001 | |
| WO | 03/006477 | A1 | 1/2003 | |
| WO | 03/070918 | A2 | 8/2003 | |
| WO | 2004/078181 | A1 | 9/2004 | |
| WO | 2005/014806 | A2 | 2/2005 | |
| WO | WO-2006069064 | A2 * | 6/2006 | C12N 15/1131 |

OTHER PUBLICATIONS

Chouteau et al., "A short N-proximal region in the large envelope protein harbors a Determinant That Contributes to the Species Specificity of Human Hepatitis B Virus," *Journal of Virology 75*(23):11565-11572, 2001.

Couzin, "Mini RNA Molecules Shield Mouse Liver From Hepatitis," *Science 299*:995, 2003. (2 pages).

European Search Report, dated Jan. 14, 2008, for European Application No. 04776661.3-1212, 2 pages.

Feitelson et al., "New Animal Models of Hepatitis B and C," *ILAR Journal 42*(2):127-138, 2001.

Giladi et al., "Small Interfering RNA Inhibits Hepatitis B Virus Replication in Mice," *Mol. Ther. 8*(5):769-776, 2003.

Hamasaki et al., "Short interfering RNA-directed inhibition of hepatitis B virus replication," *FEBS Letters 543*(1-3):51-54, 2003.

Holen et al., "Positional effects of short interfering RNAs targeting the human coagulation trigger Tissue Factor," *Nucleic Acids Research 30*(8):1757-1766, 2002.

Holen T. et al., "Similar behavior of single-strand and double-strand siRNSs suggests they act through a common RNAi pathway," *Nucleic Acids Research 31*(9):2401-2407, 2003.

International Preliminary Report on Patentability, dated Jan. 7, 2007, for International Application No. PCT/US2004/019229, 6 pages.

International Search Report, dated Sep. 16, 2005, for International Application No. PCT/US2004/019229, 8 pages.

Kapadia et al., "Interference of hepatitis C virus RNA replication by short interfering RNAs," *Proceedings of the National Academy of Sciences of the USA 100*(4):2014-2018, 2003.

Australian Search Report, dated Oct. 12, 2006, for Singaporean Application No. 200507781-3, 7 pages.

Australian Written Opinion, dated Oct. 12, 2006, for Singaporean Application No. 200507781-3, 6 pages.

McCaffrey et al., "Inhibition of hepatitis B virus in mice by RNA interference," *Nature Biotechnology 21*(6):639-644, 2003.

McCaffrey et al., "RNA interference in adult mice," *Nature 418*(6893):38-39, 2002.

Okamoto et al., "Full-Length Sequence of a Hepatitis C Virus Genome Having Poor Homology to Reported Isolates: Comparative Study of Four Distinct Genotypes," *Virology 188*(1):331-341, 1992.

Randall et al., "Clearance of replicating hepatitis C virus replicon RNAs in cell culture by small interfering RNAs," *PNAS 100*(1):235-240, 2003.

Seo et al., "Small Interfering RNA-Mediated Inhibition of Hepatitis C Virus Replication in the Human Hepatoma Cell Line Huh-7," *J. Virol. 77*(1):810-812, 2003.

Shlomai et al., "Inhibition of Hepatitis B Virus Expression and Replication by RNA Interference," *Hepatology 37*(4):764-770, 2003.

Sui et al., "A DNA vector-based RNAi technology to suppress gene expression in mammalian calls," *PNAS 99*(8):5515-5520, 2002.

Tuschl et al., "The siRNA user guide," Revised Aug. 26, 2001, URL=http://www.mpibpc.gwdg.de/abteilungen/100/105/sirna_u.html, download date Nov. 14, 2001, 5 pages.

Vitral et al., "The use of non-human primates as animal models for the study of hepatitis viruses," *Brazilian Journal of Medical and Biological Research 31*(8):1035-1048, 1998.

Wilson et al., "RNA interference blocks gene expression and RNA synthesis from hepatitis C replicons propagated in human liver cells," *Proceedings of the National Academy of Sciences of the USA 100*(5):2783-2788, 2003.

Amarzguioui et al., "Tolerance for mutations and chemical modifications in a siRNA" *Nucl. Acids. Res. 31*(2):589-595, 2003.

Bertrand et al., "Comparison of antisense oligonucleotides and siRNAs in cell culture and in vivo," *BBRC 296*:1000-1004, 2002.

Braasch et al., "Novel antisense and peptide Nucleic Acid Strategies for Controlling Gene Expression," *Biochem. 41*(14):4503-4510, 2002.

Caplen et al., "Specific inhibition of gene expression by small double-stranded RNAs in invertebrate and vertebrate systems," *Proc. Natl. Acad. Sci. 98*(17):9742-9747, 2001.

Elbashir et al., "Duplexes of 21-nucleotide RNAs mediate RNA interference in cultured mammalian cells," *Nature 411*:494-498, 2001.

Elbashir et al., "Functional anatomy of siRNA for mediating efficient RNAi in *Drosophila melanogaster* embryo lysate," *EMBO J. 20*(23): 6877-6888, 2001.

Freier et al., "The ups and downs of nucleic acid duplex stability: structure—stability studies on chemically-modified DNA:RNA duplexes," *Nucl. Acids Res. 25*(22):4429-4443, 1997.

Olie et al., "Analysis of ribosyl-modified, mixed backbone analogs of a bcl-2/bcl-xL antisense oligonucleotide," *Biochim. Biophys. Acta 1576*(1-2):101-109, 2002.

Parrish et al., "Functional Anatomy of a dsRNA Trigger: Differential Requirement for the Two Trigger Strands in RNA interference," *Mol. Cell 6*:1077-1087, 2000.

Putlitz et al., "Antisense RNA Complementary to Hepatitis B Virus Specifically Inhibits Viral Replication," *Gastroenterology 115*:702-713, 1998.

Tuschl et al., "The siRNA user guide," Revised May 6, 2004, URL=http://diyhpl.us/~bryan/irc/protocol-online/protocol-cache/sirna.html, download date Oct. 10, 2018, 7 pages.

McCafferey et al., "Inhibition of hepatitis B virus in mice by RNA interference," *Nature Biotechnology 21*(6):639-644, 2003 (Supplemental Online Data (1)), retrieved from the Internet: https://media.nature.com/original/nature-assets/nbt/journal/v21/n6/extref/nbt824-S1.pdf (1 page).

McCafferey et al., "Inhibition of hepatitis B virus in mice by RNA interference," *Nature Biotechnology 21*(6):639-644, 2003 (Supplemental Online Data (2)), retrieved from the Internet: https ://media.nature.com/original/nature-assets/nbt/journal/v21/n6/extref/nbt824-S2.pdf (2 pages).

* cited by examiner

EFFECTIVE HBV-AYW shRNA INSERTS

5' – GGTCGAC – sense stem – loop – antisense stem –TT – 3'

FIG. 15

| Position | sequence | length |
|---|---|---|
| 9510-9531 | TGGCTCCATCTTAGCCCTAGTC | 22 |
| 9510-9533 | TGGCTCCATCTTAGCCCTAGTCAC | 24 |
| 9510-9534 | TGGCTCCATCTTAGCCCTAGTCACG | 25 |
| 9510-9535 | TGGCTCCATCTTAGCCCTAGTCACGG | 26 |
| 9510-9536 | TGGCTCCATCTTAGCCCTAGTCACGGC | 27 |
| 9514-9534 | TCCATCTTAGCCCTAGTCACG | 21 |
| 9514-9535 | TCCATCTTAGCCCTAGTCACGG | 22 |
| 9514-9536 | TCCATCTTAGCCCTAGTCACGGC | 23 |
| 9514-9539 | TCCATCTTAGCCCTAGTCACGGCTAG | 26 |
| 9514-9540 | TCCATCTTAGCCCTAGTCACGGCTAGC | 27 |
| 9514-9542 | TCCATCTTAGCCCTAGTCACGGCTAGCTG | 29 |
| 9517-9539 | ATCTTAGCCCTAGTCACGGCTAG | 23 |
| 9517-9540 | ATCTTAGCCCTAGTCACGGCTAGC | 24 |
| 9517-9542 | ATCTTAGCCCTAGTCACGGCTAGCTG | 26 |
| 9517-9544 | ATCTTAGCCCTAGTCACGGCTAGCTGTG | 28 |
| 9518-9539 | TCTTAGCCCTAGTCACGGCTAG | 22 |
| 9518-9540 | TCTTAGCCCTAGTCACGGCTAGC | 23 |
| 9518-9542 | TCTTAGCCCTAGTCACGGCTAGCTG | 25 |
| 9518-9544 | TCTTAGCCCTAGTCACGGCTAGCTGTG | 27 |
| 9520-9540 | TTAGCCCTAGTCACGGCTAGC | 21 |
| 9520-9542 | TTAGCCCTAGTCACGGCTAGCTG | 23 |
| 9520-9544 | TTAGCCCTAGTCACGGCTAGCTGTG | 25 |
| 9520-9548 | TTAGCCCTAGTCACGGCTAGCTGTGAAAG | 29 |
| 9521-9542 | TAGCCCTAGTCACGGCTAGCTG | 22 |
| 9521-9544 | TAGCCCTAGTCACGGCTAGCTGTG | 24 |
| 9521-9548 | TAGCCCTAGTCACGGCTAGCTGTGAAAG | 28 |
| 9521-9549 | TAGCCCTAGTCACGGCTAGCTGTGAAAGG | 29 |
| 9522-9542 | AGCCCTAGTCACGGCTAGCTG | 21 |
| 9522-9544 | AGCCCTAGTCACGGCTAGCTGTG | 23 |
| 9522-9548 | AGCCCTAGTCACGGCTAGCTGTGAAAG | 27 |
| 9522-9549 | AGCCCTAGTCACGGCTAGCTGTGAAAGG | 28 |
| 9527-9548 | TAGTCACGGCTAGCTGTGAAAG | 22 |
| 9527-9549 | TAGTCACGGCTAGCTGTGAAAGG | 23 |
| 9527-9551 | TAGTCACGGCTAGCTGTGAAAGGTC | 25 |
| 9527-9552 | TAGTCACGGCTAGCTGTGAAAGGTCC | 26 |
| 9527-9553 | TAGTCACGGCTAGCTGTGAAAGGTCCG | 27 |
| 9527-9555 | TAGTCACGGCTAGCTGTGAAAGGTCCGTG | 29 |
| 9528-9548 | AGTCACGGCTAGCTGTGAAAG | 21 |
| 9528-9549 | AGTCACGGCTAGCTGTGAAAGG | 22 |
| 9528-9551 | AGTCACGGCTAGCTGTGAAAGGTC | 24 |
| 9528-9552 | AGTCACGGCTAGCTGTGAAAGGTCC | 25 |
| 9528-9553 | AGTCACGGCTAGCTGTGAAAGGTCCG | 26 |
| 9528-9555 | AGTCACGGCTAGCTGTGAAAGGTCCGTG | 28 |
| 9530-9551 | TCACGGCTAGCTGTGAAAGGTC | 22 |
| 9530-9552 | TCACGGCTAGCTGTGAAAGGTCC | 23 |
| 9530-9553 | TCACGGCTAGCTGTGAAAGGTCCG | 24 |
| 9530-9555 | TCACGGCTAGCTGTGAAAGGTCCGTG | 26 |
| 9530-9557 | TCACGGCTAGCTGTGAAAGGTCCGTGAG | 28 |
| 9530-9558 | TCACGGCTAGCTGTGAAAGGTCCGTGAGC | 29 |
| 9532-9552 | ACGGCTAGCTGTGAAAGGTCC | 21 |
| 9532-9553 | ACGGCTAGCTGTGAAAGGTCCG | 22 |
| 9532-9555 | ACGGCTAGCTGTGAAAGGTCCGTG | 24 |
| 9532-9557 | ACGGCTAGCTGTGAAAGGTCCGTGAG | 26 |
| 9532-9558 | ACGGCTAGCTGTGAAAGGTCCGTGAGC | 27 |
| 9532-9559 | ACGGCTAGCTGTGAAAGGTCCGTGAGCC | 28 |
| 9532-9560 | ACGGCTAGCTGTGAAAGGTCCGTGAGCCG | 29 |
| 9537-9557 | TAGCTGTGAAAGGTCCGTGAG | 21 |
| 9537-9558 | TAGCTGTGAAAGGTCCGTGAGC | 22 |
| 9537-9559 | TAGCTGTGAAAGGTCCGTGAGCC | 23 |

FIG. 15 continued

| | | |
|---|---|---|
| 9537-9560 | TAGCTGTGAAAGGTCCGTGAGCCG | 24 |
| 9537-9561 | TAGCTGTGAAAGGTCCGTGAGCCGC | 25 |
| 9537-9564 | TAGCTGTGAAAGGTCCGTGAGCCGCTTG | 28 |
| 9538-9558 | AGCTGTGAAAGGTCCGTGAGC | 21 |
| 9538-9559 | AGCTGTGAAAGGTCCGTGAGCC | 22 |
| 9538-9560 | AGCTGTGAAAGGTCCGTGAGCCG | 23 |
| 9538-9561 | AGCTGTGAAAGGTCCGTGAGCCGC | 24 |
| 9538-9564 | AGCTGTGAAAGGTCCGTGAGCCGCTTG | 27 |
| 9538-9566 | AGCTGTGAAAGGTCCGTGAGCCGCTTGAC | 29 |
| 9541-9561 | TGTGAAAGGTCCGTGAGCCGC | 21 |
| 9541-9564 | TGTGAAAGGTCCGTGAGCCGCTTG | 24 |
| 9541-9566 | TGTGAAAGGTCCGTGAGCCGCTTGAC | 26 |
| 9541-9568 | TGTGAAAGGTCCGTGAGCCGCTTGACTG | 28 |
| 9541-9569 | TGTGAAAGGTCCGTGAGCCGCTTGACTGC | 29 |
| 9543-9564 | TGAAAGGTCCGTGAGCCGCTTG | 22 |
| 9543-9566 | TGAAAGGTCCGTGAGCCGCTTGAC | 24 |
| 9543-9568 | TGAAAGGTCCGTGAGCCGCTTGACTG | 26 |
| 9543-9569 | TGAAAGGTCCGTGAGCCGCTTGACTGC | 27 |
| 9543-9571 | TGAAAGGTCCGTGAGCCGCTTGACTGCAG | 29 |
| 9545-9566 | AAAGGTCCGTGAGCCGCTTGAC | 22 |
| 9545-9568 | AAAGGTCCGTGAGCCGCTTGACTG | 24 |
| 9545-9569 | AAAGGTCCGTGAGCCGCTTGACTGC | 25 |
| 9545-9571 | AAAGGTCCGTGAGCCGCTTGACTGCAG | 27 |
| 9545-9573 | AAAGGTCCGTGAGCCGCTTGACTGCAGAG | 29 |
| 9546-9564 | AAGGTCCGTGAGCCGCTTGAC | 21 |
| 9546-9566 | AAGGTCCGTGAGCCGCTTGACTG | 23 |
| 9546-9569 | AAGGTCCGTGAGCCGCTTGACTGC | 24 |
| 9546-9571 | AAGGTCCGTGAGCCGCTTGACTGCAG | 26 |
| 9546-9573 | AAGGTCCGTGAGCCGCTTGACTGCAGAG | 28 |
| 9547-9568 | AGGTCCGTGAGCCGCTTGACTG | 22 |
| 9547-9569 | AGGTCCGTGAGCCGCTTGACTGC | 23 |
| 9547-9571 | AGGTCCGTGAGCCGCTTGACTGCAG | 25 |
| 9547-9573 | AGGTCCGTGAGCCGCTTGACTGCAGAG | 27 |
| 9547-9575 | AGGTCCGTGAGCCGCTTGACTGCAGAGAG | 29 |
| 9550-9571 | TCCGTGAGCCGCTTGACTGCAG | 22 |
| 9550-9573 | TCCGTGAGCCGCTTGACTGCAGAG | 24 |
| 9550-9575 | TCCGTGAGCCGCTTGACTGCAGAGAG | 26 |
| 9550-9577 | TCCGTGAGCCGCTTGACTGCAGAGAGTG | 28 |
| 9550-9578 | TCCGTGAGCCGCTTGACTGCAGAGAGTGC | 29 |
| 9554-9575 | TGAGCCGCTTGACTGCAGAGAG | 22 |
| 9554-9577 | TGAGCCGCTTGACTGCAGAGAGTG | 24 |
| 9554-9578 | TGAGCCGCTTGACTGCAGAGAGTGC | 25 |
| 9554-9580 | TGAGCCGCTTGACTGCAGAGAGTGCTG | 27 |
| 9556-9577 | AGCCGCTTGACTGCAGAGAGTG | 22 |
| 9556-9578 | AGCCGCTTGACTGCAGAGAGTGC | 23 |
| 9556-9580 | AGCCGCTTGACTGCAGAGAGTGCTG | 25 |
| 9556-9584 | AGCCGCTTGACTGCAGAGAGTGCTGATAC | 29 |
| 9562-9584 | TTGACTGCAGAGAGTGCTGATAC | 23 |
| 9562-9586 | TTGACTGCAGAGAGTGCTGATACTG | 25 |
| 9562-9587 | TTGACTGCAGAGAGTGCTGATACTGG | 26 |
| 9562-9588 | TTGACTGCAGAGAGTGCTGATACTGGC | 27 |
| 9562-9589 | TTGACTGCAGAGAGTGCTGATACTGGCC | 28 |
| 9563-9584 | TGACTGCAGAGAGTGCTGATAC | 22 |
| 9563-9586 | TGACTGCAGAGAGTGCTGATACTG | 24 |
| 9563-9587 | TGACTGCAGAGAGTGCTGATACTGG | 25 |
| 9563-9588 | TGACTGCAGAGAGTGCTGATACTGGC | 26 |
| 9563-9589 | TGACTGCAGAGAGTGCTGATACTGGCC | 27 |
| 9563-9591 | TGACTGCAGAGAGTGCTGATACTGGCCTC | 29 |
| 9565-9586 | ACTGCAGAGAGTGCTGATACTG | 22 |
| 9565-9587 | ACTGCAGAGAGTGCTGATACTGG | 23 |

FIG. 15 continued

| | | |
|---|---|---|
| 9565-9588 | ACTGCAGAGAGTGCTGATACTGGC | 24 |
| 9565-9589 | ACTGCAGAGAGTGCTGATACTGGCC | 25 |
| 9565-9591 | ACTGCAGAGAGTGCTGATACTGGCCTC | 27 |
| 9565-9593 | ACTGCAGAGAGTGCTGATACTGGCCTCTC | 29 |
| 9567-9587 | TGCAGAGAGTGCTGATACTGG | 21 |
| 9567-9588 | TGCAGAGAGTGCTGATACTGGC | 22 |
| 9567-9589 | TGCAGAGAGTGCTGATACTGGCC | 23 |
| 9567-9591 | TGCAGAGAGTGCTGATACTGGCCTC | 25 |
| 9567-9593 | TGCAGAGAGTGCTGATACTGGCCTCTC | 27 |
| 9567-9595 | TGCAGAGAGTGCTGATACTGGCCTCTCTG | 29 |
| 9570-9591 | AGAGAGTGCTGATACTGGCCTC | 22 |
| 9570-9593 | AGAGAGTGCTGATACTGGCCTCTC | 24 |
| 9570-9595 | AGAGAGTGCTGATACTGGCCTCTCTG | 26 |
| 9570-9596 | AGAGAGTGCTGATACTGGCCTCTCTGC | 27 |
| 9570-9598 | AGAGAGTGCTGATACTGGCCTCTCTGCAG | 29 |
| 9572-9593 | AGAGTGCTGATACTGGCCTCTC | 22 |
| 9572-9595 | AGAGTGCTGATACTGGCCTCTCTG | 24 |
| 9572-9596 | AGAGTGCTGATACTGGCCTCTCTGC | 25 |
| 9572-9598 | AGAGTGCTGATACTGGCCTCTCTGCAG | 27 |
| 9574-9595 | AGTGCTGATACTGGCCTCTCTG | 22 |
| 9574-9596 | AGTGCTGATACTGGCCTCTCTGC | 23 |
| 9574-9598 | AGTGCTGATACTGGCCTCTCTGCAG | 25 |
| 9574-9601 | AGTGCTGATACTGGCCTCTCTGCAGATC | 28 |
| 9576-9596 | TGCTGATACTGGCCTCTCTGC | 21 |
| 9576-9598 | TGCTGATACTGGCCTCTCTGCAG | 23 |
| 9576-9601 | TGCTGATACTGGCCTCTCTGCAGATC | 26 |
| 9576-9604 | TGCTGATACTGGCCTCTCTGCAGATCAAG | 29 |
| 9579-9601 | TGATACTGGCCTCTCTGCAGATC | 23 |
| 9579-9604 | TGATACTGGCCTCTCTGCAGATCAAG | 26 |
| 9581-9601 | ATACTGGCCTCTCTGCAGATC | 21 |
| 9581-9604 | ATACTGGCCTCTCTGCAGATCAAG | 24 |
| 9583-9604 | ACTGGCCTCTCTGCAGATCAAG | 22 |

CONSERVED HBV AND HCV SEQUENCES USEFUL FOR GENE SILENCING

CROSS-REFERENCE TO RELATED APPLICATIONS

This application is a continuation under 35 USC § 120 of U.S. patent application Ser. No. 14/921,510 filed Oct. 23, 2015, which is a continuation under 35 USC § 120 of U.S. patent application Ser. No. 14/043,272 filed Oct. 1, 2013, now U.S. Pat. No. 9,200,281, issued on Dec. 1, 2015, which continuation under 35 USC § 120 of U.S. patent application Ser. No. 13/065,601 filed Dec. 12, 2005, now U.S. Pat. No. 8,575,327, issued on Nov. 5, 2013, which is a continuation-in-part under 35 USC § 120 of International Application PCT/US2004/019229 filed Jun. 10, 2004, which claims benefit under 35 U.S.C. § 119(e) of U.S. Provisional Application 60/478,076 filed Jun. 12, 2003, the contents of each of which are incorporated herein by reference in their entireties. U.S. patent application Ser. No. 13/065,601 also claims benefit under 35 U.S.C. § 119(e) of U.S. Provisional Application No. 60/638,294, filed Dec. 22, 2004, which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Apr. 27, 2018, is named 051058-034400-C3_SL.txt and is 63,829 bytes in size.

FIELD OF THE INVENTION

This invention relates to methods and compositions utilizing conserved genetic sequences of known hepatitis B viral (HBV) strains and known hepatitis C viral (HCV) strains to modulate the expression of HBV and/or HCV in mammalian cells, via double-stranded RNA-mediated gene silencing, including post-transcriptional gene silencing (PTGS) and transcriptional gene silencing (TGS).

BACKGROUND OF THE INVENTION

Human hepatitis C (HCV) is a major public health problem with an estimated 200 million persons worldwide infected. The number of new infections per year in the United States is estimated to be about 25,000 in 2001. This number has declined from an estimated 240,000 new cases per year in the 1980's due to blood donor screening. Nevertheless, an estimated 3.9 million (1.8%) Americans have been infected with HCV, of whom 2.7 million are chronically infected. Hepatitis C shows significant genetic variation in worldwide populations, evidence of its frequent rates of mutation and rapid evolution. There are six basic genotypes of HCV, with 15 recorded subtypes, which vary in prevalence across different regions of the world. Each of these major genotypes may differ significantly in their biological effects—in terms of replication, mutation rates, type and severity of liver damage, and detection and treatment options—however, these differences are not yet clearly understood.

There is currently no vaccine against HCV and available drug therapy, including ribavirin and interferon, is only partially effective. It is estimated that 75-85% of infected persons will develop a chronic infection, with 70% of chronically infected persons expected to develop chronic liver 5 disease including hepatocellular carcinoma. Chronic HCV related liver disease is a leading indication for liver transplant.

Although a human hepatitis B vaccine has been available since 1982, it is estimated that 350 million persons worldwide are chronically infected with HBV. While the number of new infections per year in the United States has declined from an average of 260,000 in the 1980s to about 78,000 in 2001, there are an estimated 1.25 million hepatitis B carriers, defined as persons positive for hepatitis B surface antigen (HBsAg) for more than 6 months. Such carriers of HBV are at increased risk for developing cirrhosis, hepatic decompensation, and hepatocellular carcinoma. Although most carriers do not develop hepatic complications from chronic hepatitis B, 15% to 40% will develop serious sequelae during their lifetime, and death from chronic liver disease occurs in 15-25% of chronically infected persons.

There is a need for improved therapeutic agents effective in patients suffering from HBV and/or HCV infection, especially chronic infection, which together are estimated to account for 75% of all cases of liver disease around the world. There is also an extreme need for prophylactic methods and agents effective against HCV.

Nucleic acids (e.g., DNA, RNA, hybrid, heteroduplex, and modified nucleic acids) have come to be recognized as extremely valuable agents with significant and varied biological activities, including their use as therapeutic moieties in the prevention and/or treatment of disease states in man and animals. For example, oligonucleotides acting through antisense mechanisms are designed to hybridize to target mRNAs, thereby modulating the activity of the mRNA. Another approach to the utilization of nucleic acids as therapeutics is designed to take advantage of triplex or triple strand formation, in which a single-stranded oligomer (e.g., DNA or RNA) is designed to bind to a double-stranded DNA target to produce a desired result, e.g., inhibition of transcription from the DNA target. Yet another approach to the utilization of nucleic acids as therapeutics is designed to take advantage of ribozymes, in which a structured RNA or a modified oligomer is designed to bind to an RNA or a double-stranded DNA target to produce a desired result, e.g., targeted cleavage of RNA or the DNA target and thus inhibiting its expression. Nucleic acids may also be used as immunizing agents, e.g., by introducing DNA molecules into the tissues or cells of an organism that express proteins capable of eliciting an immune response. Nucleic acids may also be engineered to encode an RNA with antisense, ribozyme, or triplex activities, or to produce RNA that is translated to produce protein(s) that have biological function.

More recently, the phenomenon of RNAi or double-stranded RNA (dsRNA)-mediated gene silencing has been recognized, whereby dsRNA complementary to a region of a target gene in a cell or organism inhibits expression of the target gene (see, e.g., WO 99/32619, published 1 Jul. 1999, Fire et al.; and U.S. Pat. No. 6,506,559: "Genetic Inhibition by Double-Stranded RNA;" WO 00/63364: "Methods and Compositions for Inhibiting the Function of Polynucleotide Sequences," Pachuk and Satishchandran; and U.S. Ser. No. 60/419,532, filed Oct. 18, 2002). dsRNA-mediated gene silencing, utilizing compositions providing an at least partially double-stranded dsRNA, is expected to provide extremely valuable therapeutic and/or prophylactic agents against viral infection, including HBV and/or HCV, including in the extremely difficult problem of chronic HBV and/or HCV infection.

SUMMARY OF THE INVENTION

A method for inhibiting expression of a polynucleotide sequence of hepatitis B virus in an in vivo mammalian cell comprising administering to said cell at least one double-stranded RNA effector molecule, preferably 2, 3, 4, 5, 6, or more double-stranded RNA effector molecules, each double-stranded RNA effector molecule comprising a sequence selected from the group consisting of SEQ ID NO:18, SEQ ID NO:19, SEQ ID NO:21, SEQ ID NO:22, SEQ ID NO:23, and SEQ ID NO:49; wherein U is substituted for T. In a preferred method, three or four dsRNA effector molecules, each comprising a sequence selected from the group consisting of SEQ ID NO:18, SEQ ID NO:19, SEQ ID NO:23, and SEQ ID NO:49; wherein U is substituted for T; are administered to an in vivo mammalian cell. The double-stranded RNA effector molecules may be prepared exogenously and administered into a mammalian cell or expressed intracellularly in a mammalian cell from a double-stranded RNA expression vector, i.e., an expression vector engineered to express a dsRNA effector molecule in a mammalian cell. In a preferred method, at least three or four dsRNA effector molecules, each comprising a sequence selected from the group consisting of SEQ ID NO:18, SEQ ID NO:19, SEQ ID NO:23, and SEQ ID NO:49; wherein U is substituted for T; are encoded in a dsRNA expression vector which is administered to an in vivo mammalian cell.

A composition for inhibiting the expression of a polynucleotide sequence of hepatitis B virus in an in vivo mammalian cell comprising at least one, preferably 2, 3, 4, 5, 6 or more double-stranded RNA effector molecules, each double-stranded RNA effector molecule comprising a sequence selected from the group consisting of SEQ ID NO:18, SEQ ID NO:19, SEQ ID NO:21, SEQ ID NO:22, SEQ ID NO:23, and SEQ ID NO:49; wherein U is substituted for T. In a preferred composition, at least three or four dsRNA effector molecules are included, each comprising a sequence selected from the group consisting of SEQ ID NO:18, SEQ ID NO:19, SEQ ID NO:23, and SEQ ID NO:49; wherein U is substituted for T. The double-stranded RNA effector molecules may be prepared exogenogenously and the composition comprising two, three, four, five, six, or more dsRNA effector molecules administered into a mammalian cell, or the composition may comprise one or more dsRNA expression constructs capable of expressing in a mammalian cell two, three, four, five, six or more of said dsRNA effector molecules. In a preferred composition, three or four dsRNA effector molecules, each comprising a sequence selected from the group consisting of SEQ ID NO:18, SEQ ID NO:19, SEQ ID NO:23, and SEQ ID NO:49; wherein U is substituted for T, are encoded in a dsRNA expression vector.

A method for inhibiting expression of a polynucleotide sequence of hepatitis B virus in an in vivo mammalian cell comprising administering to said cell at least two, preferably 3, 4, 5, 6 or more, double-stranded RNA effector molecules, each double-stranded RNA effector molecule comprising: (a) a sequence selected from the group consisting of SEQ ID NO: 54, SEQ ID NO: 55, SEQ ID NO:57, SEQ ID NO:58, SEQ ID NO:59, and SEQ ID NO:62; (b) the reverse complement of said selected sequence; and (c) optionally, a sequence linking sequences (a) and (b); wherein U is substituted for T. In a preferred method, said dsRNA effector molecules will comprise 3 or 4 sequences selected from the group consisting of SEQ ID NO: 54, SEQ ID NO: 55, SEQ ID NO:59, and SEQ ID NO:62; wherein U is substituted for T. The double-stranded RNA effector molecules may be stem-loop or hairpin structures and/or duplex double-stranded RNA molecules. The double-stranded RNA effector molecules may be prepared exogenogenously and the two, three, four, five, six, or more dsRNA effector molecules administered into a mammalian cell, or one or more dsRNA expression constructs capable of expressing in a mammalian cell two, three, four, five, six or more of said dsRNA effector molecules may be administered.

A composition for inhibiting expression of a polynucleotide sequence of hepatitis B virus in an in vivo mammalian cell comprising at least two double-stranded RNA effector molecules, each double-stranded RNA effector molecule comprising: (a) a sequence selected from the group consisting of SEQ ID NO: 54, SEQ ID NO: 55, SEQ ID NO:57, SEQ ID NO:58, SEQ ID NO:59, and SEQ ID NO:62; (b) the reverse complement of said selected sequence; and (c) optionally, a sequence linking sequences (a) and (b); wherein U is substituted for T. In a preferred composition, three or four of said dsRNA effector molecules will be included, or encoded in an expression vector, comprising sequences selected from the group consisting of SEQ ID NO: 54, SEQ ID NO: 55, SEQ ID NO:59, and SEQ ID NO:62; wherein U is substituted for T. The double-stranded RNA effector molecules may be prepared exogenously and the composition will comprise two, three, four, five, six, or more of said dsRNA effector molecules for administration into a in vivo mammalian cell, or the composition may comprise one or more dsRNA expression constructs capable of expressing in a mammalian cell two, three, four, five, six or more of said dsRNA effector molecules.

In another aspect the invention relates to methods and compositions for inhibiting expression of a polynucleotide sequence of hepatitis B virus in an in vivo mammalian cell comprising administering to said cell at least two, preferably 3, 4, 5, 6 or more, double-stranded RNA effector molecules, each double-stranded RNA effector molecule comprising: (a) a sequence selected from the group consisting of SEQ ID NO: 50; SEQ ID NO: 51; SEQ ID NO: 52; SEQ ID NO:53; SEQ ID NO: 54, SEQ ID NO: 55, SEQ ID NO: 56; SEQ ID NO:57, SEQ ID NO:58, SEQ ID NO:59, SEQ ID NO: 60; SEQ ID NO:61; and SEQ ID NO:62; (b) the reverse complement of said selected sequence; and (c) optionally, a sequence linking sequences (a) and (b); wherein U is substituted for T.

A polynucleotide sequence comprising SEQ ID NO:49.

A method for inhibiting expression of a polynucleotide sequence of hepatitis C virus in an in vivo mammalian cell comprising administering to said cell at least one double-stranded RNA effector molecule, preferably 2, 3, 4, 5, 6, or more double-stranded RNA effector molecules, comprising (a) an RNA sequence equivalent to a hepatitis C virus DNA coding strand sequence selected from the group consisting of sequence position 9510-9531, 9510-9533, 9510-9534, 9510-9535, 9510-9536, 9514-9534, 9514-9535, 9514-9536, 9514-9539, 9514-9540, 9514-9542, 9517-9539, 9517-9540, 9517-9542, 9517-9544, 9518-9539, 9518-9540, 9518-9542, 9518-9544, 9520-9540, 9520-9542, 9520-9544, 9520-9548, 9521-9542, 9521-9544, 9521-9548, 9521-9549, 9522-9542, 9522-9544, 9522-9548, 9522-9549, 9527-9548, 9527-9549, 9527-9551, 9527-9552, 9527-9553, 9527-9555, 9528-9548, 9528-9549, 9528-9551, 9528-9552, 9528-9553, 9528-9555, 9530-9551, 9530-9552, 9530-9553, 9530-9555, 9530-9557, 9530-9558, 9532-9552, 9532-9553, 9532-9555, 9532-9557, 9532-9558, 9532-9559, 9532-9560, 9537-9557, 9537-9558, 9537-9559, 9537-9560, 9537-9561, 9537-9564, 9538-9558, 9538-9559, 9538-9560, 9538-9561, 9538-9564, 9538-9566, 9541-9561, 9541-9564, 9541-9566, 9541-9568, 9541-9569, 9543-9564, 9543-9566, 9543-9568, 9543-9569, 9543-9571, 9545-9566, 9545-9568, 9545-9569, 9545-9571, 9545-9573, 9546-9564, 9546-9566, 9546-9569, 9546-9571, 9546-9573, 9547-9568, 9547-9569, 9547-9571, 9547-9573, 9547-9575, 9550-9571, 9550-9573, 9550-9575, 9550-9577, 9550-9578, 9554-9575, 9554-9577, 9554-9578, 9554-9580, 9556-9577, 9556-9578, 9556-9580, 9556-9584, 9562-9584, 9562-9586, 9562-9587, 9562-9588, 9562-9589, 9563-9584, 9563-9586, 9563-9587, 9563-9588, 9563-9589, 9563-9591, 9565-9586, 9565-9587, 9565-9588, 9565-9589, 9565-9591, 9565-9593, 9567-9587, 9567-9588, 9567-9589, 9567-9591, 9567-9593, 9567-9595, 9570-9591, 9570-9593, 9570-9595, 9570-9596, 9570-9598, 9572-9593, 9572-9595, 9572-9596, 9572-9598, 9574-9595, 9574-9596, 9574-9598, 9574-9601, 9576-9596, 9576-9598, 9576-9601, 9576-9604, 9579-9601, 9579-9604, 9581-9601, 9581-9604, and 9583-9604 and (b) an RNA sequence which is the reverse complement of the selected sequence equivalent to the hepatitis C virus DNA coding strand sequence. In some embodiments, said RNA sequences (a) and (b) are linked by a loop sequence and the double-stranded RNA effector molecule(s) forms a stem-loop or hairpin dsRNA structure. In some aspects, said double-stranded RNA effector molecule(s) are duplex dsRNAs, formed from two separate RNA strands. In some aspects, the method involves administering to a mammalian cell an expression construct encoding one, two, three, four, five or more of said dsRNA effector molecules. In some embodiments designed to target the HCV minus strand, the dsRNA effector molecule will comprise (a) an RNA sequence corresponding to a hepatitis C virus DNA coding strand sequence as specified above, and (b) the reverse complement of said RNA sequence, optionally linked by a loop sequence. In some embodiments, the dsRNA effector molecule(s) is encoded by an expression construct.

In some aspects the invention relates to a composition for inhibiting the expression of a polynucleotide sequence of hepatitis C virus in an in vivo mammalian cell comprising at least one double-stranded RNA effector molecule, preferably 2, 3, 4, 5, 6 or more double-stranded RNA effector molecules, or a dsRNA expression construct capable of transcribing one, 2, 3, 4, 5, 6 or more of said dsRNA effector molecules in an in vivo mammalian cell, each of said dsRNA effector molecules comprising (a) an RNA sequence equivalent to a hepatitis C virus DNA coding strand sequence selected from the group consisting of sequence position 9510-9531, 9510-9533, 9510-9534, 9510-9535, 9510-9536, 9514-9534, 9514-9535, 9514-9536, 9514-9539, 9514-9540, 9514-9542, 9517-9539, 9517-9540, 9517-9542, 9517-9544, 9518-9539, 9518-9540, 9518-9542, 9518-9544, 9520-9540, 9520-9542, 9520-9544, 9520-9548, 9521-9542, 9521-9544, 9521-9548, 9521-9549, 9522-9542, 9522-9544, 9522-9548, 9522-9549, 9527-9548, 9527-9549, 9527-9551, 9527-9552, 9527-9553, 9527-9555, 9528-9548, 9528-9549, 9528-9551, 9528-9552, 9528-9553, 9528-9555, 9530-9551, 9530-9552, 9530-9553, 9530-9555, 9530-9557, 9530-9558, 9532-9552, 9532-9553, 9532-9555, 9532-9557, 9532-9558, 9532-9559, 9532-9560, 9537-9557, 9537-9558, 9537-9559, 9537-9560, 9537-9561, 9537-9564, 9538-9558, 9538-9559, 9538-9560, 9538-9561, 9538-9564, 9538-9566, 9541-9561, 9541-9564, 9541-9566, 9541-9568, 9541-9569, 9543-9564, 9543-9566, 9543-9568, 9543-9569, 9543-9571, 9545-9566, 9545-9568, 9545-9569, 9545-9571, 9545-9573, 9546-9564, 9546-9566, 9546-9569, 9546-9571, 9546-9573, 9547-9568, 9547-9569, 9547-9571, 9547-9573, 9547-9575, 9550-9571, 9550-9573, 9550-9575, 9550-9577, 9550-9578, 9554-9575, 9554-9577, 9554-9578, 9554-9580, 9556-9577, 9556-9578, 9556-9580, 9556-9584, 9562-9584, 9562-9586, 9562-9587, 9562-9588, 9562-9589, 9563-9584, 9563-9586, 9563-9587, 9563-9588, 9563-9589, 9563-9591, 9565-9586, 9565-9587, 9565-9588, 9565-9589, 9565-9591, 9565-9593, 9567-9587, 9567-9588, 9567-9589, 9567-9591, 9567-9593, 9567-9595, 9570-9591, 9570-9593, 9570-9595, 9570-9596, 9570-9598, 9572-9593, 9572-9595, 9572-9596, 9572-9598, 9574-9595, 9574-9596, 9574-9598, 9574-9601, 9576-9596, 9576-9598, 9576-9601, 9576-9604, 9579-9601, 9579-9604, 9581-9601, 9581-9604, and 9583-9604 and (b) the reverse complement of said selected RNA sequence equivalent to the hepatitis C virus DNA coding strand sequence. In some embodiments, said RNA sequences (a) and (b) are linked by a loop sequence, and the double-stranded RNA effector molecule(s) is a single RNA strand which forms a stem-loop or hairpin dsRNA structure. In other embodiments, the dsRNA effector molecule(s) is a duplex dsRNA molecule formed from two separate strands of RNA.

In another aspect, the invention relates to compositions for inhibiting the expression of a polynucleotide sequence of hepatitis C virus in an in vivo mammalian cell comprising at least one double-stranded RNA effector molecule, preferably 2, 3, 4, 5, 6 or more double-stranded RNA effector molecules, or a dsRNA expression construct capable of expressing one, 2, 3, 4, 5, 6 or more of said dsRNA effector molecules in an in vivo mammalian cell, each of said dsRNA effector molecules comprising (a) a sequence selected from the group consisting of SEQ ID NO: 63; SEQ ID NO: 64; SEQ ID NO: 65; SEQ ID NO:66; SEQ ID NO: 67, SEQ ID NO: 68, SEQ ID NO: 69; SEQ ID NO:70, SEQ ID NO:71, SEQ ID NO:72, SEQ ID NO: 73; SEQ ID NO:74; SEQ ID NO:75; and SEQ ID NO:76; (b) the reverse complement of said selected sequence; and (c) optionally, a sequence linking sequences (a) and (b); wherein U is substituted for T. In certain preferred embodiments, the sequence is selected from the group consisting of SEQ ID NO:72; SEQ ID NO: 73; SEQ ID NO:74; SEQ ID NO: 75; and SEQ ID NO:76.

In another aspect, the invention relates to methods for inhibiting the expression of a polynucleotide sequence of hepatitis C virus in an in vivo mammalian cell comprising administering at least one double-stranded RNA effector molecule, preferably 2, 3, 4, 5, 6 or more double-stranded RNA effector molecules, or a dsRNA expression construct capable of expressing one, 2, 3, 4, 5, 6 or more of said dsRNA effector molecules in an in vivo mammalian cell, each of said dsRNA effector molecules comprising (a) a sequence selected from the group consisting of SEQ ID NO: 63; SEQ ID NO: 64; SEQ ID NO: 65; SEQ ID NO:66; SEQ ID NO: 67, SEQ ID NO: 68, SEQ ID NO: 69; SEQ ID NO:70, SEQ ID NO:71, SEQ ID NO:72, SEQ ID NO: 73; SEQ ID NO:74; SEQ ID NO:75; and SEQ ID NO:76; (b) the reverse complement of said selected sequence; and (c) optionally, a sequence linking sequences (a) and (b); wherein U is substituted for T. In certain preferred embodiments, the sequence is selected from the group consisting of SEQ ID NO:72; SEQ ID NO: 73; SEQ ID NO:74; SEQ ID NO: 75; and SEQ ID NO:76.

In another aspect, the invention relates to a polynucleotide sequence comprising an RNA sequence equivalent to and/or complementary to a hepatitis C virus DNA coding strand sequence selected from the group consisting of sequence position 9510-9531, 9510-9533, 9510-9534, 9510-9535, 9510-9536, 9514-9534, 9514-9535, 9514-9536, 9514-9539, 9514-9540, 9514-9542, 9517-9539, 9517-9540, 9517-9542, 9517-9544, 9518-9539, 9518-9540, 9518-9542, 9518-9544, 9520-9540, 9520-9542, 9520-9544, 9520-9548, 9521-9542, 9521-9544, 9521-9548, 9521-9549, 9522-9542, 9522-9544, 9522-9548, 9522-9549, 9527-9548, 9527-9549, 9527-9551, 9527-9552, 9527-9553, 9527-9555, 9528-9548, 9528-9549, 9528-9551, 9528-9552, 9528-9553, 9528-9555, 9530-9551, 9530-9552, 9530-9553, 9530-9555, 9530-9557, 9530-9558, 9532-9552, 9532-9553, 9532-9555, 9532-9557, 9532-9558, 9532-9559, 9532-9560, 9537-9557, 9537-9558, 9537-9559, 9537-9560, 9537-9561, 9537-9564, 9538-9558, 9538-9559, 9538-9560, 9538-9561, 9538-9564, 9538-9566, 9541-9561, 9541-9564, 9541-9566, 9541-9568, 9541-9569, 9543-9564, 9543-9566, 9543-9568, 9543-9569, 9543-9571, 9545-9566, 9545-9568, 9545-9569, 9545-9571, 9545-9573, 9546-9564, 9546-9566, 9546-9569, 9546-9571, 9546-9573, 9547-9568, 9547-9569, 9547-9571, 9547-9573, 9547-9575, 9550-9571, 9550-9573, 9550-9575, 9550-9577, 9550-9578, 9554-9575, 9554-9577, 9554-9578, 9554-9580, 9556-9577, 9556-9578, 9556-9580, 9556-9584, 9562-9584, 9562-9586, 9562-9587, 9562-9588, 9562-9589, 9563-9584, 9563-9586, 9563-9587, 9563-9588, 9563-9589, 9563-9591, 9565-9586, 9565-9587, 9565-9588, 9565-9589, 9565-9591, 9565-9593, 9567-9587, 9567-9588, 9567-9589, 9567-9591, 9567-9593, 9567-9595, 9570-9591, 9570-9593, 9570-9595, 9570-9596, 9570-9598, 9572-9593, 9572-9595, 9572-9596, 9572-9598, 9574-9595, 9574-9596, 9574-9598, 9574-9601, 9576-9596, 9576-9598, 9576-9601, 9576-9604, 9579-9601, 9579-9604, 9581-9601, 9581-9604, and 9583-9604.

Applicants' invention further provides a method for inhibiting expression of a polynucleotide sequence of hepatitis B virus in an in vivo mammalian cell comprising administering to said cell a double-stranded RNA effector molecule comprising an at least 19 contiguous base pair nucleotide sequence from within a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10; wherein U is substituted for T. In a preferred embodiment of the method, effector sequences from more than one SEQ ID sequence may be administered to the same cell, and/or more than one effector sequence from within the same SEQ ID sequence may be administered to the same cell.

Applicants further provide a method for inhibiting expression of a polynucleotide sequence of hepatitis C virus in an in vivo mammalian cell comprising administering to said cell a double-stranded RNA effector molecule comprising an at least 19 contiguous base pair nucleotide sequence from within a sequence selected from the group consisting of SEQ ID NO:11, SEQ ID NO:12, and SEQ ID NO:27; wherein U is substituted for T. In a preferred embodiment of this aspect of the method, effector molecules from both SEQ ID NO:11 and SEQ ID NO:12 may be administered to the same cell; or from both SEQ ID NO: 11 and SEQ ID NO:27; or from both SEQ ID NO: 12 and SEQ ID NO:27; or from each of SEQ ID NO: 11, SEQ ID NO:12, and SEQ ID NO:27, are administered to the same cell; and/or more than one effector molecule from within the same SEQ ID NO may be administered to the same cell.

Applicants further provide a method for inhibiting expression of both a polynucleotide sequence of hepatitis B virus and a polynucleotide sequence of hepatitis C virus in the same in vivo mammalian cell, comprising administering to said cell a double-stranded RNA effector molecule comprising a first at least 19 contiguous base pair nucleotide sequence from within a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10; wherein U is substituted for T; and a double-stranded RNA effector molecule comprising a second at least 19 contiguous base pair nucleotide sequence from within a sequence selected from the group consisting of SEQ ID NO:11, SEQ ID NO:12, and SEQ ID NO:27; wherein U is substituted for T. In preferred embodiments of this aspect of the invention, effector molecules from more than one of SEQ ID NO:1 through SEQ ID NO:10 may be administered to the same cell; and/or effector molecules from both SEQ ID NO:11 and SEQ ID NO:12; or from both SEQ ID NO: 11 and SEQ ID NO:27; or from both SEQ ID NO: 12 and SEQ ID NO:27; or from SEQ ID NO: 11, SEQ ID NO:12 and SEQ ID NO:27; may be administered to the same cell; and/or more than one effector molecules from within the same SEQ ID NO may be administered to the same cell.

Applicants further provide a composition for inhibiting the expression of a polynucleotide sequence of hepatitis B virus in an in vivo mammalian cell comprising a double-stranded RNA effector molecule comprising an at least 19 contiguous base pair nucleotide sequence from within a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10; wherein U is substituted for T. Preferred embodiments of the composition include wherein effector molecules from more than one of SEQ ID NO:1 through SEQ ID NO:10 are present in the composition; and/or wherein more than one effector molecule from within the same SEQ ID NO is present in the composition.

Applicants further provide a composition for inhibiting the expression of a polynucleotide sequence of hepatitis C virus in an in vivo mammalian cell comprising a double-stranded RNA effector molecule comprising an at least 19 contiguous base pair nucleotide sequence from within a sequence selected from the group consisting of SEQ ID NO:11 and SEQ ID NO:12 and SEQ ID NO:27; wherein U is substituted for T. Preferred embodiments of the composition include wherein effector molecules from both SEQ ID NO:11 and SEQ ID NO:12 are present in the composition; or from both SEQ ID NO: 11 and SEQ ID NO:27; or from both SEQ ID NO: 12 and SEQ ID NO:27; or from each of SEQ ID NO: 11, SEQ ID NO:12, and SEQ ID NO:27, are present in the same composition, and/or wherein more than one effector molecule from within the same SEQ ID NO may be present in the composition.

Applicants further provide a composition for inhibiting the expression of both a polynucleotide sequence of hepatitis B virus and a polynucleotide sequence of hepatitis C virus in a single in vivo mammalian cell comprising a double-stranded RNA effector molecule comprising a first at least 19 contiguous base pair nucleotide sequence from within a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10; wherein U is substituted for T; and a double-stranded RNA effector molecule comprising a second at least 19 contiguous base pair nucleotide sequence from within a sequence selected from the group consisting of SEQ ID NO:11 and SEQ ID NO:12 and SEQ ID NO:27; wherein U is substituted for T. Preferred embodiments of the composition include wherein effector molecules from more than one of SEQ ID NO:1 through SEQ ID NO:10 are present in the composition; and/or wherein effector molecules from both SEQ ID NO:11 and SEQ ID NO:12; or from both SEQ ID NO: 11 and SEQ ID NO:27; or from both SEQ ID NO: 12 and SEQ ID NO:27; or from each of SEQ ID NO: 11, SEQ ID NO:12, and SEQ ID NO:27, are present in the composition; and/or wherein more than one effector sequence from within the same SEQ ID NO may be present in the composition.

In particularly preferred embodiments of the above methods and compositions of the invention, the polynucleotide sequence is present within a double-stranded region of an RNA, and the mammalian cell is a human cell.

Further provided are compositions for inhibiting the expression of a polynucleotide sequence of hepatitis B virus and/or a polynucleotide sequence of hepatitis C virus in mammalian cells, wherein said compositions comprise an at least 19 contiguous nucleotide sequence selected from within SEQ ID NO:1 through SEQ ID NO:12, and SEQ ID NO:27; the complement sequences of said SEQ ID NO:1 through SEQ ID NO:12, and SEQ ID NO: 27 sequences, and mixtures of these sequences. In this embodiment of the invention, the "an at least 19 contiguous nucleotide sequence" is preferably DNA, and the mammalian cell is preferably human. Also provided are expression constructs comprising any of the aforementioned compositions and a mammalian cell comprising said expression constructs.

Another aspect provides for a polynucleotide sequence comprising a sequence selected from SEQ ID NO:14 through SEQ ID NO:26. Another aspect of the invention provides for polynucleotide sequence comprising nucleotides 1-19, 1-20, 1-21, 2-20, 2-21, or 3-21 of a sequence selected from SEQ ID NO:14 through SEQ ID NO:26. Another aspect of the invention provides for a polynucleotide sequence comprising an at least 19 contiguous base pair nucleotide sequence from within a sequence selected from SEQ ID NO:27 through SEQ ID NO:44.

Another aspect provides a composition for inhibiting the expression of a polynucleotide sequence of hepatitis C virus in a mammalian cell, comprising a double-stranded RNA effector molecule comprising an at least 19 contiguous base pair nucleotide sequence from within SEQ ID NO:27; wherein U is substituted for T.

In various aspects of the foregoing methods and compositions, the in vivo mammalian cell is an in vivo human cell.

BRIEF DESCRIPTION OF THE SEQUENCES

SEQ ID NO:1 through SEQ ID NO:10 represent conserved regions of the hepatitis B genome.

SEQ ID NO:11 and SEQ ID NO:12 represent conserved regions of the hepatitis C genome.

SEQ ID NO:13 represents the nucleotide sequence of human U6 promoter.

SEQ ID NO:14 and SEQ ID NO:15 represent eiRNAs that have HBV sequences mapping within SEQ ID NO:5.

SEQ ID NO:16 and SEQ ID NO:17 represent eiRNAs that have HBV 20 sequences mapping within SEQ ID NO:4.

SEQ ID NO:18 represents eiRNA that has an HBV sequence mapping within SEQ ID NO:10.

SEQ ID NO:19 through SEQ ID NO:22 represent eiRNAs that have HBV sequences mapping within SEQ ID NO:3.

SEQ ID NO:23 and SEQ. ID NO:24 represent eiRNAs that have HBV sequences mapping within SEQ ID NO:2.

SEQ ID NO:25 and SEQ ID NO:26 represent eiRNAs that have HBV sequences mapping within SEQ ID NO:1.

SEQ ID NO:27 represents the "X" region of the HCV 3'UTR.

SEQ ID NO:28 through SEQ ID NO:36 represent siRNAs mapping to the HCV 3'UTR.

SEQ ID NO:37 through SEQ ID NO:44 represent siRNAs mapping to the "X" region of the HCV 3'UTR.

SEQ ID NO:45 represents an siRNA mapping to the HCV core.

SEQ ID NO:46 represents an siRNA mapping to lamin.

SEQ ID NO:47 represents the T7 RNA polymerase gene.

SEQ ID NO:48 represents a 5' segment of the hepatitis C virus sequence (corresponds to positions 36 to 358 in Genbank Accession Number AJ238799, with 2 base changes, C to G at AJ238799 position 204 and G to A at AJ238799 position 357).

SEQ ID NO:49 represents an eiRNA (shRNA) molecule to a conserved HBV sequence.

SEQ ID NO:50 through SEQ ID NO:62 represent the first 21 nucleotides of SEQ ID NOs: 14-23, 25-26, and 49.

SEQ ID NO:63 through SEQ ID NO:71 represent the first 21 nucleotides of SEQ ID NOs: 28-36.

SEQ ID NO:72 through SEQ ID NO:76 represent highly conserved coding region sequitopes from the 5' and 3' untranslated regions of HCV.

SEQ ID NO:77 through SEQ ID NO:109 represent highly conserved HCV sequences from the 5' UTR of the HCV (SEQ ID NO: 11).

BRIEF DESCRIPTION OF THE DRAWINGS

FIG. 15 is a table of additional conserved HCV genome sequence segments suitable for generating dsRNA effector molecules which inhibit the expression of polynucleotide sequences of hepatitis C virus, including expressed shRNA for gene silencing. Each sequence represents a DNA coding strand sequence in standard 5' to 3' polarity which (together with its reverse complement) can be utilized to transcribe or design a double-stranded RNA effector molecule, e.g., an shRNA or duplex dsRNA molecule targeted to degrade the negative strand of HCV RNA. E.g., an DNA sequence, followed by a loop sequence (e.g., a 9 base loop sequence as described elsewhere herein), followed by the reverse complement of the sequence given in the table, may be incorporated into an expression construct under the control of an appropriate promoter. The shRNA molecule transcribed from such an expression construct is expected to inhibit expression of HCV polynucleotide sequences and/or mediate dsRNA silencing of HCV. For example, in the case of the 22 base sequence shown for positions 9545-9566, a construct is made to contain a 53 by insert, comprising the 22 base sequence of 9545-9566, a linker or loop sequence, and the reverse complement of the 9545-9566 sequence, preferably under the control of an RNA polymerase III promoter and ending with an RNA polymerase III terminator, e.g., a run of 4, 5, or more T residues. The RNA equivalent of this sequence, having U's instead of T's, would read (in the 5' to 3' direction):

AAAGGUCCGUGAGCCGCUUGAC-XXXXXXXXX-

Figure 1:
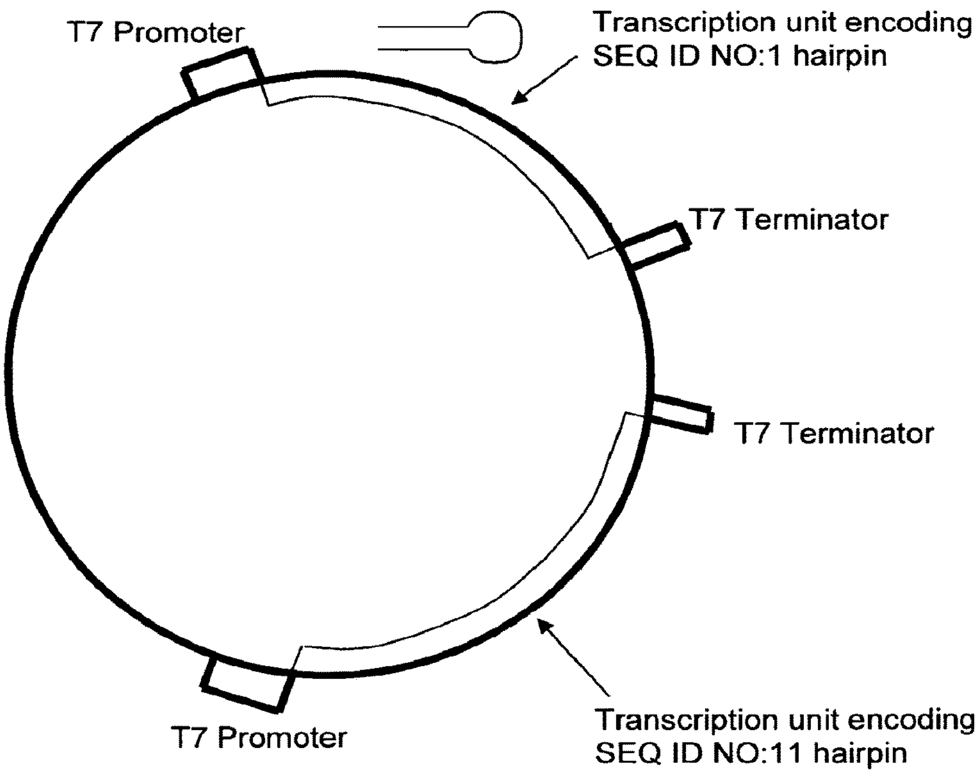
FIG. 1 depicts a vector illustrating placement of the T7 RNA polymerase promoter and T7 RNA polymerase, showing inclusion of hairpin eiRNA sequences.
Figure 2:
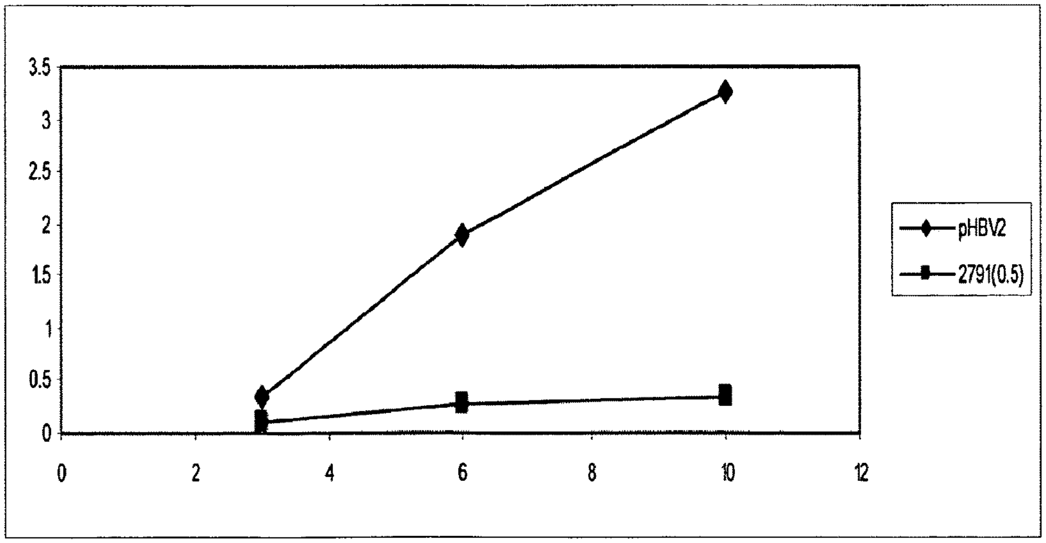
FIG. 2 is a graph showing HBsAg inhibition corresponding to data 15 found in Table 2.
Figure 3:
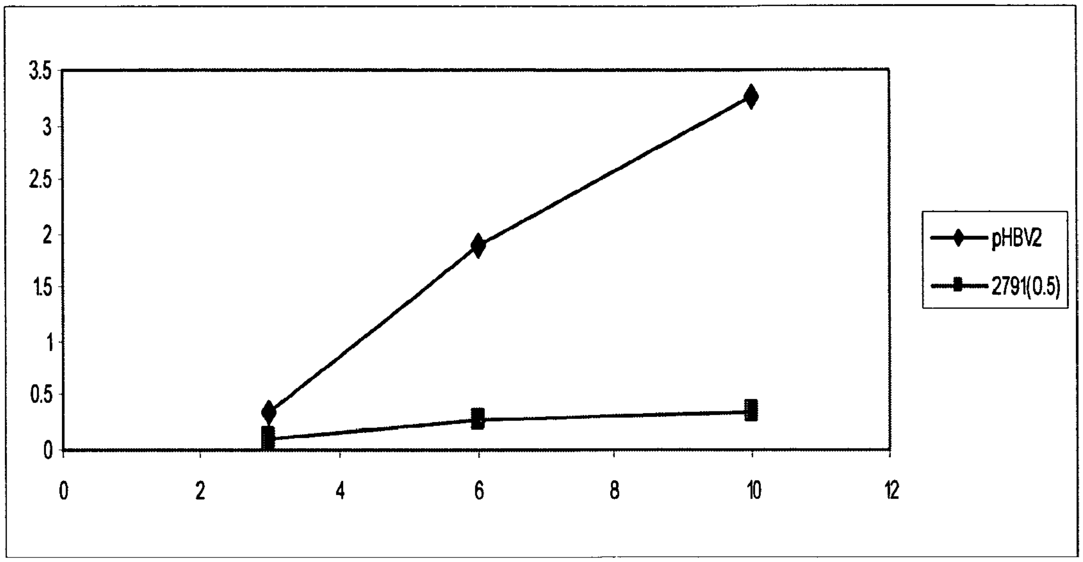
FIG. 3 is a graph showing HBsAg inhibition corresponding to data found in Table 3.
Figure 4:
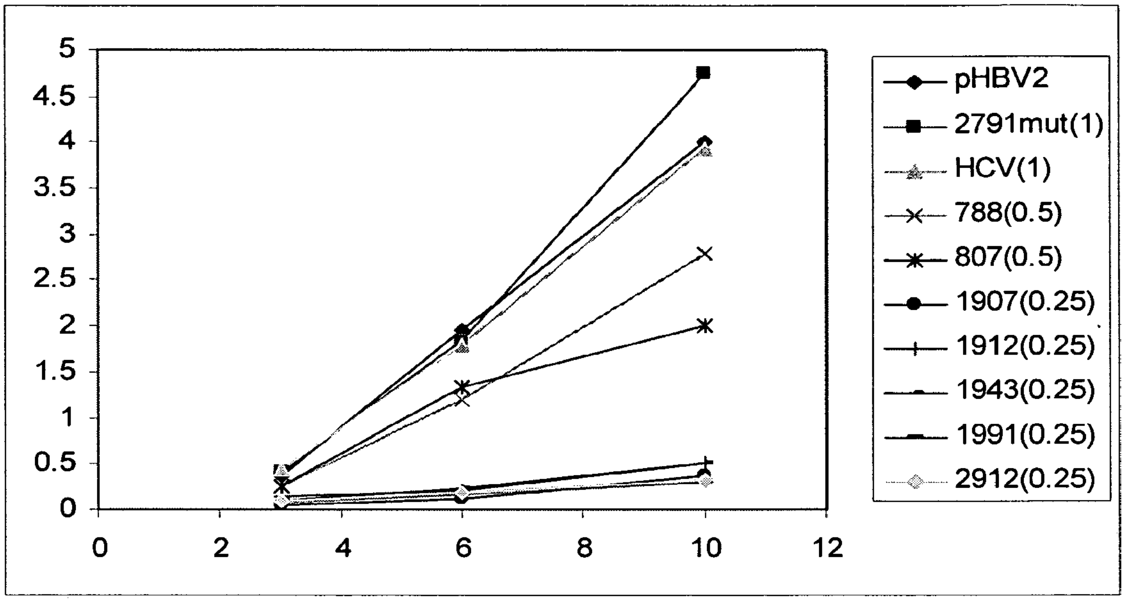
FIG. 4 is a graph showing HBsAg inhibition corresponding to data found in Table 4.
Figure 5:
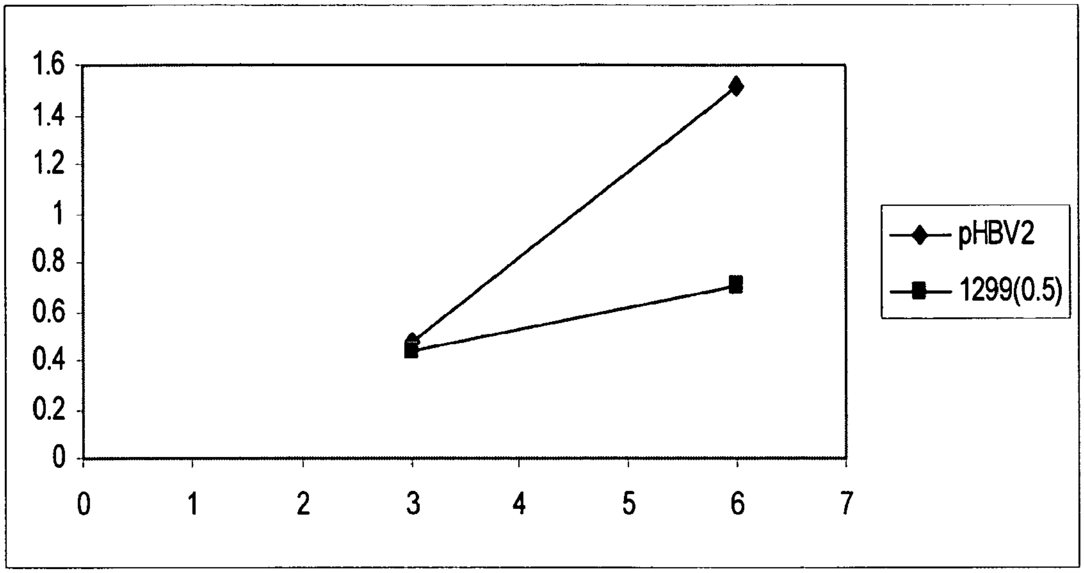
FIG. 5 is a graph showing HBsAg inhibition corresponding to data found in Table 5.
Figure 6:
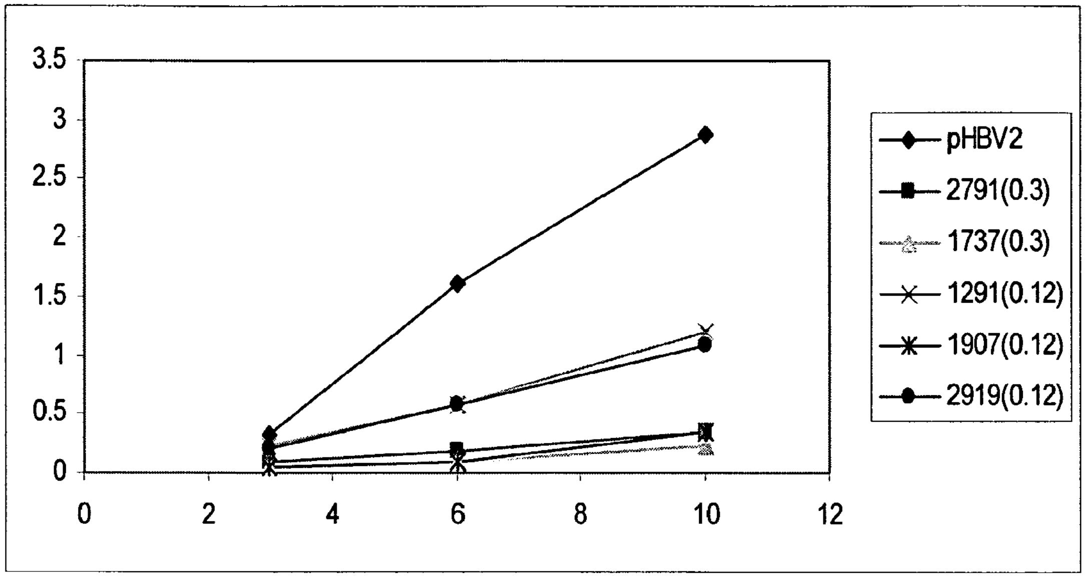
FIG. 6 is a graph showing HBsAg inhibition corresponding to data found in Table 6.
Figure 7:
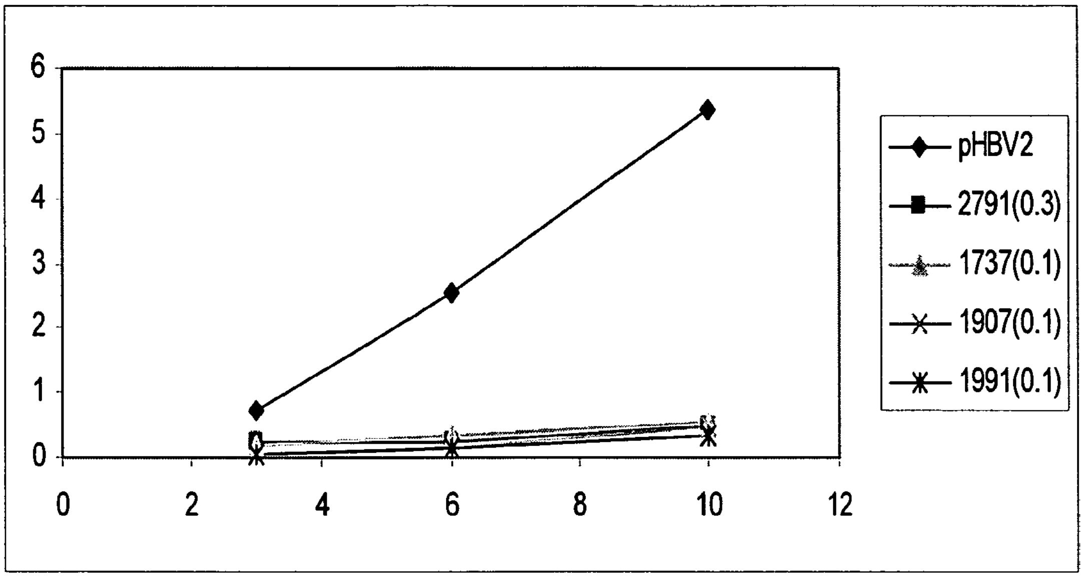
FIG. 7 is a graph showing HBsAg inhibition corresponding to data found in Table 7.
Figure 8:
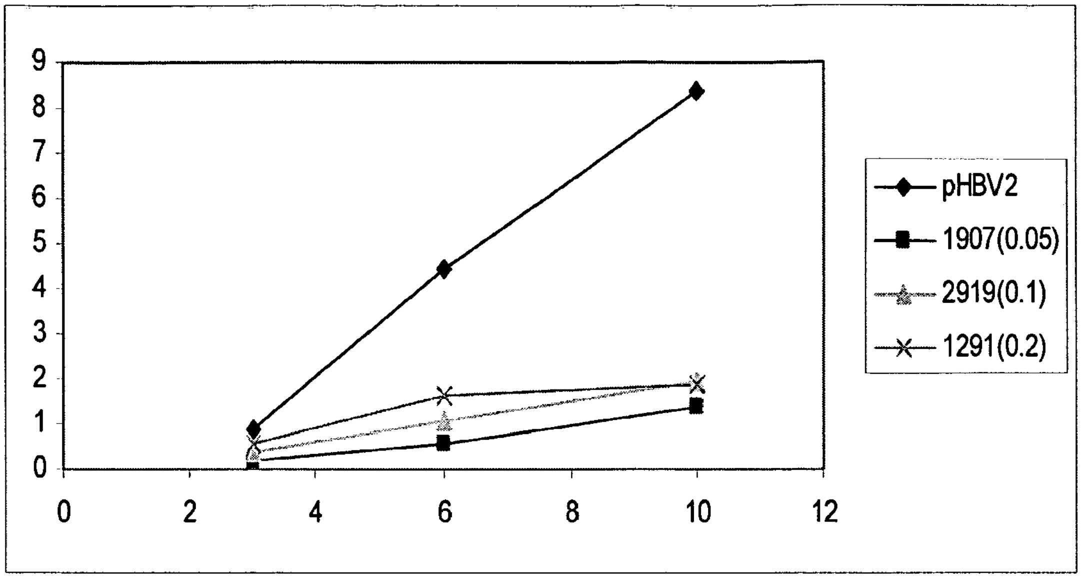
FIG. 8 is a graph showing HBsAg inhibition corresponding to data found in Table 8.

GUCAAGCGGUCACGGACCUU U where X represents bases of the loop that are unable to form stable base pairs with any other portion of the 53 by shRNA sequence. The loop may vary considerably, however, as to both length and nucleotide sequence, so long as the formation of the double-stranded "stem" region of the hairpin is not adversely affected. Thus, in expression constructs that are the subject of this invention, the sequence element above beginning at the end which reads 5' AAAGGT is cloned into an appropriate vector downstream from and operably linked to the promoter. As described elsewhere herein, in preferred embodiments, two, three, four, five, six, seven, or more of the shRNAs encoded by these sequences, optionally, together with other anti-HCV, and/or HBV sequences described herein, are coded into and expressed by a single dsRNA expression vector. In one aspect, each of said multiple stem-loop or shRNA molecules is encoded in a single expression vector within a different expression cassette, each operably linked to a promoter and a terminator, preferably a polymerase III promoter, which may be the same or different. In another aspect, two or more hairpin dsRNA molecules may be expressed from a single promoter, as e.g., a bi-fingered molecule in which a single transcribed RNA strand comprises two such shRNA sequences separated by an unrelated linker sequence. Such constructs, in which a single expression vector provides a mammalian cell with two, three, four, five or more independent dsRNA effector molecules against an HCV and/or HBV target polynucleotide, are particularly desirable for pharmaceutical applications. An alternative means of dsRNA-mediated silencing may be accomplished by preparing shRNAs or duplex dsRNAs corresponding to the identified sequences by chemical synthesis or in vitro expression and delivering them into a cell in order to achieve inhibition of HCV and/or HBV polynucleotide sequences.

DETAILED DESCRIPTION OF THE INVENTION

RNA interference (RNAi) is the process of sequence-specific, post-transcriptional gene silencing or transcriptional gene silencing in animals and plants, initiated by double-stranded RNA (dsRNA) that is homologous in sequence to the silenced gene. Since RNA interference acts in a sequence specific manner, the RNAi molecule used as a drug must be specific to its target. Viral genomes are variable to accommodate resistance to changes in the environment. While HBV and HCV are very desirable viral targets for RNAi, the variability and mutability of the viruses and the high rates of transcription of the viruses make HBV and HCV very challenging targets for any therapeutic and/or prophylactic approach. In order to knock down viral genome replication using RNAi there is a need to identify conserved and unique regions in the viral genome. At that same time, it is very important in order to avoid toxicity that any sequences selected for gene silencing be absent from the human genome.

Human Hepatitis B Virus (HBV)

Hepatitis B virus belongs to the family of hepadnaviruses. The HBV genome is a relaxed circular, partially double stranded DNA of approximately 3,200 base pairs. There are 4 partially overlapping open reading frames encoding the envelope (pre-S/S), core (precore/core), polymerase, and X proteins. The pre-S/S open reading frames encode the large (L), middle (M), and small (S) surface glycoproteins. The precore/core open reading frame is translated into a precore polypeptide, which is modified into a soluble protein, the hepatitis B e antigen (HBeAg) and the nucleocapsid protein, hepatitis B core antigen. Mutations in the core promoter and precore region have been shown to decrease or abolish HBeAg production. The polymerase protein functions as a reverse transcriptase as well as a DNA polymerase. The X protein is a potent transactivator and may play a role in hepatocarcinogenesis.

The replication cycle of HBV begins with the attachment of the virion to the hepatocyte. Inside the hepatocyte nucleus, synthesis of the plus strand HBV DNA is completed and the viral genome is converted into a covalently closed circular DNA (cccDNA). Most antiviral agents that have been examined so far have little or no effect on cccDNA, which accounts for the rapid reappearance of serum HBV DNA after cessation of antiviral therapy. The aims of treatment of chronic hepatitis B are to achieve sustained suppression of HBV replication and/or expression of HBV antigens and remission of liver disease.

In GenBank version 132.0 there are more then 4500 HBV sequences and 340 HBV complete genome sequences (317 Human isolates, 22 isolates from other primates and one woodchuck HBV isolate). This variability constitutes a serious challenge for sequence-specific pharmaceutical approaches such as RNAi. In order to identify conserved sequences suitable for RNAi applications, a comparison between all the complete genomes was carried out using a modified version of ClustalW. Two multiple alignment schemes were generated: the first included all 339 HBV complete genome sequences and the second was limited to all Human HBV isolates. The multiple alignment results were parsed and a table that included scores for sequence conservation at each position in the HBV genome was generated. A sliding window search to identify the longest region of sequence conservation larger then 19 nt in length was created. Three major conserved regions were identified and mapped to GenBank accession no.: AF090840, a Human HBV isolate. The conserved HBV sequences were screened against Genbank sequences of both human genomic and cDNA libraries (Human chromosomes database). It was found that 21 nucleotide and longer segments selected as a permuted "window" from within the conserved regions were unique to HBV, i.e. no perfect sequence matches exist between any 21 nt or longer HBV conserved segments and the available sequence databases of human chromosomal and RNA sequences. For human therapeutic purposes, assuring that homologous human sequences are not inadvertently silenced is as important as selecting conserved viral sequences for RNAi.

Human Hepatitis C Virus

HCV is a small (40 to 60 nanometers in diameter), enveloped, single-stranded RNA virus of the family Flaviviridae and genus hepacivirus. The genome is approximately 10,000 nucleotides and encodes a single polyprotein of about 3,000 amino acids, which is post-transcriptionally cleaved into 10 polypeptides, including 3 major structural (C, E1, and E2) and multiple non-structural proteins ([NS] NS2 to NS5). The NS proteins include enzymes necessary for protein processing (proteases) and viral replication (RNA polymerase). Because the virus mutates rapidly, changes in the envelope proteins may help it evade the immune system. There are at least 6 major genotypes and more than 90 subtypes of HCV. The different genotypes have different geographic distributions. Genotypes 1a and 1b are the most common in the United States (about 75% of cases). Genotypes 2a and 2b (approximately 15%) and 3 (approximately 7%) are less common.

There is little difference in the severity of disease or outcome of patients infected with different genotypes. However, patients with genotypes 2 and 3 are more likely to respond to interferon treatment. The virus replicates at a high rate in the liver and has marked sequence heterogeneity. The main goal of treatment of chronic hepatitis C is to eliminate detectable viral RNA from the blood. Lack of detectable hepatitis C virus RNA from blood six months after completing therapy is known as a sustained response. Studies suggest that a sustained response is equated with a very favorable prognosis and that it may be equivalent to a cure. There may be other more subtle benefits of treatment, such as slowing the progression of liver scarring (fibrosis) in patients who do not achieve a sustained response.

In GenBank version 134.0 there are more then 20,000 HCV sequences and 93 HCV complete genome sequences. A comparison between all the complete genomes was carried out using a modified version of ClustalW. The multiple alignment result was parsed and a table that included scores for sequence conservation at each position in the HCV genome was generated. A sliding window search to identify the longest region of sequence conservation larger then 19 nt in length was created. Three major conserved regions were identified and mapped to GenBank RefSeq (reference sequence) accession no.: NC_004102 this is GenBank annotated HCV complete genome. The three major conserved regions include a portion of the 3' untranslated region of the virus, already described in the literature to be well-conserved among viral isolates. See, e.g., U.S. Pat. No. 5,874,565, "Nucleic Acids Comprising a Highly Conserved Novel 3' Terminal Sequence Element of the Hepatitis C Virus." However, the instant disclosure represents a comprehensive and detailed analysis of these conserved regions to the extent that permitted the discovery and evaluation of multiple short segments suitable for use alone and in combination as a therapeutic for silencing HCV among a diverse patient population. The conserved sequences were screened against Genbank sequences of both human genomic and cDNA libraries (human chromosomes database), and the series of permuted HCV segments greater than 20 bases long with no homology to the human sequence databases were identified.

Non-Homology with Human Sequences

It is equally important to ensure that conserved viral sequences targeted for silencing according to the invention be substantially non-homologous to any naturally occurring, normally functioning, and essential human polynucleotide sequence, so that the dsRNA molecule does not adversely affect the function of any essential naturally occurring mammalian polynucleotide sequence, when used in the methods of this invention. Such naturally occurring functional mammalian polynucleotide sequences include mammalian sequences that encode desired proteins, as well as mammalian sequences that are non-coding, but that provide for essential regulatory sequences in a healthy mammal. Essentially, the RNA molecule useful in this invention must be sufficiently distinct in sequence from any mammalian polynucleotide sequence for which the function is intended to be undisturbed after any of the methods of this invention are performed. Computer algorithms may be used to define the essential lack of homology between the RNA molecule polynucleotide sequence and the normal mammalian sequences.

Since the length of a contiguous dsRNA sequence capable of association with and activation of RISC (RNA-induced silencing complex), is generally considered to be 19-27 base pairs, the identified conserved HBV and HCV sequences were compared with both human genomic libraries and, perhaps even more importantly, with human cDNA libraries as described above. Since human cDNA libraries represent expressed sequences that appear in mRNAs, such mRNA sequences would be especially vulnerable to silencing by homologous dsRNA sequences provided to a cell.

Accordingly, the conserved HBV and HCV sequences were compared with human genomic and cDNA sequences. No human cDNA library matches to the HBV or HCV conserved sequences were identified. (Although there were some matches that were ultimately identified as HBV contamination in the cDNA library.) A comparison with human genomic library sequences revealed no match of any sequence of 21 nts or more, one match of 20 nucleotides, and one match of 19 nucleotides. These matches were in non-coding regions, and likely do not appear in mRNA since cognates were not turned up in the cDNA library. Therefore, they are considered unlikely to be a safety risk, but could be excluded if desired.

Conserved Sequences from HBV and HCV

```
HBV Conserved Region 1
GAACATGGAGA[A(89%)/G(11%)]CA[T(76%)/C(24%)]

[C(78%)/A(20%)/T(2%)][A(78%)/G(21%)/T(1%)1

CATCAGGA[T(65%)/c(35%)]TCCTAGGACCCCTGCTCGTGTTACAGG

CGG[G(88%)/t(12%)]GT[T(89%)/G(11%)]TTTCT[T(94%)/

C(6%)]GTTGACAA[G(64%)/A(36%)]AATCCTCACAATACC

[A(56%)/G(43%)/T(1%)]CAGAGTCTAGACTCGTGGTGGACTTCTC

TCAATTTTCTAGGGG[G(92%)/A(5%)/T(3%)]A[A(41%)/

G(30%)/T(18%)/C(11%)][C(90%)/T(10%)]

HBV Conserved Region 2
TGGATGTGTCT[G(99%)/A(1%)]CGGCGTTTTATCAT

HBV Conserved Region 3
AAGGCCTTTCT[A(43%)/G(43%)/C(14%)][T(56%)/A(37%)/

C(7%)]GT[A(87%)/C(13%)]AACA[A(57%)/G(43%)]TA

[T(59%)/C(41%)][C(59%)/A(41%)]TG[A(92%)/C(8%)]
```

-continued

[A(93%)/C(7%)]CaTTTACCCCGTTGC[T(54%)/C(46%)]

[C(92%)/A(8%)]GGCAACGG[C(74%)/T(24%)]C[A(50/

T(43%)/c(7%)]GG[T(87%)/C(13%)]CT[G(70%)/C(19%)/

T(7%)/A(4%)]TGCCAAGTGTTTGCTGACGCAACCCCCACTGG

[C(48%)/T(38%)/A(14%)]TGGGGCTTGG[C(84%)/T(16%)]

[C(84%)/T(12%)/G(4%)]AT[A(47%)/T(23%)/G(17%)/

C(13%)]GGCCATC[A(83%)/G(17%)][G(92%)/C(8%)]

CGCATGCGTGGAACCTTT[G(84%)/C(13%)/T(3%)]

[T(92%)/A(4%)/C(3%)/G(1%)]G[G(78%)/T(22%)]

CTCCTCTGCCGATCCATACTGCGGAACTCCT[A(88%)/T(9%)/

G(1%)/C(1%)]GC[C(57%)/A(35%)/T(6%)/G(2%)]GC

[T(92%)/C(7%)/G(1%)]TGTTT[T(88%)/C(12%)]

GCTCGCAGC[C(64%)/A(36%)1GGTCTGG[A(87%)/G(13%)]GC

HBV Conserved Region 4
[C(62%)/T(38%)]ACTGTTCAAGCCTCAAGCTGTGCCTTGGGTGGCTT

T[G(88%)/A(12%)]GG[G(92%)/A(8%)]CATGGACATTGAC

[C(92%)/A(8%)]C[T(65%)/G(35%)]TATAAAGAATTTGGAGCT

[A(65%)/T(35%)]CTGTGGAGTTACTCTC[G(62%)/T(35%)/

A(3%)]TTTTTGCCTTC[T(92%)/C(8%)]GACTT[C(92%)/

T(8%)]TTTCCTTC

HBV Conserved Region 5
[C(69%)/del(31%)1[G(69%)/del(31%)]A[G(85%)/

T(11%)/C(4%)]GCAGGTCCCCTAGAAGAAGAACTCCCTCGCCTCGCAG

ACG[C(61%)/A(39%)1AG[A(62%)/G(38%)]TCTCAATCG

[C(88%)/A(12%)]CGCGTCGCAGAAGATCTCAAT[C(92%)/

T(8%)]TCGGGAATCT[C(88%)/T(12%)]AATGTTAGTAT

HBV Conserved Region 6
TTGG[C(84%)/t(16%)][C(84%)/t(12%)/g(4%)]AT

[A(47%)/t(23%)/g(17%)/c(13%)]GGCCATC[A(83%)/ g(17%)][G(92%)/c(8%)]CGCATGCGTGGAACCTTT[G(84%)/ c(13%)/t(3%)][T(92%)/a(4%)/c(3%)/g(1%)]G[G(78%)/ t(22%)]CTCCTCTGCCGATCCATACTGCGGAACTCCT[A(88%)/ t(9%)/g(1%)/c(1%)]GC[C(57%)/a(35%)/t(6%)/g(2%)]

GC[T(92%)/c(7%)/g(1%)]TGTTT[T(88%)/c(12%)]

GCTCGCAGC[C(64%)/a(36%)]GGTCTGG[A(87%)/g(13%)]GC

HBV Conserved Region 7
CTGCCAACTGGAT[C(86%)/T(10%)/A(4%)]CT[C(69%)/

T(25%)/A(6%)]CGCGGGACGTCCTTTGT[T(75%)/C(25%)

TACGTCCCGTC[G(93%)/A(7%)]GCGCTGAATCC[C(86%)/

T(7%)/A(7%)]GCGGACGACCC[C(52%)/G(25%)/T(19%)/

A(4%)]

-continued

HCV Conserved Region 1
[A(74%)/G(19%)/T(7%)][G(82%)/A(15%)/T(3%)]

ATCACTCCCCTGTGAGGAACTACTGTCTTCACGCAGAAAGCGTCTAGCCA

TGGCGTTAGTATGAGTGT[C(92%)/T(7%)]GTGCAGC[C(89%)/

T(10%)]TCCAGG[A(76%)/T(14%)/C(8%)/G(1%)]CCCCCCCTCC

CGGGAGAGCCATAGTGGTCTGCGGAACCGGTGAGTACACCGGAATTGCC

[A(90%)/G(9%)]GGA[C(78%)/T(16%)/A(5%)]GACCGGGTCCTT

TCTTGGAT[G(78%)/T(11%)/A(10%)]AACCCGCTC[A(94%)/

T(5%)]ATGCC[T(90%)/C(9%)]GGA[G(91%)/C(4%)/A(4%)]

ATTTGGGCGTGCCCCCGC[G(85%)/A(14%)]AGAC[T(94%)/

C(5%)]GCTAGCCGAGTAG[T(92%)/C(7%)]GTTGGGT[C(94%)/

T(5%)]GCGAAAGGCCTTGTGGTACTGCCTGATAGGGTGCTTGCGAGTGC

CCCGGGAGGTCTCGTAGACCGTGCA[C(62%)/T(30%)/A(8%)]

CATGAGCAC[A(50%)/G(50%)][A(92%)/C(8%)][A(89%)/

T(11%)]TCC[T(92%)/A(5%)/C(3%)]AAACC[T(84%)/C(14%)/

A(2%)]CAAAGAAAAACCAAA[C(84%)/A(16%)]G[T(84%)/

A(16%)]AACACCAACCG[C(77%)/T(23%)]CGCCCACAGGACGT

[C(81%)/T(18%)/A(1%)]AAGTMCCGGG[C(89%)/T(11%)GG

[T(80%)/C(20%)]GG[T(80%)/C(17%)/A(3%)]CAGATCGTTGG

[T(91%)/C(8%)/G(1%)]GGAGT[T(87%)/A(11%)/C(2%)]TAC

[C(74%)/T(20%)/G(6%)]TGTTGCCGCGCAGGGGCCC[C(87%)/

T(8%)/A(4%)/G(1%)][A(92%)/C(8%)][G(92%)/A(5%)/

C(2%)][G(87%)/A(12%)/T(1%)]TTGGGTGTGCGCGCGAC

[T(78%)/G(13%)/A(7%)/C(2%)]AGGAAGACTTC[C(90%)/

G(5%)/T(5%)]GA[G(90%)/A(10%)]CGGTC[G(79%)/C(12%)/

A(8%)/T(1%)]CA[A(86%)/G(14%)]CC[T(88%)/A(6%)C(6%)]

CG[T(82%)/C(9%)A(9%)]GG[A(87%)/T(8%)/G(3%)/C(2%)]

AG

HCV Conserved Region 2
ATGGC[T(76%)/A(12%)/C(10%)/G(2%)]TGGGATATGATGATGAA

CTGG[T(81%)/C(19%)]C

Conserved Consensus Sequences Presented in SEQ ID Format

The following sequences are presented in the format required per the WIPO Standard ST.25 (1998), using the codes provided under 37 CFR 1.821. SEQ ID NO:1 through SEQ ID NO:10 are derived from the HBV genome SEQ ID NO:11 and SEQ ID NO:12 are derived from the HCV genome.

HBV

SEQ ID NO: 1
GAACATGGAGArCAyhdCATCAGGAyTCCTAGGACCCCTGCTCGTGTTAC

AGGCGGkGTkTTTCTyCTTGACAArAATCCTCACAATACCdCAGAGTCTA

GACTCGTGGTGGACTTCTCTCAATTTTCTAGGGGdAny

-continued

HBV

SEQ ID NO: 2

TGGATGTGTCTrCGGCGTTITATCAT

HBV

SEQ ID NO: 3

AAGGCCTTTCTvhGTmAACArTAymTGmmCCTTTACCCC

GTTGCymGGCAACGGye hGGyCTnTGCCAAGTGTTTGCTGACGCAACCCCCACTGG hTGGGGCTTGGybATnGGCCATCrsCGCATGCGTGGAA

CCTTTbnGkCTCCTCTGCCGATCCATACTGCGGAACTCCTnGCnGCbT

GTTTyGCTCGCAGCmGGTCTGGrGC

HBV

SEQ ID NO: 4 yACTGTTCAAGCCTCAAGCTGTGCCTTGGGTGGCTTTrG

GrCATGGACATTGACmCkTATAAAGAATTTGGAGCTwCTGTGGAGTTACT

CTCdTTTTTGCCTTCyGACTTyTTTCCTTC

HBV

SEQ ID NO: 5

CGAbGCAGGTCCCCTAGAAGAAGAACTCCCTCGCCTCGCAGACG mAGrTCTCAATCGmCGCGTCGCAGAAGATCTCAATyTCGGGAATCTyAAT

GTTAGTAT

HBV

SEQ ID NO: 6

AbGCAGGTCCCCTAGAAGAAGAACTCCCTCGCCTCGCAGACGmA

GrTCTCAATCGmCGCGTCGCAGAAGATCTCAATyTCGGGAATCTyAATGT

TAGTAT

HBV

SEQ ID NO: 7

CAbGCAGGTCCCCTAGAAGAAGAACTCCCTCGCCTCGCAGACGm

AGrTCTCAATCGmCGCGTCGCAGAAGATCTCAATyTCGGGAATCTyAATG

TTAGTAT

HBV

SEQ ID NO: 8

GAbGCAGGTCCCCTAGAAGAAGAACTCCCTCGCCTCGCAGACGm

AGrTCTCAATCGmCGCGTCGCAGAAGATCTCAATyTCGGGAATCTyAATG

TTAGTAT

HBV

SEQ ID NO: 9

TTGGybATnGGCCATCrsCGCATGCGTGGAACCTTTbnGk

CTCCTCTGCCGATCCATACTGCGGAACTCCTnG

CnGCbTGTTTyGCTCGCAGCmGGTCTGGrGC

HBV

SEQ ID NO: 10

CTGCCAACTGGAThCThCGCGGGACGTCCTTTGTyTACG

TCCCGTCrGCGCTGAATCChGCGGACGACCCn

HCV

SEQ ID NO: 11

DdATCACTCCCCTGTGAGGAACTACTGTCTTCACGCAGA

AAGCGTCTAGCCATGGCGTTAGTATGAGTGTyGTGCAGCyTCCAGGn

CCCCCCCTCCCGGGAGAGCCATAGTGGTCTGCGGAACCGGTGAGTA

-continued

CACCGGAATTGCCrGGAhGACCGGGTCCTTTCTTGGATdAACCCGCT

CwATGCCyGGAvATTTGGGCGTGCCCCCGCrAGACyGCTAGCCGAGT

AGyGTTGGGTyGCGAAAGGCCTTGTGGTACTGCCTGATAGGGTGCTTGCG

AGTGC CCCGGGAGGTCTCGTAGACCGTGCAhCATGAGCACrmwTCChAA

ACChCAAAGAAAAACCAAAmGwAACACCAACCGyCGCC

CACAGGACGThAAGTTCCCGGGyGGyGGhCAGATCGTTGGbGGAGThTAC bTGTTGCCGCGCAGGGGCCCnmvdTTGGGTGTGCGCGCGACnAGGA AGACTTCbGArCGGTCnCArCChCGhGGnAG Double Stranded RNA Gene Silencing/RNAi By "nucleic acid composition" or "nucleotide" composition is meant any one or more compounds in which one or more molecules of phosphoric acid are combined with a carbohydrate (e.g., pentose or hexose) which are in turn combined with bases derived from purine (e.g., adenine) and from pyrimidine (e.g., thymine). Particular naturally occurring nucleic acid molecules include genomic deoxyribonucleic acid (DNA) and host ribonucleic acid (RNA), as well as the several different forms of the latter, e.g., messenger RNA (mRNA), transfer RNA (tRNA), and ribosomal RNA (rRNA). Also included are different DNA molecules which are complementary (cDNA) to the different RNA molecules. Synthesized DNA or a hybrid thereof with naturally occurring DNA, as well as DNA/RNA hybrids, and peptide nucleic acid (PNA) molecules (Gambari, Curr Pharm Des 2001 November; 7(17):1839-62) can also be used.

It is contemplated that where the desired nucleic acid molecule is RNA, the T (thymine) in the sequences provided herein is substituted with U (uracil). For example, SEQ ID NO:1 through SEQ ID NO:44 are disclosed herein as DNA sequences. It will be obvious to one of ordinary skill in the art that an RNA effector molecule comprising sequences from any of the aforementioned SEQ ID NOs will have T substituted with U.

Nucleic acids typically have a sequence of two or more covalently bonded naturally-occurring or modified deoxyribonucleotides or ribonucleotides. Modified nucleic acids include, e.g., peptide nucleic acids and nucleotides with unnatural bases.

By "dsRNA" or "dsRNA effector molecule" is meant a nucleic acid containing a region of two or more nucleotides that are in a double stranded conformation. It is envisioned that the conserved viral sequences of the invention may be utilized in any of the many compositions of "dsRNA effector molecules" known in the art or subsequently developed which act through a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other. In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. Desirably, the regions of complementarity are at least 70, 80, 90, 95, 98, or 100% complementary to each other and to a target nucleic acid sequence. Desirably, the region of the dsRNA that is present in a double stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. Desirable RNA/DNA hybrids include a DNA strand or region that is an antisense strand or region (e.g, has at least 70, 80, 90, 95, 98, or 100% complementarity to a target nucleic acid) and an RNA strand or region that is a sense strand or region (e.g, has at least 70, 80, 90, 95, 98, or 100% identity to a target nucleic acid), and vice versa. In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999. In other embodiments, the dsRNA contains coding sequence or non-coding sequence, for example, a regulatory sequence (e.g., a transcription factor binding site, a promoter, or a 5' or 3' untranslated region (UTR) of an mRNA). Additionally, the dsRNA can be any of the at least partially dsRNA molecules disclosed in WO 00/63364, filed Apr. 19, 2000 (see, for example, pages 8-22), as well as any of the dsRNA molecules described in U.S. Provisional Application 60/399,998 filed Jul. 31, 2002, and PCT/US2003/024028, filed 31 Jul. 2003; and U.S. Provisional Application 60/419,532 filed Oct. 18, 2002, and PCT/US2003/033466, filed 20 Oct. 2003, the teaching of which is hereby incorporated by reference. Any of the dsRNAs may be expressed in vitro or in vivo using the methods described herein or standard methods, such as those described in WO 00/63364, filed Apr. 19, 2000 (see, for example, pages 16-22). In some preferred embodiments, multiple anti-HBV and/or anti-HCV dsRNA effector molecules of the invention are transcribed in a mammalian cell from one or more expression constructs each comprising multiple polymerase III promoter expression cassettes as described in more detail in U.S. 60/603,622; U.S. 60/629,942; and PCT/US05/29976 filed 23 Aug. 2005; "Multiple Polymerase III Promoter Expression Constructs"; the teaching of which is incorporated by reference.

dsRNA "Hairpin" Constructs or dsRNA "Hairpin" Expression Vectors: Constructs encoding a unimolecular hairpin dsRNA are more desirable for some applications than constructs encoding duplex dsRNA (i.e., dsRNA composed of one RNA molecule with a sense region and a separate RNA molecule with an antisense region) because the single-stranded RNA with inverted repeat sequences more efficiently forms a dsRNA hairpin structure. This greater efficiency is due in part to the occurrence of transcriptional interference arising in vectors containing converging promoters that generate duplex dsRNA. Transcriptional interference results in the incomplete synthesis of each RNA strand thereby reducing the number of complete sense and antisense strands that can base-pair with each other and form duplexes. Transcriptional interference can be overcome, if desired, through the use of (i) a two vector system in which one vector encodes the sense RNA and the second vector encodes the antisense RNA, (ii) a bicistronic vector in which the individual strands are encoded by the same plasmid but through the use of separate cistrons, or (iii) a single promoter vector that encodes a hairpin dsRNA, i.e., an RNA in which the sense and antisense sequences are encoded within the same RNA molecule. Hairpin-expressing vectors have some advantages relative to the duplex vectors. For example, in vectors that encode a duplex RNA, the RNA strands need to find and base-pair with their complementary counterparts soon after transcription. If this hybridization does not happen, the individual RNA strands diffuse away from the transcription template and the local concentration of sense strands with respect to antisense strands is decreased. This effect is greater for RNA that is transcribed intracellularly compared to RNA transcribed in vitro due to the lower levels of template per cell. Moreover, RNA folds by nearest neighbor rules, resulting in RNA molecules that are folded co-transcriptionally (i.e., folded as they are transcribed). Some percentage of completed RNA transcripts is therefore unavailable for base-pairing with a complementary second RNA because of intra-molecular base-pairing in these molecules. The percentage of such unavailable molecules increases with time following their transcription. These molecules may never form a duplex because they are already in a stably folded structure. In a hairpin RNA, an RNA sequence is always in close physical proximity to its complementary RNA. Since RNA structure is not static, as the RNA transiently unfolds, its complementary sequence is immediately available and can participate in base-pairing because it is so close. Once formed, the hairpin structure is predicted to be more stable than the original non-hairpin structure. Especially desirable are, e.g., "forced" hairpin constructs, partial hairpins capable of being extended by RNA-dependent RNA polymerase to form dsRNA hairpins, as taught in U.S. Ser. No. 60/399,998P, filed 31 Jul. 2002; and PCT/US2003/024028, "Double Stranded RNA Structures and Constructs and Methods for Generating and Using the Same," filed 31 Jul. 2003; as well as the "udderly" structured hairpins, hairpins with mismatched regions, and multiepitope constructs as taught in U.S. Ser. No. 60/419,532, filed 18 Oct. 2002, and PCT/US2003/033466, "Double-Stranded RNA Structures and Constructs, and Methods for Generating and Using the Same," filed 20 Oct. 2003.

By "short dsRNA" is meant a dsRNA that has about 200, 100, 75, 50, 45, 40, 35, 30, 29, 28, 27, 26, 25, 24, 23, 22, 21, 20 or 19 contiguous nucleotides in length that are in a double stranded conformation. Desirably, the short dsRNA comprises a double-stranded region of at least 19 contiguous basepairs in length identical/complementary to a target sequence to be inhibited. In desirable embodiments, the double stranded region is between 19 to 50, 19 to 40, 19 to 30, 19 to 25, 20 to 25, 21 to 23, 25 to 30, or 30 to 40 contiguous basepairs in length, inclusive. In some embodiments, the short dsRNA is between 30 to 50, 50 to 100, 100 to 200, 200 to 300, 400 to 500, 500 to 700, 700 to 1000, 1000 to 2000, or 2000 to 5000 nucleotides in length, inclusive and has a double stranded region that is between 38 and 60 contiguous basepairs in length, inclusive. In one embodiment, the short dsRNA is completely double stranded. In some embodiments, the short dsRNA is between 11 and 30 nucleotides in length, and the entire dsRNA is double stranded. In other embodiments, the short dsRNA has one or two single stranded regions. In some embodiments, the short dsRNA is a "shRNA" or "short-hairpin RNA" or "shRNA effector molecule" or "dsRNA hairpin", meaning an RNA molecule of less than approximately 400 to 500 nucleotides (nt) in length, preferably less than 100 to 200 nt in length, in which at least one stretch of at least about 15 to 100 nucleotides (preferably 17 to 50 nt; more preferably 19 to 29 nt) is base paired with a complementary sequence located on the same RNA molecule, and where said sequence and complementary sequence are separated by an unpaired region of at least about 4 to 7 nucleotides (preferably about 9 to about 15 nucleotides) which forms a single-stranded loop above the stem structure created by the two regions of base complementarity. The shRNA molecules comprise at least one stem-loop structure comprising a double-stranded stem region of about 17 to about 100 bp; about 17 to about 50 bp; about 40 to about 100 bp; about 18 to about 40 bp; or from about 19 to about 29 bp; homologous and complementary to a target sequence to be inhibited; and an unpaired loop region of at least about 4 to 7 nucleotides; preferably about 9 to about 15 nucleotides, which forms a single-stranded loop above the stem structure created by the two regions of base complementarity. Included shRNAs are dual or bi-finger (i.e., having two stem-loop structures) and multi-finger hairpin dsRNAs (having multiple stem-loop structures), in which the RNA molecule comprises two or more of such stem-loop structures separated by single-stranded spacer regions. In some embodiments, an expression construct may be used to express one or more of such shRNA molecules in a mammalian cell, including multiple copies of the same, and/or one or more, including multiple different, short hairpin RNA molecules. Short hairpin RNA molecules considered to be the "same" as each other are those that comprise only the same double-stranded sequence, and short hairpin RNA molecules considered to be "different" from each other will comprise different double-stranded sequences, regardless of whether the sequences to be targeted by each different double-stranded sequence are within the same, or a different gene, such as, e.g., sequences of a promoter region and of a transcribed region (mRNA) of the same gene, or sequences of two different genes.

In particular embodiments, the short dsRNA binds PKR or another protein in a dsRNA-mediated stress response pathway. Desirably, such a short dsRNA inhibits the dimerization and activation of PKR by at least 20, 40, 60, 80, 90, or 100%. In some desirable embodiments, the short dsRNA inhibits the binding of a long dsRNA to PKR or another component of a dsRNA-mediated stress response pathway by at least 20, 40, 60, 80, 90, or 100%. See also the teaching of U.S. Ser. No. 10/425,006, filed 28 Apr. 2003, "Methods of Silencing Genes Without Inducing Toxicity", Pachuk, as to utilization of short dsRNAs in conjunction with other dsRNAs to avoid dsRNA-mediated toxicity. The applicants have demonstrated, however, that dsRNA molecules, even long dsRNA molecules, are in general unlikely to evoke a significant dsRNA stress response, including a PKR or interferon or "panic" response, if they are expressed intracellularly in the mammalian (or other vertebrate) cell in which the RNAi effect is desired. See, e.g., US 2002/0132257, "Use of post-transcriptional gene silencing for identifying nucleic acid sequences that modulate the function of a cell". Accordingly, such "expressed interfering RNA molecules" or "eiRNA" molecules and "eiRNA expression constructs", i.e., dsRNA molecules (or the corresponding dsRNA expression constructs) expressed intracellularly or endogenously in vivo within the mammalian cell in which dsRNA gene silencing or RNAi is induced, are preferred in some aspects of the invention.

By "at least 19 contiguous base pair nucleotide sequence" is meant that a nucleotide sequence can start at any nucleotide within one of the disclosed sequences, so long as the start site is capable of producing a polynucleotide of at least 19 contiguous base pairs. For example, an at least 19 contiguous base pair nucleotide sequence can comprise nucleotide 1 through nucleotide 19, nucleotide 2 through nucleotide 20, nucleotide 3 through nucleotide 21, and so forth to produce a 19mer. Thus, a 20mer can comprise nucleotide 1 through nucleotide 20, nucleotide 2 through nucleotide 21, nucleotide 3 through nucleotide 22, and so forth. Similar sequences above 20 contiguous nucleotides, e.g., 21, 22, 23, 24, 25, 26, 27, etc. selected from within the conserved sequences are envisioned. Such a sequence of at least 19 contiguous nucleotides (in double-stranded conformation with its complement) is "an at least 19 contiguous base pair sequence" and may be present as a duplex dsRNA, within a dsRNA hairpin, or encoded in a dsRNA expression construct.

By "expression vector" is meant any double stranded DNA or double stranded RNA designed to transcribe an RNA, e.g., a construct that contains at least one promoter operably linked to a downstream gene or coding region of interest (e.g., a cDNA or genomic DNA fragment that encodes a protein, or any RNA of interest, optionally, e.g., operatively linked to sequence lying outside a coding region, an antisense RNA coding region, a dsRNA coding region, or RNA sequences lying outside a coding region). Transfection or transformation of the expression vector into a recipient cell allows the cell to express RNA or protein encoded by the expression vector. An expression vector may be a genetically engineered plasmid, virus, or artificial chromosome derived from, for example, a bacteriophage, adenovirus, retrovirus, poxvirus, or herpesvirus.

By an "expression construct" is meant any double-stranded DNA or double-stranded RNA designed to transcribe an RNA, e.g., a construct that contains at least one promoter operably linked to a downstream gene or coding region of interest (e.g., a cDNA or genomic DNA fragment that encodes a protein, or any RNA of interest). Transfection or transformation of the expression construct into a recipient cell allows the cell to express RNA or protein encoded by the expression construct. An expression construct may be a genetically engineered plasmid, virus, or artificial chromosome derived from, for example, a bacteriophage, adenovirus, retrovirus, poxvirus, or herpesvirus. An expression construct does not have to be replicable in a living cell, but may be made synthetically. An expression construct or expression vector engineered to express a double-stranded RNA effector molecule or dsRNA molecule is a “dsRNA expression construct” or “dsRNA expression vector”.

In one embodiment of the invention, a recombinant expression vector or expression construct is engineered to express multiple, e.g., three, four, five or more short hairpin dsRNA effector molecules, each expressed from a different expression cassette comprising a polymerase III promoter, one or more, including all of which, may be different from the others. In one aspect of the invention, a recombinant expression vector transcribing three, four, five or more different shRNA molecules (each comprising a double-stranded “stem” region comprising at least 19 contiguous basepairs from/complementary to a conserved HBV and/or HCV sequence) is used to inhibit replication of hepatitis B virus (HBV) and/or hepatitis C virus (HCV). In one embodiment, each shRNA molecule is expressed under the control of a polymerase III promoter, e.g., 7SK, H1, and U6, which may be the same of different. Such dsRNA expression constructs comprising multiple polymerase III expression cassettes are described in greater detail in PCT/US05/29976, “Multiple Polymerase III Promoter Expression Constructs”, the teaching of which is hereby incorporated by reference. In one aspect, a recombinant expression vector or expression construct of the invention may express one or more bi-fingered or multi-fingered dsRNA hairpin molecules from one or more polymerase III promoter-driven transcription units as well as one or more single hairpin dsRNA molecules from one or more polymerase III promoter-driven transcription units. It will be understood that in any of said expression constructs transcribing a hairpin dsRNA from a polymerase III promoter, the hairpin dsRNA may be a single hairpin dsRNA or a bi-fingered, or multi-fingered dsRNA hairpin as described in WO2004/035765, published 29 Apr. 2004, or a partial or forced hairpin structure as described in WO2004/011624, published 5 Feb. 2004, the teaching of which is incorporated herein by reference.

By “operably linked” is meant that a nucleic acid sequence or molecule and one or more regulatory sequences (e.g., a promoter, enhancer, repressor, terminator) are connected in such a way as to permit transcription of an RNA molecule, e.g., a single-stranded RNA molecule such as a sense, antisense, a dsRNA hairpin, or an mRNA, or permit expression and translation and/or secretion of the product (i.e., a polypeptide) of the nucleic acid molecule when the appropriate molecules are bound to the regulatory sequences.

By a “promoter” is meant a nucleic acid sequence sufficient to direct transcription of a covalently linked nucleic acid molecule. Also included in this definition are those transcription control elements (e.g., enhancers) that are sufficient to render promoter-dependent gene expression controllable in a cell type-specific, tissue-specific, or temporal-specific manner, or that are inducible by external signals or agents; such elements, which are well-known to skilled artisans, may be found in a 5' or 3' region of a gene or within an intron. See, e.g., published U.S. Patent Application No. 2005/0130184 A1, 16 Jun. 2005, Xu et al., directed to modified polymerase III promoters which utilize polymerase II enhancer elements, as well as Published U.S. Patent Application No. 2005/0130919 A1, 16 Jun. 2005, Xu et al., directed to regulatable polymerase III and polymerase II promoters, the teaching of which is hereby incorporated by reference. Desirably a promoter is operably linked to a nucleic acid sequence, for example, a cDNA or a gene sequence, or a sequence encoding a dsRNA, e.g., a shRNA, in such a way as to permit expression of the nucleic acid sequence.

The RNA molecule according to this invention may be delivered to the mammalian cell or extracellular pathogen present in the mammalian cell in the composition as a dsRNA effector molecule or partially double stranded RNA sequence, or RNA/DNA hybrid, which was made in vitro by conventional enzymatic synthetic methods using, for example, the bacteriophage T7, T3 or SP6 RNA polymerases according to the conventional methods described by such texts as the Promega Protocols and Applications Guide, (3rd ed. 1996), eds. Doyle, ISBN No. 1 57 Alternatively these molecules may be made by chemical synthetic methods in vitro [see, e.g., Q. Xu et al., Nucleic Acids Res., 24(18): 3643-4 (September 1996); N. Naryshkin et al., Bioorg. Khim., 22(9):691-8 (September 1996); J. A. Grasby et al., Nucleic Acids Res., 21(19):4444-50 (September 1993); C. Chaix et al., Nucleic Acids Res. 17:7381-93 (1989); S. H. Chou et al., Biochem., 28(6):2422-35 (March 1989); 0. Odal el al., Nucleic Acids Symp. Ser., 21:105-6 (1989); N. A. Naryshkin et al., Bioorg. Khim, 22(9):691-8 (September 1996); S. Sun et al., RNA, 3(11):1352-1363 (November 1997); X. Zhang et al., Nucleic Acids Res., 25(20):3980-3 (October 1997); S. M. Grvaznov el al., Nucleic Acids Res., 2-6 (18):4160-7 (September 1998); M. Kadokura et al., Nucleic Acids Symp. Ser., 37:77-8 (1997); A. Davison et al., Biorned. Pept. Proteins. Nucleic Acids, 2(I):1-6 (1996); and A. V. Mudrakovskaia et al., Bioorg. Khirn., 17(6):819-22 (June 1991)].

Still alternatively, the RNA molecule of this invention can be made in a recombinant microorganism, e.g., bacteria and yeast or in a recombinant host cell, e.g., mammalian cells, and isolated from the cultures thereof by conventional techniques. See, e.g., the techniques described in Sambrook et al, MOLECULAR CLONING, A LABORATORY MANUAL, 2nd Ed.; Cold Spring Harbor Laboratory Press, Cold Spring Harbor, N.Y., 1989, which is exemplary of laboratory manuals that detail these techniques, and the techniques described in U.S. Pat. Nos. 5,824,538; 5,877,159; and 5,643,771, incorporated herein by reference.

Such RNA molecules prepared or synthesized in vitro may be directly delivered to the mammalian cell or to the mammal as they are made in vitro. The references above provide one of skill in the art with the techniques necessary to produce any of the following specific embodiments, given the teachings provided herein. Therefore, in one embodiment, the “agent” of the composition is a duplex (i.e., it is made up of two strands), either complete or partially double stranded RNA.

In another embodiment, the agent is a single stranded RNA sense strand. In another embodiment, the agent of the composition is a single stranded RNA anti-sense strand.

Preferably the single stranded RNA sense or anti-sense strand forms a hairpin at one or both termini. Desirably, the single stranded RNA sense or anti-sense strand forms a hairpin at some intermediate portion between the termini. Such a single stranded RNA sense or anti-sense strand may also be designed to fold back upon itself to become partially double stranded in vitro or in vivo. Yet another embodiment of an extant RNA molecule as the effective agent used in the compositions is a single stranded RNA sequence comprising both a sense polynucleotide sequence and an antisense polynucleotide sequence, optionally separated by a non-base paired polynucleotide sequence. Preferably, this single stranded RNA sequence has the ability to become double-stranded once it is in the cell, or in vitro during its synthesis. In desirable embodiments, a sequence of at least about 19 to 29 contiguous basepairs will assume a double-stranded conformation. In desirable embodiments, the double-stranded region will include an at least about 19 contiguous basepair sequence identical/complementary to a target nucleotide sequence to be downregulated or inhibited.

Still another embodiment of this invention is an RNA/DNA hybrid as described above.

Still another embodiment of the synthetic RNA molecule is a circular RNA molecule that optionally forms a rod structure [see, e.g., K-S. Wang et al., Nature 323:508-514 (1986)] or is partially double-stranded, and can be prepared according to the techniques described in S. Wang et al., Nucleic Acids Res., 22(12):2326-33 (June 1994); Y. Matsumoto et al., Proc. Natl. Acad. Sci, USA, 87(19):7628-32 (October 1990); E. Ford & M. Ares, Proc. Natl. Acad. Sci. USA 91(8):3117-21 (April 1994); M. Tsagris et al., Nucleic Acids Res., 19 7):1605-12 (April 1991); S. Braun et al., Nucleic Acids Res. 24(21):4152-7 (November 1996); Z. Pasman et al., RNA, 2(6):603-10 (June 1996); P. G. Zaphiropoulos, Proc. Natl. Acad. Sci., USA, 93(13):6536-41 (June 1996); D. Beaudry et al., Nucleic Acids Res., 23(15):3064-6 (August 1995), all incorporated herein by reference. Still another agent is a double-stranded molecule comprised of RNA and DNA present on separate strands, or interspersed on the same strand.

Alternatively, the RNA molecule may be formed in vivo and thus delivered by a "delivery agent" which generates such a partially double-stranded RNA molecule in vivo after delivery of the agent to the mammalian cell or to the mammal. Thus, the agent which forms the composition of this invention is, in one embodiment, a double stranded DNA molecule "encoding" one of the above-described RNA molecules, e.g., a dsRNA expression vector or expression construct. The DNA agent provides the nucleotide sequence which is transcribed within the cell to become a double stranded RNA. In another embodiment, the DNA sequence provides a deoxyribonucleotide sequence which within the cell is transcribed into the above-described single stranded RNA sense or anti-sense strand, which optionally forms a hairpin at one or both termini or folds back upon itself to become partially double stranded. The DNA molecule which is the delivery agent of the composition can provide a single stranded RNA sequence comprising both a sense polynucleotide sequence and an anti-sense polynucleotide sequence, optionally separated by a nonbase paired polynucleotide sequence, and wherein the single stranded RNA sequence has the ability to become double-stranded. Alternatively, the DNA molecule which is the delivery agent provides for the transcription of the above-described circular RNA molecule that optionally forms a rod structure or partial double strand in vivo. The DNA molecule may also provide for the in vivo production of an RNA/DNA hybrid as described above, or a duplex containing one RNA strand and one DNA strand. These various DNA molecules may be designed by resort to conventional techniques such as those described in Sambrook, cited above or in the Promega reference, cited above.

A latter delivery agent of the present invention, which enables the formation in the mammalian cell of any of the above-described RNA molecules, can be a DNA single stranded or double stranded plasmid or vector. Expression vectors designed to produce RNAs as described herein in vitro or in vivo may contain sequences under the control of any RNA polymerase, including mitochondria! RNA polymerase, RNA pol I, RNA pol II, and RNA pol III, and viral polymerases, and bacteriophage polymerases such as T7 and Sp6. Desirably, expression vectors designed for in vivo expression of dsRNA effector molecules within a mammalian cell may be designed to utilize an endogenous mammalian polymerase such as an RNA polymerase I, RNA polymerase II, RNA polymerase III, and/or a mitochondrial polymerase. Expression vectors utilizing cognate promoter(s), e.g., polymerase III promoters such as U6, H1, or 7SK, in order to effect transcription by RNA polymerase III can readily be designed. Preferred for expression of short RNA molecules less than about 400 to 500 nucleotides in length are RNA polymerase III promoters. In some aspects, an "RNA polymerase III promoter" or "RNA pol III promoter" or "polymerase III promoter" or "pol III promoter" is preferred, meaning any invertebrate, vertebrate, or mammalian promoter, e.g., human, murine, porcine, bovine, primate, simian, etc. that, in its native context in a cell, associates or interacts with RNA polymerase III to transcribe its operably linked gene, or any variant thereof, natural or engineered, that will interact in a selected host cell with an RNA polymerase III to transcribe an operably linked nucleic acid sequence. Preferred in some applications are the Type III RNA pol III promoters including U6, H1, 7SK, and MRP which exist in the 5' flanking region, include TATA boxes, and lack internal promoter sequences. One reason RNA Pol III promoters are especially desirable for expression of small engineered RNA transcripts is that RNA Pol III termination, unlike RNA polymerase II termination, occurs efficiently and precisely at a short run of thymine residues in the DNA coding strand, without other protein factors, T4 and T5 being the shortest Pol III termination signals in yeast and mammals, with oligo (dT) terminators longer than T5 being very rare in mammals. Accordingly, the multiple polymerase III promoter expression constructs of the invention will include an appropriate oligo (dT) termination signal, i.e., a sequence of 4, 5, 6 or more Ts, operably linked 3' to each RNA Pol III promoter in the DNA coding strand.

These vectors can be used to transcribe the desired RNA molecule in the cell according to this invention. Vectors may be desirably designed to utilize an endogenous mitochondrial RNA polymerase (e.g., human mitochondrial RNA polymerase, in which case such vectors may utilize the corresponding human mitochondrial promoter). Mitochondria! polymerases may be used to generate capped (through expression of a capping enzyme) or uncapped messages in vivo. RNA pol I, RNA pol II, and RNA pol III transcripts may also be generated in vivo. Such RNAs may be capped or not, and if desired, cytoplasmic capping may be accomplished by various means including use of a capping enzyme such as a vaccinia capping enzyme or an alphavirus capping enzyme. However, all pol II transcripts are capped. The DNA vector is designed to contain one of the promoters or multiple promoters in combination (mitochondrial, RNA pol I, pol II, or pol III, or viral, bacterial or bacteriophage promoters along with the cognate polymerases). Preferably, where the promoter is RNA pol II, the sequence encoding the RNA molecule has an open reading frame greater than about 300 nts and must follow the rules of design to prevent nonsense-mediated degradation in the nucleus. Such plasmids or vectors can include plasmid sequences from bacteria, viruses or phages.

Such vectors include chromosomal, episomal and virus-derived vectors, e.g., vectors derived from bacterial plasmids, bacteriophages, yeast episomes, yeast chromosomal elements, and viruses, vectors derived from combinations thereof, such as those derived from plasmid and bacteriophage genetic elements, cosmids and phagemids.

Thus, one exemplary vector is a single or double-stranded phage vector. Another exemplary vector is a single or double-stranded RNA or DNA viral vector. Such vectors may be introduced into cells as polynucleotides, preferably DNA, by well known techniques for introducing DNA and RNA into cells. The vectors, in the case of phage and viral vectors may also be and preferably are introduced into cells as packaged or encapsidated virus by well known techniques for infection and transduction. Viral vectors may be replication competent or replication defective. In the latter case, viral propagation generally occurs only in complementing host cells.

In another embodiment the delivery agent comprises more than a single DNA or RNA plasmid or vector. As one example, a first DNA plasmid can provide a single stranded RNA sense polynucleotide sequence as described above, and a second DNA plasmid can provide a single stranded RNA anti-sense polynucleotide sequence as described above, wherein the sense and anti-sense RNA sequences have the ability to base-pair and become double-stranded. Such plasmid(s) can comprise other conventional plasmid sequences, e.g., bacterial sequences such as the well-known sequences used to construct plasmids and vectors for recombinant expression of a protein. However, it is desirable that the sequences which enable protein expression, e.g., Kozak regions, etc., are not included in these plasmid structures.

The vectors designed to produce dsRNAs of the invention may desirably be designed to generate two or more, including a number of different dsRNAs homologous and complementary to a target sequence. This approach is desirable in that a single vector may produce many, independently operative dsRNAs rather than a single dsRNA molecule from a single transcription unit and by producing a multiplicity of different dsRNAs, it is possible to self select for optimum effectiveness. Various means may be employed to achieve this, including autocatalytic sequences as well as sequences for cleavage to create random and/or predetermined splice sites.

Other delivery agents for providing the information necessary for formation of the above-described desired RNA molecules in the mammalian cell include live, attenuated or killed, inactivated recombinant bacteria which are designed to contain the sequences necessary for the required RNA molecules of this invention. Such recombinant bacterial cells, fungal cells and the like can be prepared by using conventional techniques such as described in U.S. Pat. Nos. 5,824,538; 5,877,159; and 5,643,771, incorporated herein by reference. Microorganisms useful in preparing these delivery agents include those listed in the above cited reference, including, without limitation, *Escherichia coli, Bacillus subtilis, Salmonella typhimurium*, and various species of *Pseudomonas, Streptomyces*, and *Staphylococcus.*

Still other delivery agents for providing the information necessary for formation of the desired, above-described RNA molecules in the mammalian cell include live, attenuated or killed, inactivated viruses, and particularly recombinant viruses carrying the required RNA polynucleotide sequence discussed above. Such viruses may be designed similarly to recombinant viruses presently used to deliver genes to cells for gene therapy and the like, but preferably do not have the ability to express a protein or functional fragment of a protein. Among useful viruses or viral sequences which may be manipulated to provide the required RNA molecule to the mammalian cell in vivo are, without limitation, alphavirus, adenovirus, adeno associated virus, baculoviruses, delta virus, pox viruses, hepatitis viruses, herpes viruses, papova viruses (such as SV40), poliovirus, pseudorabies viruses, retroviruses, lentiviruses, vaccinia viruses, positive and negative stranded RNA viruses, viroids, and virusoids, or portions thereof. These various viral delivery agents may be designed by applying conventional techniques such as described in M. Di Nocola et al., Cancer Gene Ther., 5(6):350-6 (1998), among others, with the teachings of the present invention.

The term “in vivo” is intended to include any system wherein the cellular DNA or RNA replication machinery is intact, preferably within intact living cells, including tissue culture systems, tissue explants, and within single cell or multicellular living organisms.

By “multiple sequitope dsRNA” or “multisequitope dsRNA” or “multiple epitope dsRNA” is meant an RNA molecule that has segments derived from multiple target nucleic acids or that has non-contiguous segments from the same target nucleic acid. For example, the multiple sequitope dsRNA may have segments derived from (i) sequences representing multiple genes of a single organism; (ii) sequences representing one or more genes from a variety of different organisms; and/or (iii) sequences representing different regions of a particular gene (e.g., one or more sequences from a promoter and one or more sequences from an mRNA. Desirably, each segment has substantial sequence identity to the corresponding region of a target nucleic acid. In various desirable embodiments, a segment with substantial sequence identity to the target nucleic acid is at least 19, 20, 21, 22, 23, 24, 25, 26, 27, 30, 40, 50, 100, 200, 500, 750, or more basepairs in length. In desirable embodiments, the multiple epitope dsRNA inhibits the expression of at least 2, 4, 6, 8, 10, 15, 20, or more target genes by at least 20, 40, 60, 80, 90, 95, or 100%. In some embodiments, the multiple epitope dsRNA has non-contiguous segments from the same target gene or from the same target polynucleotide that may or may not be in the naturally occurring 5' to 3' order of the segments, and the dsRNA inhibits the expression of the target nucleic acid by at least 50, 100, 200, 500, or 1000% more than a dsRNA with only one of the segments.

By “sequitope” is meant a contiguous sequence of double-stranded polyribonucleotides that can associate with and activate RISC (RNA-induced silencing complex), usually a contiguous sequence of between 19 and 27 basepairs, inclusive. Sequences comprising at least one sequitope from within one or more of the conserved HBV and/or HCV nucleotide sequences identified here may be utilized for dsRNA mediated gene silencing as taught herein.

Multiple-epitope/multiple-sequitope dsRNAs the advantages of a multiple-epitope or multisequitope double-stranded RNA approach as taught in U.S. Ser. No. 60/419,532, filed 18 Oct. 2002 and PCT/US2003/033466, filed 20 Oct. 2003, are applicable to utilization of the conserved HBV and/or HCV sequences of the invention. Because a singular species of dsRNA can simultaneously silence many target genes (e.g., genes from multiple pathogens, multiple genes or sequences from a single pathogen, or genes associated with multiple diseases), a multiple epitope dsRNA can be used for many different indications in the same subject or used for a subset of indications in one subject and another subset of indications in another subject. For such applications, the ability to express long dsRNA molecules (e.g., dsRNA molecules with sequences from multiple genes) without invoking the dsRNA stress response is highly desirable. For example, by using a series of sequences, each, e.g., as short as 19-21 nucleotides, desirably 100 to 600 nucleotides, or easily up to 1, 2, 3, 4, 5, or more kilobases such that the total length of such sequences is within the maximum capacity of the selected plasmid (e.g., 20 kilobases in length), a single such pharmaceutical composition can provide protection against a large number of pathogens and/or toxins at a relatively low cost and low toxicity, e.g., HBV, HCV, HIV, etc.

The use of multiple epitopes or sequitopes derived from one or more genes and/or different overlapping and/or non-contiguous sequences of the same polynucleotide or gene from multiple strains and/or variants of a highly variable or rapidly mutating pathogen such as HBV and/or HCV can also be very advantageous. For example, a singular dsRNA species that recognizes and targets multiple strains and/or variants of HBV and/or HCV can be used as a universal treatment or vaccine for the various strains/variants of HBV and/or HCV.

The ability to silence multiple genes of a particular pathogen such as HBV and/or HCV prevents the selection of, in this case, HBV and/or HCV "escape mutants." In contrast, typical small molecule treatment or vaccine therapy that only targets one gene or protein results in the selection of pathogens that have sustained mutations in the target gene or protein and the pathogen thus becomes resistant to the therapy. By simultaneously targeting a number of genes or sequences of the pathogen and/or extensive regions of the pathogen using the multiple epitope approach of the present invention, the emergence of such "escape mutants" is effectively precluded.

For example, it is considered particularly advantageous to include a mixture of sequences from both HCV SEQ ID NO:11 and SEQ ID NO:12, and SEQ ID NO: 27, i.e., one or more sequences (e.g, each at least 19, 20, 21, 22, 23, 24, 25, 26, 27 to 29 contiguous nucleotides) from HCV SEQ ID NO:11 together with one or more sequences (e.g, each at least 19, 20, 21, 22, 23, 24, 25, 26, 27 to 29 contiguous nucleotides) from HCV SEQ ID NO:12 and from SEQ ID NO: 27, either in a single dsRNA molecule, an admixture of dsRNA molecules, or through concomitant administration of such molecules to a patient (or by administering one or more dsRNA expression constructs which produce such dsRNA molecules intracellularly), in order to decrease the ability of the virus to generate viable escape mutants. Similarly, it would be advantageous to provide a mixture of dsRNA molecules comprising a number of the conserved HBV sequences, in some cases in combination with one or more of the conserved HCV sequences of the invention.

Similarly, it may be desirable to use sequences from two or more of HBV SEQ ID NO:1, SEQ ID NO:2, AND SEQ ID NO:3, either in a single dsRNA construct, an admixture of constructs, or through concomitant administration of such constructs (or dsRNA expression constructs which produce such dsRNA molecules) to a patient. SEQ ID NO:1, SEQ ID NO:2, and SEQ ID NO:3 map to the HBV surface antigen genes. Due to the overlapping nature of the HBV mRNAs, the following mRNAs would be targeted by one of more of these sequences: Surface Ag (sAg) mRNAs, precore, core and polymerase mRNAs. However, since sAg mRNAs are the most abundant, it is more likely that these mRNAs will be targeted if the gene-silencing machinery is saturable. It is possible, however, that all listed mRNAs will be targeted. Reduction of surface Ag is desirable for several reasons: a) surface Ag is needed for assembly of infectious virions; b) overexpression of Surface Ag during infection is thought to contribute to immune anergy that occurs during chronic HBV infection; and c) the expression of HBVsAg in the livers of infected individuals (even in the absence of virus, i.e., from integrated sAg sequences into the host genome) induces hepatitis. Therefore, reduction of sAg is likely to decrease viral titers, overcome immune anergy and decrease/prevent hepatitis.

HBV SEQ ID NO:4 maps to the unique region of precore and core and will target these mRNAs specifically. Core protein is needed to make functional virions and so down regulation of this mRNA is predicted to decrease viral titers. There should be no competition of these effector RNAs for surface, polymerase or X mRNAs.

HBV SEQ ID NO:5 through SEQ ID NO:8 map to the polymerase gene. Effector RNAs are predicted to target only precore/core and polymerase transcripts. There should be no competition with sAg or X mRNAs. Polymerase is needed for the synthesis of viral genomes and therefore viral particle titer is expected to decrease as polymerase is decreased.

HBV SEQ ID NO:9 maps to the X gene. Due to the terminal redundancy of all the HBV mRNAs, these effector RNAs have the potential to target all of the HBV viral mRNAs. X protein has many ascribed (non proven) functions. Evidence is emerging, however, that X-gene expression is associated with hepatocellular carcinogenesis, in part related to promotion of detachment and migration of cells out of the primary tumor site. Since the X gene is often found in integrated HBV sequences in individuals with and without active hepatitis, down-regulation of X gene expression is predicted to ameliorate disease, including the incidence of hepatocellular carcinoma.

In general, the more sequences or sequitopes from the different identified sequences that are used (e.g., from SEQ ID NO:1, SEQ ID NO:2, and/or SEQ ID NO:3, plus sequences from SEQ ID NO:4, SEQ ID NO:5, SEQ ID NO:6, SEQ ID NO:7, SEQ ID NO:8, SEQ ID NO:9, and SEQ ID NO:10), the less likely a virus will be able to generate viable escape mutants. Also, the more different mRNAs that can be targeted, the more significant will be the drops in viral titer and disease amelioration.

Desirable combinations for multiepitope or multisequitope dsRNA expression constructs or dsRNA effector molecules, an admixture of dsRNA expression constructs or dsRNA effector molecules, or the concomitant administration of different dsRNA expression constructs or dsRNA effector molecules include the following: Sequences from SEQ ID NO:1, SEQ ID NO:2, or SEQ ID NO:3 plus sequences from SEQ ID NO:4; Sequences from SEQ ID NO:1, SEQ ID NO:2, or SEQ ID NO:3 plus sequences from SEQ ID NO:5; Sequences from SEQ ID NO:1, SEQ ID NO:2, or SEQ ID NO:3 plus sequences from SEQ ID NO:6; Sequences from SEQ ID NO:1, SEQ ID NO:2, or SEQ ID NO:3 plus sequences from SEQ ID NO:7; Sequences from SEQ ID NO:1, SEQ ID NO:2, or SEQ ID NO:3 plus sequences from SEQ ID NO:8; Sequences from SEQ ID NO:1, SEQ ID NO:2, or SEQ ID NO:3 plus sequences from SEQ ID NO:9; Sequences from SEQ ID NO:1, SEQ ID NO:2, or SEQ ID NO:3 plus sequences from SEQ ID NO:10; Sequences from SEQ ID NO:1, SEQ ID NO:2, or SEQ ID NO:3 plus sequences from SEQ ID NO:4 and SEQ ID NO:5; Sequences from SEQ ID NO:1, SEQ ID NO:2, or SEQ ID NO:3 plus sequences from SEQ ID NO:4 and SEQ ID NO:6; Sequences from SEQ ID NO:1, SEQ ID NO:2, or SEQ ID NO:3 plus sequences from SEQ ID NO:4 and SEQ ID NO:7; Sequences from SEQ ID NO:1, SEQ ID NO:2, or SEQ ID NO:3 plus sequences from SEQ ID NO:4 and SEQ ID NO:8; Sequences from SEQ ID NO:1, SEQ ID NO:2, or SEQ ID NO:3 plus sequences from SEQ ID NO:4 and SEQ ID NO:9; Sequences from SEQ ID NO:1, SEQ ID NO:2, or SEQ ID NO:3 plus sequences from SEQ ID NO:4 and SEQ ID NO:10; Sequences from SEQ ID NO:1, SEQ ID NO:2, or SEQ ID NO:3 plus sequences from SEQ ID NO:5 and SEQ ID NO:6; Sequences from SEQ ID NO:1, SEQ ID NO:2, or SEQ ID NO:3 plus sequences from SEQ ID NO:5 and SEQ ID NO:7; Sequences from SEQ ID NO:1, SEQ ID NO:2, or SEQ ID NO:3 plus sequences from SEQ ID NO:5 and SEQ ID NO:8; Sequences from SEQ ID NO:1, SEQ ID NO:2, or SEQ ID NO:3 plus sequences from SEQ ID NO:5 and SEQ ID NO:9; Sequences from SEQ ID NO:1, SEQ ID NO:2, or SEQ ID NO:3 plus sequences from SEQ ID NO:5 and SEQ ID NO:10; Sequences from SEQ ID NO:1, SEQ ID NO:2, or SEQ ID NO:3 plus sequences from SEQ ID NO:6 and SEQ ID NO:7; Sequences from SEQ ID NO:1, SEQ ID NO:2, or SEQ ID NO:3 plus sequences from SEQ ID NO:6 and SEQ ID NO:8; Sequences from SEQ ID NO:1, SEQ ID NO:2, or SEQ ID NO:3 plus sequences from SEQ ID NO:6 and SEQ ID NO:9; Sequences from SEQ ID NO:1, SEQ ID NO:2, or SEQ ID NO:3 plus sequences from SEQ ID NO:6 and SEQ ID NO:10; Sequences from SEQ ID NO:1, SEQ ID NO:2, or SEQ ID NO:3 plus sequences from SEQ ID NO:7 and SEQ ID NO:8; Sequences from SEQ ID NO:1, SEQ ID NO:2, or SEQ ID NO:3 plus sequences from SEQ ID NO:7 and SEQ ID NO:9; Sequences from SEQ ID NO:1, SEQ ID NO:2, or SEQ ID NO:3 plus sequences from SEQ ID NO:7 and SEQ ID NO:10; Sequences from SEQ ID NO:1, SEQ ID NO:2, or SEQ ID NO:3 plus sequences from SEQ ID NO:8 and SEQ ID NO:9; Sequences from SEQ ID NO:1, SEQ ID NO:2, or SEQ ID NO:3 plus sequences from SEQ ID NO:8 and SEQ ID NO:10; Sequences from SEQ ID NO:1, SEQ ID NO:2, or SEQ ID NO:3 plus sequences from SEQ ID NO:9 and SEQ ID NO:10; Sequences from SEQ ID NO:4 and SEQ ID NO:5; Sequences from SEQ ID NO:4 and SEQ ID NO:6; Sequences from SEQ ID NO:4 and SEQ ID NO:7; Sequences from SEQ ID NO:4 and SEQ ID NO:8; Sequences from SEQ ID NO:4 and SEQ ID NO:9; Sequences from SEQ ID NO:4 and SEQ ID NO:10; Sequences from SEQ ID NO:5 and SEQ ID NO:6; Sequences from SEQ ID NO:5 and SEQ ID NO:7; Sequences from SEQ ID NO:5 and SEQ ID NO:8; Sequences from SEQ ID NO:5 and SEQ ID NO:9; Sequences from SEQ ID NO:5 and SEQ ID NO:10; Sequences from SEQ ID NO:6 and SEQ ID NO:7; Sequences from SEQ ID NO:6 and SEQ ID NO:8; Sequences from SEQ ID NO:6 and SEQ ID NO:9; Sequences from SEQ ID NO:6 and SEQ ID NO:10; Sequences from SEQ ID NO:7 and SEQ ID NO:8; Sequences from SEQ ID NO:7 and SEQ ID NO:9; Sequences from SEQ ID NO:7 and SEQ ID NO:10; Sequences from SEQ ID NO:8 and SEQ ID NO:9; Sequences from SEQ ID NO:8 and SEQ ID NO:10; Sequences from SEQ ID NO:9 and SEQ ID NO:10; Sequences from SEQ ID NO:4, SEQ ID NO:5; and SEQ ID NO:6; Sequences from SEQ ID NO:4, SEQ ID NO:5; and SEQ ID NO:7; Sequences from SEQ ID NO:4, SEQ ID NO:5; and SEQ ID NO:8; Sequences from SEQ ID NO:4, SEQ ID NO:5; and SEQ ID NO:9; Sequences from SEQ ID NO:4, SEQ ID NO:5; and SEQ ID NO:10; Sequences from SEQ ID NO:4, SEQ ID NO:6; and SEQ ID NO:7; Sequences from SEQ ID NO:4, SEQ ID NO:6; and SEQ ID NO:8; Sequences from SEQ ID NO:4, SEQ ID NO:6; and SEQ ID NO:9; Sequences from SEQ ID NO:4, SEQ ID NO:6; and SEQ ID NO:10; Sequences from SEQ ID NO:4, SEQ ID NO:7; and SEQ ID NO:8; Sequences from SEQ ID NO:4, SEQ ID NO:7; and SEQ ID NO:9; Sequences from SEQ ID NO:4, SEQ ID NO:7; and SEQ ID NO:10; Sequences from SEQ ID NO:4, SEQ ID NO:8; and SEQ ID NO:9; Sequences from SEQ ID NO:4, SEQ ID NO:8; and SEQ ID NO:10; Sequences from SEQ ID NO:4, SEQ ID NO:9; and SEQ ID NO:10; Sequences from SEQ ID NO:5, SEQ ID NO:6; and SEQ ID NO:7; Sequences from SEQ ID NO:5, SEQ ID NO:6; and SEQ ID NO:8; Sequences from SEQ ID NO:5, SEQ ID NO:6; and SEQ ID NO:9; Sequences from SEQ ID NO:5, SEQ ID NO:6; and SEQ ID NO:10; Sequences from SEQ ID NO:5, SEQ ID NO:7; and SEQ ID NO:8; Sequences from SEQ ID NO:5, SEQ ID NO:7; and SEQ ID NO:9; Sequences from SEQ ID NO:5, SEQ ID NO:7; and SEQ ID NO:10; Sequences from SEQ ID NO:5, SEQ ID NO:8; and SEQ ID NO:9; Sequences from SEQ ID NO:5, SEQ ID NO:8; and SEQ ID NO:10; Sequences from SEQ ID NO:5, SEQ ID NO:9; and SEQ ID NO:10; Sequences from SEQ ID NO:6, SEQ ID NO:7; and SEQ ID NO:8; Sequences from SEQ ID NO:6, SEQ ID NO:7; and SEQ ID NO:9; Sequences from SEQ ID NO:6, SEQ ID NO:7; and SEQ ID NO:10; Sequences from SEQ ID NO:6, SEQ ID NO:8; and SEQ ID NO:9; Sequences from SEQ ID NO:6, SEQ ID NO:8; and SEQ ID NO:10; Sequences from SEQ ID NO:6, SEQ ID NO:9; and SEQ ID NO:10; Sequences from SEQ ID NO:7, SEQ ID NO:8; and SEQ ID NO:9; Sequences from SEQ ID NO:7, SEQ ID NO:8; and SEQ ID NO:10; Sequences from SEQ ID NO:7, SEQ ID NO:9; and SEQ ID NO:10; Sequences from SEQ ID NO:8, SEQ ID NO:9; and SEQ ID NO:10; Sequences from SEQ ID NO:4, SEQ ID NO:5; SEQ ID NO:6; and SEQ ID NO:7; Sequences from SEQ ID NO:4, SEQ ID NO:5, SEQ ID NO:6, and SEQ ID NO:8; Sequences from SEQ ID NO:4, SEQ ID NO:5, SEQ ID NO:6, and SEQ ID NO:9; Sequences from SEQ ID NO:4, SEQ ID NO:5; SEQ ID NO:6; and SEQ ID NO:10; Sequences from SEQ ID NO:4, SEQ ID NO:5; SEQ ID NO:7; and SEQ ID NO:8; Sequences from SEQ ID NO:4, SEQ ID NO:5; SEQ ID NO:7; and SEQ ID NO:9; Sequences from SEQ ID NO:4, SEQ ID NO:5; SEQ ID NO:7; and SEQ ID NO:10; Sequences from SEQ ID NO:4, SEQ ID NO:5; SEQ ID NO:8; and SEQ ID NO:9; Sequences from SEQ ID NO:4, SEQ ID NO:5; SEQ ID NO:8; and SEQ ID NO:10; Sequences from SEQ ID NO:4, SEQ ID NO:5; SEQ ID NO:9; and SEQ ID NO:10; Sequences from SEQ ID NO:4, SEQ ID NO:6; SEQ ID NO:7; and SEQ ID NO:8; Sequences from SEQ ID NO:4, SEQ ID NO:6; SEQ ID NO:7; and SEQ ID NO:9; Sequences from SEQ ID NO:4, SEQ ID NO:6; SEQ ID NO:7; and SEQ ID NO:10; Sequences from SEQ ID NO:4, SEQ ID NO:7; SEQ ID NO:8; and SEQ ID NO:9; Sequences from SEQ ID NO:4, SEQ ID NO:7; SEQ ID NO:8; and SEQ ID NO:10; Sequences from SEQ ID NO:4, SEQ ID NO:7; SEQ ID NO:9; and SEQ ID NO:10; Sequences from SEQ ID NO:5, SEQ ID NO:6, SEQ ID NO:7, and SEQ ID NO:8; Sequences from SEQ ID NO:5, SEQ ID NO:6, SEQ ID NO:7, and SEQ ID NO:9; Sequences from SEQ ID NO:5, SEQ ID NO:6, SEQ ID NO:7, and SEQ ID NO:10; Sequences from SEQ ID NO:5, SEQ ID NO:6; SEQ ID NO:8; and SEQ ID NO:9; Sequences from SEQ ID NO:5, SEQ ID NO:6; SEQ ID NO:8; and SEQ ID NO:10; Sequences from SEQ ID NO:5, SEQ ID NO:6; SEQ ID NO:9; and SEQ ID NO:10; Sequences from SEQ ID NO:5, SEQ ID NO:7; SEQ ID NO:8; and SEQ ID NO:9; Sequences from SEQ ID NO:5, SEQ ID NO:7; SEQ ID NO:8; and SEQ ID NO:10; Sequences from SEQ ID NO:5, SEQ ID NO:7; SEQ ID NO:9; and SEQ ID NO:10; Sequences from SEQ ID NO:6, SEQ ID NO:7, SEQ ID NO:8, and SEQ ID NO:9;

Sequences from SEQ ID NO:6, SEQ ID NO:7, SEQ ID NO:8, and SEQ ID NO:10; Sequences from SEQ ID NO:6, SEQ ID NO:7, SEQ ID NO:9, and SEQ ID NO:10; Sequences from SEQ ID NO:6, SEQ ID NO:8, SEQ ID NO:9, and SEQ ID NO:10; Sequences from SEQ ID NO:4, SEQ ID NO:5, SEQ ID NO:6, SEQ ID NO:7, and SEQ ID NO:8; Sequences from SEQ ID NO:4, SEQ ID NO:5, SEQ ID NO:6, SEQ ID NO:7, and SEQ ID NO:9; Sequences from SEQ ID NO:4, SEQ ID NO:5, SEQ ID NO:6, SEQ ID NO:7, and SEQ ID NO:10; Sequences from SEQ ID NO:4, SEQ ID NO:5, SEQ ID NO:6, SEQ ID NO:8, and SEQ ID NO:9; Sequences from SEQ ID NO:4, SEQ ID NO:5, SEQ ID NO:6, SEQ ID NO:8, and SEQ ID NO:10; Sequences from SEQ ID NO:4, SEQ ID NO:5, SEQ ID NO:6, SEQ ID NO:9, and SEQ ID NO:10; Sequences from SEQ ID NO:4, SEQ ID NO:5, SEQ ID NO:7, SEQ ID NO:8, and SEQ ID NO:9; Sequences from SEQ ID NO:4, SEQ ID NO:5, SEQ ID NO:7, SEQ ID NO:8, and SEQ ID NO:10; Sequences from SEQ ID NO:4, SEQ ID NO:5, SEQ ID NO:7, SEQ ID NO:9, and SEQ ID NO:10; Sequences from SEQ ID NO:4, SEQ ID NO:6, SEQ ID NO:7, SEQ ID NO:8, and SEQ ID NO:9; Sequences from SEQ ID NO:4, SEQ ID NO:6, SEQ ID NO:7, SEQ ID NO:8, and SEQ ID NO:10; Sequences from SEQ ID NO:4, SEQ ID NO:6, SEQ ID NO:7, SEQ ID NO:9, and SEQ ID NO:10; Sequences from SEQ ID NO:5, SEQ ID NO:6, SEQ ID NO:7, SEQ ID NO:8, and SEQ ID NO:9; Sequences from SEQ ID NO:5, SEQ ID NO:6, SEQ ID NO:7, SEQ ID NO:8, and SEQ ID NO:10; Sequences from SEQ ID NO:5, SEQ ID NO:6, SEQ ID NO:7, SEQ ID NO:9, and SEQ ID NO:10; Sequences from SEQ ID NO:5, SEQ ID NO:6, SEQ ID NO:8, SEQ ID NO:9, and SEQ ID NO:10; Sequences from SEQ ID NO:5, SEQ ID NO:7, SEQ ID NO:8, SEQ ID NO:9, and SEQ ID NO:10; Sequences from SEQ ID NO:6, SEQ ID NO:7, SEQ ID NO:8, SEQ ID NO:9, and SEQ ID NO:10; Sequences from SEQ ID NO:4, SEQ ID NO:5, SEQ ID NO:6, SEQ ID NO:7, SEQ ID NO:8, and SEQ ID NO:9; Sequences from SEQ ID NO:4, SEQ ID NO:5, SEQ ID NO:6, SEQ ID NO:7, SEQ ID NO:8, and SEQ ID NO:10; Sequences from SEQ ID NO:4, SEQ ID NO:5, SEQ ID NO:6, SEQ ID NO:7, SEQ ID NO:9, and SEQ ID NO:10; Sequences from SEQ ID NO:4, SEQ ID NO:5, SEQ ID NO:6, SEQ ID NO:8, SEQ ID NO:9, and SEQ ID NO:10; Sequences from SEQ ID NO:4, SEQ ID NO:5, SEQ ID NO:7, SEQ ID NO:8, SEQ ID NO:9, and SEQ ID NO:10; Sequences from SEQ ID NO:4, SEQ ID NO:6, SEQ ID NO:7, SEQ ID NO:8, SEQ ID NO:9, and SEQ ID NO:10; Sequences from SEQ ID NO:5, SEQ ID NO:6, SEQ ID NO:7, SEQ ID NO:8, SEQ ID NO:9, and SEQ ID NO:10; and Sequences from SEQ ID NO:4, SEQ ID NO:5, SEQ ID NO:6, SEQ ID NO:7, SEQ ID NO:8, SEQ ID NO:9, and SEQ ID NO:10. Preferred in some aspects are sequences from SEQ ID NO:5, SEQ ID NO:6, SEQ ID NO:7, and SEQ ID NO:8, including combinations of sequitopes from SEQ ID NO:5, plus SEQ ID NO:6, plus SEQ ID NO:7, plus SEQ ID NO:8.

In another embodiment, combinations of sequitopes at least 19 contiguous base pairs in length and longer sequences from within any of the aforementioned sequences (e.g., SEQ ID NO:1 through SEQ ID NO:12) may be utilized either in a single dsRNA expression construct or dsRNA effector molecule, an admixture of dsRNA expression constructs or dsRNA effector molecules or through concomitant administration of such dsRNA expression constructs or dsRNA effector molecules to a patient. By a sequence of "at least 19 contiguous base pairs in length" is meant that a sequence or sequitope of at 19 contiguous bases in length is present in double-stranded conformation, or within a double-stranded RNA effector molecule.

As discussed elsewhere herein, a particularly preferred embodiment of the invention utilizes dsRNA expression constructs or vectors to achieve endogenous delivery of the dsRNAs of the invention, especially the multiple different sequences described above. These dsRNAs may be provided e.g., on the same cistron of an expression construct such as a plasmid, on different cistrons of an expression construct, or on different expression constructs or plasmids, e.g., one or more plasmids and/or one or more vectors, including viral vectors. The combination of different dsRNA effector molecules such as shRNA effector molecules may be provided to a mammalian cell by in vivo expression from a single expression construct such as a plasmid, with each dsRNA effector molecule transcribed from a different expression cassette driven by a different promoter, e.g., an RNA polymerase I promoter and/or an RNA polymerase III promoter, e.g., a type 3 RNA polymerase III promoter such as U6, H1, 7SK, or MRP. In some embodiments, each such different expression cassette may contain a different RNA polymerase III promoter, which may be the same or different, and an RNA polymerase III termination sequence. In another embodiment, a combination of different dsRNA effector molecules such as shRNA effector molecules may be provided to a mammalian cell by in vivo expression from a single expression construct such as a plasmid or a viral vector which comprise an expression cassette comprising multiple different promoters, e.g., an RNA polymerase I promoter and/or an RNA polymerase III promoter, e.g., a type 3 RNA polymerase III promoter such as U6, H1, 7SK, or MRP, and wherein each of such promoters transcribes a different dsRNA effector molecule. Such multiple different dsRNA effector sequences may also be provided to an in vivo mammalian cell exogenously, in any different mixture of one or more dsRNA structures, duplexes and/or harpins, and/or in combination with one or more endogenously expressed dsRNA structures.

Desirable methods of administration of nucleic acids The DNA and/or RNA constructs, e.g., dsRNA effector molecules, of the invention may be administered to the host cell/tissue/organism as "naked" DNA, RNA, or DNA/RNA, formulated in a pharmaceutical vehicle without any transfection promoting agent. More efficient delivery may be achieved as known to those of skill in the art of DNA and RNA delivery, using e.g., such polynucleotide transfection facilitating agents known to those of skill in the art of RNA and/or DNA delivery. The following are exemplary agents: cationic amphiphiles including local anesthetics such as bupivacaine, cationic lipids, liposomes or lipidic particles, polycations such as polylysine, branched, three-dimensional polycations such as dendrimers, carbohydrates, detergents, or surfactants, including benzylammonium surfactants such as benzalkonium chloride. Non-exclusive examples of such facilitating agents or co-agents useful in this invention are described in U.S. Pat. Nos. 5,593,972; 5,703,055; 5,739,118; 5,837,533; 5,962,482; 6,127,170; 6,379,965; and 6,482,804; and International Patent Application No. PCT/US98/22841; the teaching of which is hereby incorporated by reference. U.S. Pat. Nos. 5,824,538; 5,643,771; and 5,877,159 (incorporated herein by reference) teach delivery of a composition other than a polynucleotide composition, e.g., a transfected donor cell or a bacterium containing the dsRNA-encoding compositions of the invention.

In some embodiments, the dsRNA or dsRNA expression vector is complexed with one or more cationic lipids or cationic amphiphiles, such as the compositions disclosed in U.S. Pat. No. 4,897,355 (Eppstein et al., filed Oct. 29, 1987), U.S. Pat. No. 5,264,618 (Feigner et al., filed Apr. 16, 1991) or U.S. Pat. No. 5,459,127 (Feigner et al., filed Sep. 16, 1993). In other embodiments, the dsRNA or dsRNA expression vector is complexed with a liposome/liposomic composition that includes a cationic lipid and optionally includes another component such as a neutral lipid (see, for example, U.S. Pat. No. 5,279,833 (Rose), U.S. Pat. No. 5,283,185 (Epand), and U.S. Pat. No. 5,932,241).

Particularly desirable methods and compositions for delivery of the oligonucleotide compositions of the invention for pharmaceutical applications, including for targeted delivery to hepatocytes, are described in PCT/US03/14288, filed May 6, 2003, the teaching of which is incorporated herein by reference.

Transformation/transfection of the cell for research and other non-therapeutic purposes may occur through a variety of means including, but not limited to, lipofection, DEAE-dextran-mediated transfection, microinjection, calcium phosphate precipitation, viral or retroviral delivery, electroporation, or biolistic transformation. The RNA or RNA expression vector (DNA) may be naked RNA or DNA or local anesthetic complexed RNA or DNA (See U.S. Pat. Nos. 6,217,900 and 6,383,512, "Vesicular Complexes and Methods of Making and Using the Same, Pachuk et al., supra).

Another desirable delivery technology for the dsRNAs or dsRNA expression constructs of the invention for pharmaceutical applications is the self-assembling Cyclosert™ two-component nucleic acid delivery system, based on cyclodextrin-containing polycations, which are available from Insert Therapeutics, Pasadena, Calif. (See Bioconjug Chem 2003 May-June; 14 (3): 672-8; Popielarski et al.; "Structural effects of carbohydrate-containing polycations on gene delivery. 3. Cyclodextrin type and functionalization"; as well as Bioconjug Chem 2003 January-February; 14 (1): 247-54 and 255-61.) The first component is a linear, cyclodextrin-containing polycationic polymer, that when mixed with DNA, binds to the phosphate "backbone" of the nucleic acid, condensing the DNA and self assembling into uniform, colloidal nanoparticles that protect the DNA from nuclease degradation in serum. A second component is a surface modifying agent with a terminal adamantine-PEG molecule, that when combined with the cyclodextrin polymer forms an inclusion complex with surface cyclodextrins and prevents aggregation, enhances stability and enables systemic administration. In addition, targeting ligands to cell surface receptors may be attached to the modifier providing for targeted delivery of DNA directly to target cells of interest. Since hepatocytes are susceptible to HBV and HCV infection, utilizing this method to target delivery of the dsRNA expression constructs of the invention to liver cells is considered especially advantageous. E.g., the asialoglycoprotein receptor (ASGP-R) on mammalian hepatocytes may be targeted by use of synthetic ligands with galactosylated or lactosylated residues, such as galactosylated polymers.

In general, targeting for selective delivery of the dsRNA constructs of the invention to hepatocytes is preferred. Targeting to hepatocytes may be achieved by coupling to ligands for hepatocyte-specific receptors. For example, asialo-orosomucoid, (poly)L-lysine-asialo-orosomucoid, or any other ligands of the hepatic asialoglycoprotein receptor (Spiess, Biochemistry 29(43):10009-10018, 1990; Wu et al., J. Biol. Chem. 267(18):12436-12439, 1992; Wu et al., Biotherapy 3:87-95, 1991). Similarly, the oligonucleotides may be targeted to hepatocytes by being conjugated to monoclonal antibodies that specifically bind to hepatocyte-specific receptors. Oligonucleotides may also be targeted to hepatocytes using specific vectors, as described below.

Particularly preferred compositions for delivery of dsRNAs or dsRNA expression constructs of the invention are the multifunctional compositions as described in PCT/US03/14288, filed May 6, 2003, which may include trilactosyl spermine as a ligand for targeting to the ASG Receptor of hepatocytes. Trilactosyl cholesteryl spermine co-complexes with the oligonucleotides of the invention may be prepared and used as described to transfect hepatocytes in vivo.

The dsRNA oligonucleotides of the invention may be provided exogenously to a target hepatocyte, e.g., prepared outside the cell and delivered into a mammalian hepatocyte. Alternatively, a dsRNA may be produced within the target cell by transcription of a nucleic acid molecule comprising a promoter sequence operably linked to a sequence encoding the dsRNA. In this method, the nucleic acid molecule is contained within a non-replicating linear or circular DNA or RNA molecule, or is contained within an autonomously replicating plasmid or viral vector, or is integrated into the host genome. Any vector that can transfect a hepatocyte may be used in the methods of the invention. Preferred vectors are viral vectors, including those derived from replication-defective hepatitis viruses (e.g., HBV and HCV), retroviruses (see, e.g., WO89/07136; Rosenberg et al., N. Eng. J. Med. 323(9):570-578, 1990), adenovirus (see, e.g., Morsey et al., J. Cell. Biochem., Supp. 17E, 1993; Graham et al., in Murray, ed., Methods in Molecular Biology: Gene Transfer and Expression Protocols. Vol. 7, Clifton, N.J.: the Human Press 1991: 109-128), adeno-associated virus (Kotin et al., Proc. Natl. Acad. Sci. USA 87:2211-2215, 1990), replication defective herpes simplex viruses (HSV; Lu et al., Abstract, page 66, Abstracts of the Meeting on Gene Therapy, Sep. 22-26, 1992, Cold Spring Harbor Laboratory, Cold Spring Harbor, N.Y.), and any modified versions of these vectors. Methods for constructing expression vectors are well known in the art (see, e.g., Molecular Cloning: A Laboratory Manual, Sambrook et al., eds., Cold Spring Harbor Laboratory, 2nd Edition, Cold Spring Harbor, N.Y., 1989).

Appropriate regulatory sequences can be inserted into the vectors of the invention using methods known to those skilled in the art, for example, by homologous recombination (Graham et al., J. Gen. Virol. 36:59-72, 1977), or other appropriate methods (Molecular Cloning: A Laboratory Manual, Sambrook et al., eds., Cold Spring Harbor Laboratory, 2nd Edition, Cold Spring Harbor, N.Y., 1989).

Upon assembly of a recombinant DNA plasmid dsRNA expression vector on the invention, bacteria are used as "factories" to produce large quantities of the final vector. The *E. coli* bacterium is frequently used for plasmid fermentation, and it may be advantageous to employ for this purpose *E. coli* strains having a reduced genome as described in, e.g., Blattner et al., Published U.S. Patent Application No. 2005/0032225, the teaching of which is incorporated herein by reference. The vector manufactured in this manner, isolated and purified according to methods known in the art, can be introduced into living cells with a variety of methods, collectively known as "transfection", including the methods and compositions described above. Once inside the cell, the promoter elements are recognized by the cellular machinery available for gene transcription and the RNA effector molecules, e.g., shRNAs, will be produced.

Other bacterial strains that may be advantageous for propagating a plasmid expression vector of the invention include the *E. coli* GT116 Competent Cells available commercially from InvivoGen, San Diego, Calif. GT116 is a sbcCD deletion strain specifically engineered to support the growth of plasmid DNAs carrying hairpin structures, such as the plasmids of the invention engineered to express one or more dsRNA effector molecules which are hairpin RNAs. Hairpin structures are known to be unstable in *E. coli* due to their elimination by a protein complex called SbcCD that recognizes and cleaves hairpins (Connelly et al., Proc. Natl. Acad. Sci. USA 95:7969-74 (1998)). The sbcCD and sbcD genes are deleted in *E. coli* GT116, which improves its utility for cloning plasmids with hairpin or other palindrome-containing structures.

Promoters

Promoters are inserted into the vectors so that they are operably linked, typically but not invariably, 5' to the nucleic acid sequence encoding the dsRNA oligonucleotide. Any promoter that is capable of directing initiation of transcription in a eukaryotic cell may be used in the invention. For example, non-tissue-specific promoters, such as the cytomegalovirus (DeBernardi et al., Proc. Natl. Acad. Sci. USA 88:9257-9261, 1991, and references therein), mouse metallothionine I gene (Hammer, et al., J. Mol. Appl. Gen. 1:273-288, 1982), HSV thymidine kinase (McKnight, Cell 31:355-365 1982), and SV40 early (Benoist et al., Nature 290:304-310, 1981) promoters may be used. Non-tissue-specific promoters may be used in the invention, as expression of HBV and/or HCV dsRNA in non-liver cells directed by the non-tissue-specific promoters should be harmless to the non-liver cells, because of the specificity of the HBV and HCV dsRNAs of the invention for viral sequences. However, preferred promoters for use in the invention are hepatocyte-specific promoters, the use of which ensures that the RNAs are expressed primarily in hepatocytes. Preferred hepatocyte-specific promoters include, but are not limited to the albumin, alpha-fetoprotein, alpha-1-antitrypsin, retinol-binding protein, and asialoglycoprotein receptor promoters. Viral promoters and enhancers, such as those from cytomegalovirus, herpes simplex viruses (types I and II), hepatitis viruses (A, B, and C), and Rous sarcoma virus (RSV; Fang et al., Hepatology 10:781-787, 1989), may also be used in the invention.

dsRNA expression vectors may include promoters for RNA polymerase I, RNA polymerase II including but not limited to HCMV, SCMV, MCMV, RSV, EF2a, TK and other HSV promoters such as ICP6, ICP4 and ICP0 promoters, HBV pregenomic promoter, RNA pol III promoter, especially type 3 RNA polymerase III promoters, including but not limited to 7SK, U6, and H1, and tRNA promoters, as well as mitochondrial light and heavy strand promoters. Desirably, the dsRNA expression vector comprises at least one RNA polymerase II promoter, for example, a human CMV-immediate early promoter (HCMV-IE) or a simian CMV (SCMV) promoter, at least one RNA polymerase I promoter, or at least one RNA polymerase III promoter. The promoter may also be a T7 promoter, in which case, the cell further comprises T7 RNA polymerase. Alternatively, the promoter may be an SP6 promoter, in which case, the cell further comprises SP6 RNA polymerase. The promoter may also be one convergent T7 promoter and one convergent SP6 RNA promoter. A cell may be made to contain T7 or SP6 polymerase by transforming the cell with a T7 polymerase or an SP6 polymerase expression plasmid, respectively. In some embodiments, a T7 promoter or a RNA polymerase III promoter is operably linked to a nucleic acid that encodes a short dsRNA (e.g., a dsRNA that is less than 200, 150, 100, 75, 50, or 25 basepairs in length). In other embodiments, the promoter is a mitochondrial promoter that allows cytoplasmic transcription of the nucleic acid in the vector (see, for example, the mitochondria) promoters described in WO 00/63364, filed Apr. 19, 2000, and in WO/US2002/00543, filed 9 Jan. 2001). Alternatively, the promoter is an inducible promoter, such as a lac (Cronin et al. Genes & Development 15: 1506-1517, 2001), ara (Khlebnikov et al., J Bacteriol. 2000 December; 182(24):7029-34), ecdysone (Rheogene website), RU48 (mefepristone) (corticosteroid antagonist) (Wang X J, Liefer K M, Tsai S, O'Malley B W, Roop D R, Proc Natl Acad Sci USA. 1999 Jul. 20; 96(15):8483-8), or tet promoter (Rendal et al., Hum Gene Ther. 2002; 13(2): 335-42 and Larnartina et al., Hum Gene Ther. 2002; 13(2): 199-210) or a promoter disclosed in WO 00/63364, filed Apr. 19, 2000. Also useful in the methods and compositions of the invention are the structural and chimeric promoters taught in U.S. Ser. No. 60/464,434, filed 22 Apr. 2003. See also the promoter systems taught in Pachuk, C., and Satishchandran, C., "Multiple-Compartment Eurkaryotic Expression Systems," U.S. Provisional Application No. 60/497,304, filed 22 Aug. 2003, which are considered particularly desirable in the methods and compositions of the invention.

Liver specific promoters useful in dsRNA expression constructs of the invention include the albumin promoter, the alpha-fetoprotein promoter (especially in liver cancer cells), the alpha-1-antitrypsin promoter, hepatitis B promoters, e.g., hepatitis B promoters including promoters for the antigen genes, including core, e antigen, polymerase and X protein.

T7 Promoter/T7 Polymerase Expression Systems

A desirable method of the invention utilizes a T7 dsRNA expression system to achieve cytoplasmic expression of dsRNA, (e.g., long or short dsRNA molecules) in vertebrate cells (e.g., mammalian cells). The T7 expression system utilizes the T7 promoter to express the desired dsRNA. Transcription is driven by the T7 RNA polymerase, which can be provided on a second plasmid or on the same plasmid. Bacteriophage T7 RNA polymerase (T7 Pol) is the product of T7 gene 1, which can recognize its responsive promoter sequence specifically and exhibit a high transcriptase activity. The complete sequence of the T7 genome, with detailed information about the different regions of the bacteriophage, including promoter sequences, is disclosed in Dunn & Studier, 1983, J. Mol. Biol. 166(4), 477-535 (see also NCBI 'Genome' database, Accession No. NC 00 1 604). The T7 promoter cannot be utilised by any other RNA polymerase than the polymerase of bacteriophage T7, which shows a stringent specificity for the promoter (Chamberlin et al., 1970, Nature 228:227-231). When utilizing the T7 expression system for expressing dsRNAs, for example, a first plasmid construct that expresses both a sense and antisense strand under the control of converging T7 promoters and a second plasmid construct that expresses the T7 RNA polymerase under the control of an RSV promoter can be used. Both the dsRNA and the T7 RNA polymerase could advantageously be expressed from a single bicistronic plasmid construct, particularly when the dsRNA is formed from a single RNA strand with inverted repeats or regions of self-complementarity that enable the strand to assume a stem-loop or hairpin structure with an at least partially double stranded region. Individual sense and antisense strands which self assemble to form a dsRNA can be synthesized by a single plasmid construct using, e.g., converging promoters such as bacteriophage T7 promoters placed respectively at the 5' and 3' ends of the complementary strands of a selected sequence to be transcribed. See also, e.g., the teaching of WO 0063364, with respect to T7 dsRNA expression systems, as well as U.S. Ser. No. 60/399,998P, filed 31 Jul. 2002 and U.S. Ser. No. 60/419,532, filed 18 Oct. 2002.

Therapeutic Compositions of the Invention

The dsRNAs of the invention, and the recombinant vectors containing nucleic acid sequences encoding them, may be used in therapeutic compositions for preventing or treating HCV and/or HBV infection. The therapeutic compositions of the invention may be used alone or in admixture, or in chemical combination, with one or more materials, including other antiviral agents. Currently, lamivudine, adefovir dipivoxil, and interferon alpha have been approved for treatment of HBV, and it is anticipated that the compositions of the invention may be used in combination with these and other drugs that are active against HBV, including emtricitabine (FTC) and entecavir. Since dsRNAs against HBV and/or HCV act through a novel mechanism (dsRNA-mediated gene silencing/RNAi), combination therapy of the agents of the invention and other antivirals is expected to significantly increase the efficacy of therapy while substantially reducing the development of drug resistance, e.g., the development of lamivudine resistance, a problem of major concern with long term lamivudine therapy. Currently, interferon and ribavirin are licensed for treatment of HCV, and as for HBV, it is anticipated that the compositions of the invention may be used in combination with these and other drugs that are active against HCV. Specific dosage regimens involving therapy with such multiple agents can be determined through routine experimentation by those of ordinary skill in the art of clinical medicine.

Formulations will desirably include materials that increase the biological stability of the oligonucleotides or the recombinant vectors, or materials that increase the ability of the therapeutic compositions to penetrate hepatocytes selectively. The therapeutic compositions of the invention may be administered in pharmaceutically acceptable carriers (e.g., physiological saline), which are selected on the basis of the mode and route of administration, and standard pharmaceutical practice. One having ordinary skill in the art can readily formulate a pharmaceutical composition that comprises an oligonucleotide or a gene construct. In some cases, an isotonic formulation is used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. The pharmaceutical preparations according to the present invention are provided sterile and pyrogen free. Suitable pharmaceutical carriers, as well as pharmaceutical necessities for use in pharmaceutical formulations, are described in *Remington: The Science and Practice of Pharmacy* (formerly *Remington's Pharmaceutical Sciences*), Mack Publishing Co., a standard reference text in this field, and in the USP/NF.

Routes of administration include, but are not limited to, intramuscular, intraperitoneal, intradermal, subcutaneous, intravenous, intraarterially, intraoccularly and oral as well as transdermally or by inhalation or suppository. Preferred routes of administration include intravenous, intramuscular, oral, intraperitoneal, intradermal, intraarterial and subcutaneous injection.

Targeted transfection of hepatocytes in vivo for delivery of dsRNAs against HBV and/or HCV may be accomplished through IV injection with a composition comprising a DNA or RNA expression vector as described herein complexed with a mixture (e.g., a 35%/65% ratio) of a lactosyl spermine (mono or trilactosylated) and cholesteryl spermine (containing spermine to DNA at a charge ratio of 0.8). Such compositions are especially useful for pharmaceutical applications and may readily be formulated in a suitable sterile, non-pyrogenic vehicle, e.g., buffered saline for injection, for parenteral administration, e.g., IV (including IV infusion), IM, SC, and for intraperitoneal administration, as well as for aerosolized formulations for pulmonary delivery via inhalation. In certain formulations, a DNA expression construct of the invention may be complexed with an endosomolytic spermine such cholesteryl spermine alone, without a targeting spermine; some routes of administration, such as intraperitoneal injection or infusion, may achieve effective hepatic delivery and transfection of a DNA construct of the invention, and expression of RNA effector molecules, e.g., multiple dsRNA hairpins effective against HBV and/or HCV.

Intraperitoneal administration (e.g., ultrasound guided intraperitoneal injection) of a sterile pharmaceutical composition comprising dsRNA effector molecules and/or dsRNA expression constructs which provide dsRNA effector molecules against HBV and/or HCV in a specially formulated delivery vehicle may be an advantageous route of delivery to promote uptake by liver cells, including hepatocytes. In some compositions the dsRNA expression construct may be complexed with an appropriate transfection enhancing agent, e.g., with a mixture of a lactosyl spermine (mono or trilactosylated) and cholesteryl spermine, or in other compositions with an endosomolytic spermine such cholesteryl spermine alone, without a targeting spermine. The volume, concentration, and formulation of the pharmaceutical composition as well as the dosage regimen may be tailored specifically to maximize cellular delivery while minimizing toxicity such as an inflammatory response. E.g, relatively large volumes (5, 10, 20, 50 ml or more) with corresponding low concentrations of active ingredients, as well as the inclusion of an anti-inflammatory compound such as a corticosteroid, may be utilized if desired. Formulations as known to those of skill in the art of pharmaceutics may also be utilized to provide sustained release of dsRNA effector molecules and/or dsRNA expression constructs of the invention.

dsRNAs or dsRNA expression constructs may be administered by means including, but not limited to, traditional syringes, needleless injection devices, or "microprojectile bombardment gene guns". Intraperitoneal injection may be accomplished, e.g., with a traditional syringe, with placement of the needle advantageously guided by ultrasound or a similar technique. Alternatively, the dsRNA and/or dsRNA expression construct may be introduced by various means into cells that are removed from the individual. Such means include, for example, ex vivo transfection, electroporation, microinjection and microprojectile bombardment. After the gene construct is taken up by the cells, they are reimplanted into the individual. It is contemplated that otherwise non-immunogenic cells that have gene constructs incorporated therein can be implanted into the individual even if the host cells were originally taken from another individual.

In HBV infected individuals it is anticipated that the dsRNA compositions of the invention may be useful as a pre-treatment in conjunction with therapeutic vaccination protocols designed to boost immunity against the virus. It is also anticipated that the dsRNA compositions of the invention may be useful for prophylaxis in a regimen of periodic administrations to individuals who because of occupational or other potential for exposure are considered at high risk of exposure to HBV and/or HCV, e.g., fire, emergency, and health care personnel. Such an effective prophylactic regime may include administration of a composition that provides an HBV and/or HCV dsRNA of the invention, e.g., weekly, biweekly, monthly, bimonthly, every three months, every four months, semi-yearly, or yearly, as can be determined through routine experimentation by those of skill in the art of clinical medicine. The ability of a dsRNA expression vector such as a plasmid or viral vector to express the dsRNAs of the invention over a relatively prolonged period of time, expected to be in the range of weeks to months, is considered to be advantageous for this and other applications.

Dosage of dsRNAs

For administration of dsRNA (e.g., a short dsRNA to inhibit toxicity or a short or long dsRNA to silence a gene) to an animal, typically between 10 mg to 100 mg, 1 mg to 10 mg, 500 μg to 1 mg, or 5 μg to 500 μg dsRNA is administered to a 90-150 pound person/animal (in order of increasing preference). For administration of a vector encoding dsRNA (e.g., a short dsRNA to inhibit toxicity or a short or long dsRNA to silence a gene) to an animal, typically between 100 mg to 300 mg, 10 mg to 100 mg, 1 mg to 10 mg, 500 μg to 1 mg, or 50 μg to 500 μg dsRNA expression vector or construct is administered to a 90-150 pound person/animal (in order of increasing preference). The dose may be adjusted based on the weight of the animal. In some embodiments, about 1 to 10 mg/kg or about 2 to 2.5 mg/kg is administered. Other doses may also be used, as determined through routine experimentation by those of skill in the art of clinical medicine.

For administration in an intact animal, e.g., a human subject infected with HBV and/or HCV, between 1 mg and 100 mg, typically between 1 mg and 10 mg, between 10 ng and 50 μg, between 50 ng and 100 ng, or between 100 ng and 5 μg of dsRNA or DNA encoding one or more dsRNA effector molecules is used. In desirable embodiments, approximately 10 μg of a DNA or 5 μg of dsRNA is administered to the animal. In a desirable embodiment, a pharmaceutical composition for parenteral administration is prepared containing 10 mg of a plasmid dsRNA expression construct of the invention (in some formulations complexed with an appropriate transfection facilitating agent such as cholesteryl spermine or a mixture of cholesteryl spermine/trilactosyl spermine) in 25 ml of a suitable sterile vehicle for injection such as Normal Saline Injection, D5W, D5%/0.45% NaCl, D5%/0.2% NaCl, etc., and injected intraperitoneally over 5 to 10 minutes, with needle placement guided by untrasound or a similar technology. Administration may be repeated periodically, e.g., weekly or monthly, as required. With respect to the methods of the invention, it is not intended that the administration of dsRNA or DNA encoding dsRNA to cells or animals be limited to a particular mode of administration, dosage, or frequency of dosing; the present invention contemplates all modes of administration sufficient to provide a dose adequate to inhibit gene expression, prevent a disease, or treat a disease.

If desired, short dsRNA is delivered before, during, or after the exogenous delivery of dsRNA (e.g., a longer dsRNA) that might otherwise be expected to induce cytotoxicity. See the teaching of U.S. Ser. No. 10/425,006, filed 28 Apr. 2003, "Methods of Silencing Genes Without Inducing Toxicity", Pachuk.

Therapeutic Advantages of the Invention as it Relates to Worldwide Disease Incidence and Viral Variability The mutability of the hepatitis C virus genome, and to a lesser but significant extent, the hepatitis B virus genome, has been described above as presenting challenges to the design of nucleic acid based therapeutics against these viral agents. The inventors have painstakingly aligned thousands of individual HCV and HBV sequences, originally deriving from thousands of human viral isolates from widely divergent geographic areas worldwide. In doing so, the instant invention has identified and specified preferred sequences which are utilized singly and in combination in dsRNA effector molecules which target the least mutable regions of the genome of HCV and/or HBV.

The two-fold rationale for this has been discussed above, primarily in terms of ensuring that during the course of infection of a patient with HBV or HCV, the therapeutic of the invention will remain potent against the virus even as it mutates during the course of disease in a given patient. However, the second part of this rationale for deriving and using highly conserved sequences for design of dsRNA-¬based therapeutic applications, is that this also increases the certainty that the therapeutic dsRNA effector molecules of the invention, particularly the methods and compositions of the invention which utilize combinations of highly conserved sequences in dsRNA effector molecules against HBV and/or HCV, will be able to treat the viral infection present in individuals from a global variety of different ancestries, genetic makeup, and geographical distribution, which are known to manifest in clusters of viral variants based on such factors. Thus, a key feature of the therapeutic utility and novelty of this invention lies in the method of derivation of the preferred sequences and embodiments, and not simply in the demonstration that any particular HCV or HBV dsRNA sequence can inhibit viral replication of one or a few chosen viral isolates (or their cognate replicons) in a laboratory experiment, i.e., in a cell line or animal model, not necessarily reflective of the broad diversity of the HBV and/or HCV virus worldwide, or even in a particular infected individual over the course of infection.

For example, the hepatitis B virus has four subtypes of surface antigen, namely adw, ayw, adr and ayr. While lamivudine is considered an effective therapy for chronic Hepatitis B, a recent study of HBV resistance demonstrated a 20-fold increase in resistance in the adw subtype, compared to the ayw subtype. B Zollner et al. "20-fold Increase in Risk of Lamivudine [Epivir HBV] Resistance in Hepatitis B Virus Subtype adw"; *The Lancet*. 2001; 357: 934-935. In contrast to such conventional antiviral agents, the dsRNA agents of the invention, (e.g., dsRNA effector molecules and expression constructs of the invention, especially when used in combination as taught herein) which utilize HBV and/or HCV sequences highly conserved across such geographical genetic variants are expected to exhibit highly advantageous antiviral activity.

Similarly, HCV is also known for having a wide range of geographically divergent viral genotypes, subtypes, quasispecies, with the following current general global patterns of genotypes and subtypes:

1a—mostly found in North & South America; also common in Australia 1 b—mostly found in Europe and Asia.

2a—is the most common genotype 2 in Japan and China.

2b—is the most common genotype 2 in the US and Northern Europe.

2c—the most common genotype 2 in Western and Southern Europe.

3a—highly prevalent here in Australia (40% of cases) and South Asia.

4a—highly prevalent in Egypt

4c—highly prevalent in Central Africa

5a—highly prevalent only in South Africa

6a—restricted to Hong Kong, Macau and Vietnam 7a and 7b—common in Thailand
8a, 8b & 9a—prevalent in Vietnam
10a & 11a—found in Indonesia Accordingly, the highly conserved sequences of the invention, which are expected to be conserved among most if not all of these divergent HCV genotypes and subtypes worldwide, including 1a, 1b, 2a, 2b, and 2c, are considered highly effective therapeutics agents, e.g., when utilized as dsRNA effector molecules, especially combinations thereof, and dsRNA expression vectors capable of expressing such dsRNAs.

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

The following Examples are provided as illustrative only. All references mentioned within this disclosure are specifically incorporated herein by reference in their entirety.

Example 1

Silencing HBV Replication and Expression in a Replication Competent Cell Culture Model Brief description of cell culture model: A human liver-derived cell line such as the Huh7 cell line is transfected with an infectious molecular clone of HBV consisting of a terminally redundant viral genome that is capable of transcribing all of the viral RNAs and producing infectious virus [1-3]. The replicon used in these studies is derived from the virus sequence found in Gen Bank Accession V01460. Following internalization into hepatocytes and nuclear localization, transcription of the infectious HBV plasmid from several viral promoters has been shown to initiate a cascade of events that mirror HBV replication. These events include translation of transcribed viral mRNAs, packaging of transcribed pregenomic RNA into core particles, reverse transcription of pregenomic RNA, and assembly and secretion of virions and HBsAg (Hepatitis B Surface Antigen) particles into the media of transfected cells. This transfection model reproduces most aspects of HBV replication within infected liver cells and is therefore a good cell culture model with which to look at silencing of HBV expression and replication.

Using this model, cells were co-transfected with the infectious molecular clone of HBV and various eiRNA constructs (dsRNA expression constructs). The cells were then monitored for loss of HBV expression and replication as described below. Details on the vector and encoded RNAs used in this experiment are provided at the end of this example.

Experiment 1

The following is an example of an experiment that was performed using eiRNA vectors (dsRNA expression vectors) encoding sequences derived from GenBank accession number V01460. HBV sequences in these described eiRNA vectors were highly conserved sequences identified as described elsewhere herein, which also exhibited activity as siRNAs (See, Pachuk, C., "Methods and Constructs for Evaluation of RNAi targets and Effector Molecules," PCT/US2004/005065, filed 25 Feb. 2004). The particular eiRNA backbone vector used for this experiment was a proprietary vector containing a U6 promoter to drive expression of the encoded RNAs. Each vector. encoded only one short hairpin RNA (shRNA). The shRNA coding sequence was followed by an RNA pol III termination sequence. Sequences of the U6 promoter, RNA pol In termination signal, and encoded shRNAs are all shown at the end of the example. Similar vectors containing U6 promoters and RNA pol III termination signals are commercially available such as the "siLentGene-2 Cloning Systems" vector from Promega, Inc., Madison, Wis. One of ordinary skill in the art can also create them according to the information provided herein. It is expected that similar results would also be obtained using other expression and promoter systems especially those vectors with RNA pol III promoters that are not U6, for example H1 promoters or 7SK promoters.

Experimental Procedure: Transfection

Huh7 cells cultured in RPMI-1640 media were seeded into six-well plates at a density of $3\times10^5$ cells/well. All transfections were performed the day after cell seeding using Lipofectamine™ (InVitrogen, Carlsbad, Calif.) according to the manufacturer's directions. In this experiment, cells were transfected with 500 ng of the infectious HBV plasmid ayw subtype ("pHBV2") (GenBank Accession #V01460) and 500 ng, 300 ng, 250 ng, 120 ng, 100 ng, 50 ng, or 10 ng of an eiRNA construct. DNA was held constant/transfection at 2.5 μg by including an inert plasmid DNA, pGL3-Basic (Promega, Madison Wis.) in amounts that brought the total DNA in the transfection to 2.5 μg. For example, in transfections receiving 500 ng of HBV DNA and 500 ng of an eiRNA construct, 1.5 μg pGL3 was added to the transfection. Prior to transfection, media was removed from the cells and the cells washed with Opti-MEM® (InVitrogen Life Technologies, Carlsbad, Calif.). 800 μl of Opti-MEM® was then added to each well of cells followed by the addition of the transfection mix. Seventeen to nineteen hours post-transfection, the transfection mix and Opti-MEM® were removed from cells and replaced with 2 mL culture media/well. At 3, 6, and 10 days after transfection, the media was removed from cells and stored at −70° C. The media was replaced with 2 mL of fresh culture media on days 3 and 6. All transfections were carried out in duplicate. Two sets of control transfections were also performed: HBV DNA alone (500 ng HBV DNA plus 2 μg pGL3) and HBV DNA with a control eiRNA construct (500 ng HBV DNA, 1 μg control eiRNA construct, and 1.0 μg pGL3 DNA).

Monitoring Cells for Loss of HBV Expression.

Following transfection, cells were monitored for the loss or reduction in HBV expression and replication by measuring HBsAg secretion. Cells were monitored by assaying the media of transfected cells (and a media control) at days 3, 6, and 10 post-transfection. The Auszyme® ELISA, commercially available from Abbott Labs (Abbott Park, III.), was used to detect surface Ag (sAg) according to the manufacturer's instructions. sAg was measured since surface Ag is associated not only with viral replication but also with RNA polymerase II initiated transcription of the surface Ag cistron in the transfected infectious HBV clone and from HBVcccDNA produced during infection in vivo. Since surface Ag synthesis can continue with deleterious effects in the absence of HBV replication, it is important to down-regulate not only viral replication but also replication-independent synthesis of sAg.

Results:

Cells transfected with the HBV-specific eiRNA constructs described at the end of this example all induced a decrease in sAg levels relative to the controls. The level inhibition is shown in the accompanying FIG. 2-8 corresponding to data found in Tables 2-8. Note that the sequences identified as 788-808 and 807-827 only lowered surface Ag levels by 30% and 50% respectively at 500 ng doses. These are the only two eiRNAs that do not target the sAg mRNA; instead they target the 3.1 Kb HBV mRNAs and therefore reduce sAg levels indirectly. The 30% to 50% reduction in sAg observed when these other HBV RNAs are targeted is considered a strong indication that these eiRNA constructs are efficacious.

HBV-Specific eiRNAs Used in this Experiment

The eiRNA vectors encode the HBV sequences listed in Table 1. The sequences are shown as well as their map coordinates on GenBank accession number V01460. At the rightmost part of the table is the SEQ ID NO that these sequences map within. The sequence of the encoded RNA is 5'GGTCGAC (a sequence that is per se unimportant, but is derived from the polylinker sequence of the particular vector used) followed by a first sense or antisense HBV sequence followed by the loop sequence (underlined in Table 1) followed by a second HBV sequence, which is the complement to the first HBV sequence. Note that the loop structure does not need to be a fixed sequence or length, and we have used several loop sequences with no significant impact on the functioning of the eiRNA construct. The second HBV sequence is followed by a string of T residues, e.g., 1, 2, 3, or more Ts, that function as the termination signal for RNA pol III.

TABLE 1

| HBV-AYW coordi-nates* | SEQ ID NO | | Maps within SEQ ID NO |
|---|---|---|---|
| 788-708 | 14 | CGTCTGCGAGGCGAGGGAGTTAGAGAACT TAACTCCCTCGCCTCGCAGACG | 5, 6, 7, or 8 |
| 807-827 | 15 | TTCTTCTTCTAGGGGACCTGCAGAGAACT TGCAGGTCCCCTAGAAGAAGAA | 5, 6, 7, or 8 |
| 1291-1311 | 16 | AAGCCACCCAAGGCACAGCTTAGAGAACT TAAGCTGTGCCTTGGGTGGCTT | 4 |
| 1299-1319 | 17 | CAAGGCACAGCTTGGAGGCTTAGAGAACT TAAGCCTCCAAGCTGTGCCTTG | 4 |
| 1737-1757 | 18 | GGATTCAGCGCCGACGGGACGAGAGAACT TCGTCCCGTCGGCGCTGAATCC | 10 |
| 1907-1927 | 19 | TTCCGCAGTATGGATCGGCAGAGAGAACT TCTGCCGATCCATACTGCGGAA | 3 |
| 1912-1932 | 20 | CAGTATGGATCGGCAGAGGAGAGAGAACT TCTCCTCTGCCGATCCATACTG | 3 |
| 1943-1963 | 21 | TCCACGCATGCGCTGATGGCCAGAGAACT TGGCCATCAGCGCATGCGTGGA | 3 |
| 1991-2011 | 22 | TGCGTCAGCAAACACTTGGCAAGAGAACT TTGCCAAGTGTTTGCTGACGCA | 3 |
| 2791-2811 | 23 | AAAACGCCGCAGACACATCCAAGAGAACT TTGGATGTGTCTGCGGCGTTTT | 2 |
| 2791-2811mut | 24 | AAAACACCACACACGCATCCAAGAGAACT TTGGATGCGTGTGTGGTGTTTT | 2 |
| 2912-2932 | 25 | TTGAGAGAAGTCCACCACGAGAGAGAACT TCTCGTGGTGGACTTCTCTCAA | 1 |
| 2919-2939 | 26 | AAGTCCACCACGAGTCTAGACAGAGAACT TGTCTAGACTCGTGGTGGACTT | 1 |
| 799-779 | 49 | GCCTCGCAGACGAAGGTCTCAAGAGAACT TTGAGACCTTCGTCTGCGAGGC | |

*nucleotide coordinates refer to Genbank accession number V01460.

Figure 9:
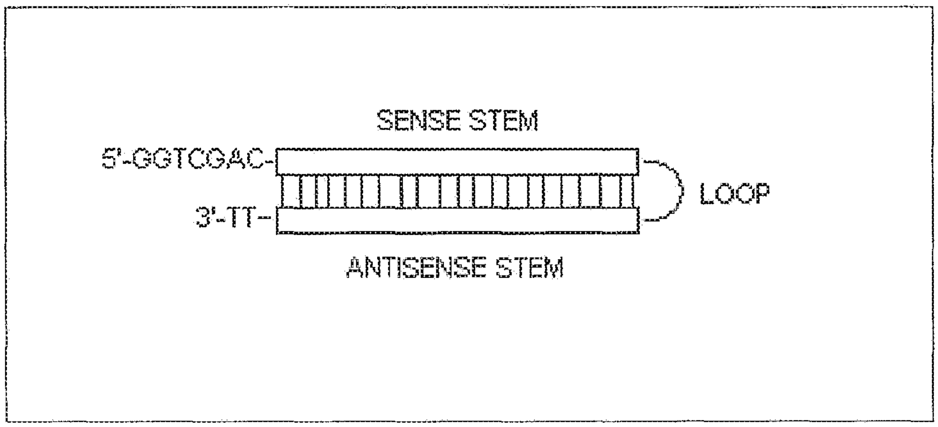
FIG. 9 is a drawing depicting effective HBV-AYW shRNA inserts.

A diagram of the transcribed RNA structure is shown in FIG. 9.

SEQ ID NO:13 is the nucleotide sequence of U6 promoter. Nucleotide sequence of RNA pol III terminator: 5'-TTTTT-3'.

The HBV sequitopes of Table 1 (without their respective complement sequence and without the "loop" or linker sequence utilized in a "hairpin" or stem-loop dsRNA effector molecule) are shown in Table 1A below. Each such HBV sequitope, together with its complementary sequence, optionally with an appropriate loop or linker sequence as taught herein, may be utilized in a dsRNA effector molecule of the invention (e.g., a duplex dsRNA or hairpin dsRNA effector molecule, or encoded within a dsRNA expression vector). In one aspect, multiple (e.g., 2, 3, 4, 5, 6, or more) of such dsRNA short hairpin effector molecules are encoded in a single expression vector, e.g., a plasmid expression vector, each under the control of a different promoter, e.g., a polymerase III promoter, as described elsewhere herein.

TABLE 1A

| HBV-AYW coordinates Genbank accession number V01460* | SEQ ID NO | Conserved HBV Sequitope | Maps within SEQ ID NO |
|---|---|---|---|
| 788-808 | 50 | CGTCTGCGAGGCGAGGGAGTT | 5, 6, 7, or 8 |
| 807-827 | 51 | TTCTTCTTCTAGGGGACCTGC | 5, 6, 7, or 8 |
| 1291-1311 | 52 | AAGCCACCCAAGGCACAGCTT | 4 |
| 1299 = 1319 | 53 | CAAGGCACAGCTTGGAGGCTT | 4 |
| 1737-1757 | 54 | GGATTCAGCGCCGACGGGACG | 10 |
| 1907-1927 | 55 | TTCCGCAGTATGGATCGGCAG | 3 |
| 1912-1932 | 56 | CAGTATGGATCGGCAGAGGAG | 3 |

TABLE 1A-continued

| HBV-AYW coordinates Genbank accession number V01460* | SEQ ID NO | Conserved HBV Sequitope | Maps within SEQ ID NO |
|---|---|---|---|
| 1943-1963 | 57 | TCCACGCATGCGCTGATGGCC | 3 |
| 1991-2011 | 58 | TGCGTCAGCAAACACTTGGCA | 3 |
| 2791-2811 | 59 | AAAACGCCGCAGACACATCCA | 2 |
| 2912-2932 | 60 | TTGAGAGAAGTCCACCACGAG | 1 |
| 2919-2939 | 61 | AAGTCCACCACGAGTCTAGAC | 1 |
| 799-779 | 62 | GCCTCGCAGACGAAGGTCTCA | |

Tables and Graphs.

HBsAg was measured as described above and plotted in FIG. 2-8 corresponding to the data in Tables 2-8. The amount of eiRNA construct is shown in parentheses following the name of the eiRNA construct and is in μg amounts. For example, 2791(0.5) means that 0.5 μg or 500 ng of eiRNA construct 2791-2811 (see Table 1) was used in the transfection. The percent inhibition relative to the control is also shown in the tables below and it is specific for the day 10 measurement. Note that the $4^{th}$ set of data in this example in which 1299 was evaluated at 500 ng has only two timepoints, days 3 and 6, because the evaluation was not carried out at day 10. The percent inhibition for this experiment was shown for day 6 data. Data is shown as raw OD data collected as described by the manufacturer of the Auszyme ELISA assay kit used to measure sAg. Not shown are the 50 ng data for 2791-2811 and the 10 ng data for 1907-1927. Each of these doses inhibited HBsAg expression by about 50% relative to the control.

TABLE 2

| | Day 3 | Day 6 | Day 10 | % Inhibition relative to control |
|---|---|---|---|---|
| pHBV2 | 0.339 | 1.88 | 3.268 | — |
| 2791(0.5) | 0.101 | 0.263 | 0.333 | 89.8 |

TABLE 3

| | Day 3 | Day 6 | Day 10 | % Inhibition relative to control |
|---|---|---|---|---|
| pHBV2 | 1.169 | 4.445 | 10.18 | — |
| 2791 (0.5) | 0.442 | 0.743 | 1.3 | 87.2 |
| 2791Mut (0.5) | 1.136 | 4.305 | 10.595 | — |

TABLE 4

| | Day 3 | Day 6 | Day 10 | % Inhibition relative to control |
|---|---|---|---|---|
| pHBV2 | 0.375 | 1.952 | 4.005 | — |
| 2791mut (1) | 0.421 | 1.847 | 4.753 | — |
| HCV (1) | 0.445 | 1.805 | 3.933 | — |

TABLE 4-continued

| | Day 3 | Day 6 | Day 10 | % Inhibition relative to control |
|---|---|---|---|---|
| 788 (0.5) | 0.255 | 1.195 | 2.778 | 30.6 |
| 807 (0.5) | 0.254 | 1.326 | 2.015 | 49.7 |
| 1907 (0.25) | 0.052 | 0.113 | 0.365 | 90.9 |
| 1912 (0.25) | 0.138 | 0.208 | 0.517 | 87.1 |
| 1943 (0.25) | 0.099 | 0.233 | 0.506 | 87.4 |
| 1991 (0.25) | 0.075 | 0.152 | 0.291 | 92.7 |
| 2912 (0.25) | 0.095 | 0.183 | 0.331 | 91.7 |

TABLE 5

| | Day 3 | Day 6 | % Inhibition relative to control |
|---|---|---|---|
| pHBV2 | 0.474 | 1.513 | — |
| 1299 (0.5) | 0.439 | 0.699 | 53.8 |

TABLE 6

| | Day 3 | Day 6 | Day 10 | % Inhibition relative to control |
|---|---|---|---|---|
| pHBV2 | 0.33 | 1.617 | 2.88 | — |
| 2791 (0.3) | 0.103 | 0.192 | 0.349 | 87.9 |
| 1737 (0.3) | 0.051 | 0.094 | 0.232 | 91.9 |
| 1291 (0.12) | 0.239 | 0.587 | 1.195 | 58.5 |
| 1907 (0.12) | 0.043 | 0.086 | 0.356 | 87.6 |
| 2919 (0.12) | 0.218 | 0.565 | 1.09 | 62.2 |

TABLE 7

| | Day 3 | Day 6 | Day 10 | % Inhibition relative to control |
|---|---|---|---|---|
| pHBV2 | 0.741 | 2.53 | 5.383 | — |
| 2791 (0.3) | 0.223 | 0.256 | 0.458 | 91.5 |
| 1737 (0.1) | 0.212 | 0.351 | 0.549 | 89.8 |
| 1907 (0.1) | 0.067 | 0.149 | 0.468 | 91.3 |
| 1991 (0.1) | 0.067 | 0.16 | 0.345 | 93.6 |

TABLE 8

| | Day 3 | Day 6 | Day 10 | % Inhibition relative to control |
|---|---|---|---|---|
| pHBV2 | 0.864 | 4.414 | 8.344 | — |
| 1907 (0.05) | 0.17 | 0.538 | 1.396 | 83.3 |
| 2919 (0.1) | 0.368 | 1.044 | 1.908 | 77.1 |
| 1291 (0.2) | 0.573 | 1.654 | 1.896 | 77.3 |

Experiment 2

Background: The same cell culture model was used to evaluate the additive effects of adding two eiRNA constructs. In this experiment 2791-2811 and 2919-2939 were evaluated. They were evaluated separately at two doses: 10 ng and 25 ng, and in combination at 10 ng (5 ng of 2791-2811 plus 5 ng of 2919-2939) and at 25 ng (12.5 ng 2791-2811 plus 12.5 ng 2919-2939). An additive effect is observed, for example, when half the inhibition seen with 25 ng 2791-2811 plus half the inhibition seen with 25 ng 2919-2939 is about equal to the inhibition seen of the 25 ng combination dose. This is important because while one may not be gaining inhibition over the use of a single eiRNA construct at the 25 ng dose, the use of two or more eiRNA sequences is very important in preventing the generation of viral escape mutants.

Experimental Procedure: Transfection

Huh7 cells were seeded into six-well plates at a density of $3\times10^5$ cells/well. All transfections were performed the day after cell seeding using Lipofectamine™ (InVitrogen) according to the manufacturer's directions. In this experiment, cells were transfected with 500 ng of the infectious HBV plasmid ayw subtype (GenBank Accession #V01460) and 25 ng or 10 ng of two separate eiRNA constructs or a combination of these two eiRNA constructs at a total of 25 ng or 10 ng. DNA was held constant/transfection at 2.5 μg by including an inert plasmid DNA, pGL3, in amounts that brought the total DNA in the transfection to 2.5 μg. For example, in transfections receiving 500 ng of HBV DNA and 10 ng of an eiRNA construct, then 1.99 μg pLUC was added to the transfection. Prior to transfection, media was removed from the cells and the cells washed with Opti-MEM® (InVitrogen Life Technologies). 800 μl of Opti-MEM® was then added to each well of cells followed by the addition of the transfection mix. Seventeen to nineteen hours post-transfection, the transfection mix and Opti-MEM® was removed from cells and replaced with 2 mL culture media/well. At 4, 8, and 11 days after transfection, the media was removed from cells and stored at −70° C. The media was replaced with 2 mL of fresh culture media on days 4 and 8. All transfections were carried out in duplicate. Two sets of control transfections were also performed: HBV DNA alone (500 ng HBV DNA plus 2 μg pGL3), and HBV DNA with a control eiRNA construct (500 ng HBV DNA, 500 ng control eiRNA construct and 1.5 μg pGL3. DNA).

Figure 10:
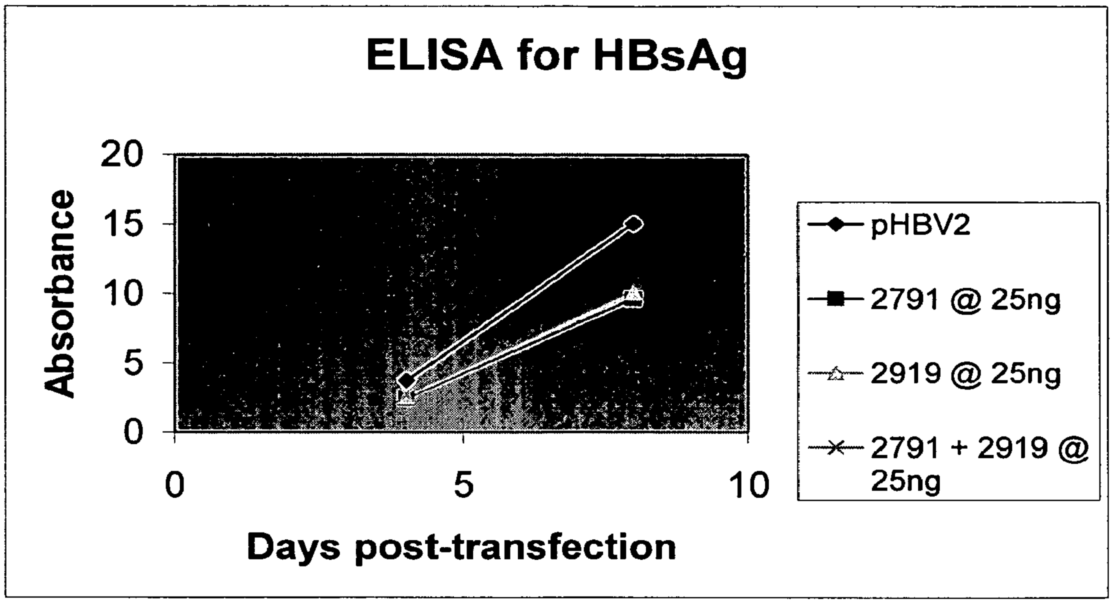
FIG. 10 is a graph showing HBsAg inhibition corresponding to data found in Table 9.

Results:

Results are shown in Table 9, and the corresponding graph found in FIG. 10. Combining 2791-2811 and 2919-2939 showed at least equal effects to administration of 2791-2811 or 2919-2939 alone. It is expected that similar advantages will be seen by combining two or more dsRNAs directed to different HBV sequences from the same and/or different HBV genes.

TABLE 9

| | Day 4 | Day 8 |
|---|---|---|
| $pHBV_2$ | 3.74 | 15.03 |
| 2791 @ 25 ng | 2.49 | 9.63 |
| 2919 @ 25 ng | 2.55 | 10.07 |
| 2791 + 2919 @ 25 ng | 2.73 | 10.91 |

Experiments 3 and 4

Silencing of HBV in a Mouse Model.

Summary: Two of the eiRNA vectors described in confirmatory experiment 1 were assessed for their ability to silence an HBV replicon in a mouse model. These vectors were the 2791-2811 and the 1907-1927 vectors. Both vectors were found to silence HBV in the mouse model to a similar extent as they silenced in the cell culture model. The ability to silence this HBV replicon in mice by other therapeutics has been demonstrated to be a predictor of human efficacy [4].

Animal Model Background:

Chimpanzees represent the only animal model in which to study human HBV infectivity. A mouse model is available, however, in which HBV expression and replication occur. This model has been invaluable for the evaluation of anti-HBV therapeutic agents not only targeted against viral replication but also against RT-independent expression of antigen. In this model, replication competent HBV is expressed transiently from episomal HBV DNA. This model is created by introducing replication competent HBV DNA into mouse liver by hydrodynamic delivery [1].

The aim of the following experiment was to test two of the vectors encoding HBV-specific sequences evaluated in Experiment 1 for efficacy in a mouse model even though there were not expected to be HBV-sequence-related efficiency differences between the cell culture and mouse models. This experiment utilized hydrodynamic delivery as a method to co-deliver replication competent HBVayw plasmid (Example 1, confirmatory experiment 1) with an effector HBV-specific eiRNA expression vector. Hydrodynamic delivery is ideal for these first studies because it results in efficient delivery of nucleic acid to the liver [5].

Experiments

Hydrodynamic Delivery Studies: Experiment 3

All animals were hydrodynamically injected with 7.5 pg infectious HBVayw plasmid (described in confirmatory Example 1). Following internalization into hepatocytes and nuclear localization, transcription of HBVayw plasmid from several viral promoters has been shown to initiate a cascade of events that mirror HBV replication [1]. These events include translation of transcribed viral mRNAs, packaging of transcribed pregenomic RNA into core particles, reverse transcription of pregenomic RNA, and assembly and secretion of virions and HBsAg particles into the sera of injected animals. Experimental animals were co-injected with 10 μg 2791-2811. A second group of control animals were injected with 10 pg of an irrelevant eiRNA construct. All animals were also co-injected with 2.5 μg of a GFP reporter plasmid (Clontech, Palo Alto, Calif.). Expression of GFP mRNA in the livers of injected mice served as a control to normalize results against the mouse model transfection efficiency. Total DNA injected in animals was kept at a constant 20 μg by including pGL3, an inert filler DNA (Promega, Madison, Wis.). All DNA was formulated and injected according to the methods described in Yang et al. [1]. There were 5 animals per group. The DNAs and amounts of DNA injected per animal are shown in Table 10.

TABLE 10

| Group | HBV DNA | GFP DNA | eiRNA | pGL3 |
|---|---|---|---|---|
| 1 | 7.5 μg | 2.5 μg | 10 μg 2791 | 0 μg |
| 2 | 7.5 μg | 2.5 μg | 10 μg control | 0 μg |
| 3 | 7.5 μg | 2.5 μg | 0 μg | 10 μg |

Timepoints of analysis were selected based on published results from Dr. Chisari's laboratory [1], which detail the kinetics of HBVayw plasmid replication in mice following hydrodynamic delivery. Serum was assayed for the presence of HBsAg on days 1, 2, 3, and 4 post-injection. Assays were performed as described for the cell culture model of HBV replication. The presence of HBV RNA in liver samples was ascertained by Northern blot analysis on day 2 following injection using procedures developed in Dr. Chisari's laboratory [1] and normalized to endogenous GAPDH RNA levels and GFP mRNA levels using conventional techniques, or a quantitative RT-PCR assay for HBV RNAs containing sAg coding sequences using standard techniques. RT-PCR is more quantitative than Northern Blot analysis and has a larger dynamic window than does Northern Blot analysis.

Figure 11:
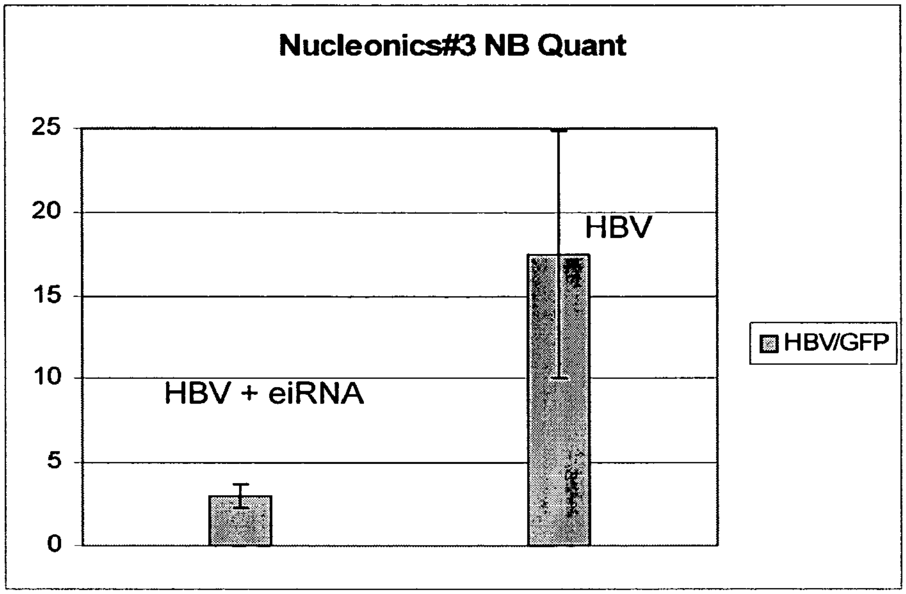
FIG. 11 is a bar graph showing downregulation of HBV RNA by Northern Blot analysis.
Figure 12:
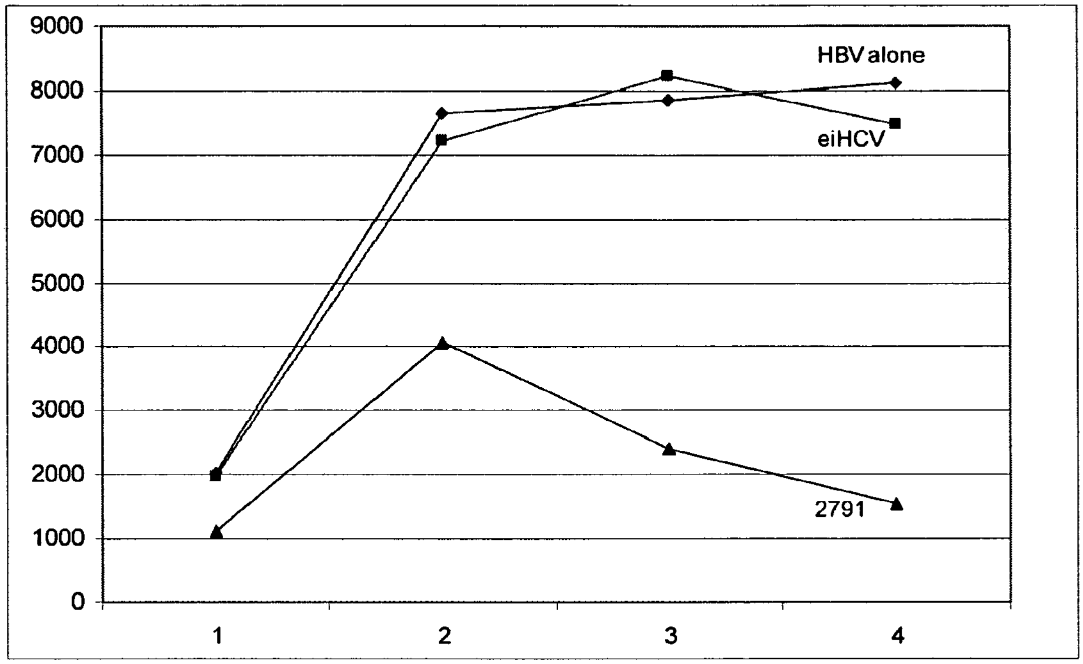
FIG. 12 is a graph showing HBsAg inhibition corresponding to data found in Table 12.

Downregulation of both HBV RNA by Northern Blot analysis and HBsAg were seen in mice injected with 2791-2811. See FIG. 11. Also not shown, quantitative RT-PCR demonstrated the presence of 867 HBV RNA molecules in the livers of control mice and 57 molecules of HBV RNA in 2791-2811 treated mice, a 15-fold downregulation.

TABLE 13

| NUC6_HBsAg | | HBsAG (ng/ml) d1 | HBsAG (ng/ml) d4 |
|---|---|---|---|
| HBV | 2 | 6147 | 36,953 |
| | 3 | 6234 | 42,542 |
| | 4 | 4658 | 33,061 |
| | 5 | 5077 | 29,389 |
| | grp ave=> | 5529 | 35486 |
| | Std Dev=> | 784 | 5627 |
| eiHCV | 6 | 1901 | 11,236 |
| | 7 | 6286^ | 29,637^ |
| | 8 | 1023 | 6,345 |
| | grp ave=> | 3070 | 15739 |
| | Std Dev=> | 2820 | 12282 |
| 2791 | 11 | 3966 | 5009 |
| | 13 | 4705 | 7347^ |
| | 14 | 2289 | 4538 |
| | 15 | 2427 | 4217 |
| | grp ave=> | 3347 | 5278 |
| | Std Dev=> | 1182 | 1417 |
| 1907 | 16 | 4954 | 7203^ |
| | 18 | 2982 | 6917^ |
| | 19 | 3436 | 7568^ |
| | 20 | 2246 | 5135^ |
| | grp ave=> | 3405 | 6706 |
| | Std Dev=> | 1143 | 1081 |

TABLE 11

| Group | Mouse | 3.5 kb | 2.1 kb | GFP | HBV total | HBV/GFP | Group Average | Std. Dev |
|---|---|---|---|---|---|---|---|---|
| 10 μg | 1 | 182360 | 1440614 | 4044344 | 1622974 | 4.0 | 3.0 | 0.76 |
| 2791 | 2 | 392294 | 3161703 | 9954889 | 3553997 | 3.6 | | |
| | 3 | 268673 | 3114347 | 15317275 | 3383020 | 2.2 | | |
| | 4 | 394799 | 3909096 | 16806285 | 4303895 | 2.6 | | |
| | 5 | 362182 | 4439430 | 18306755 | 4801612 | 2.6 | | |
| HBV | 21 | 2412562 | 8720964 | 3860082 | 11133526 | 28.8 | 17.4 | 7.40 |
| only | 22 | 2170741 | 7958388 | 6110744 | 10129129 | 16.6 | | |
| | 23 | 2713213 | 12060855 | 9633404 | 14774068 | 15.3 | | |
| | 24 | 1924373 | 7243024 | 11042915 | 9167397 | 8.3 | | |
| | 25 | 1464641 | 5726217 | 3968243 | 7190858 | 18.1 | | |

TABLE 12

| NUC5_HBsAg | | HBsAG (ng/ml) d1 | d2 | d3 | d4 |
|---|---|---|---|---|---|
| HBV | 2 | 2810 | 6793 | 8422 | 8517 |
| | 3 | 2344 | 8332 | 8089 | 8743 |
| | 4 | 1684 | 8788 | 9064 | 8876 |
| | 5 | 2318 | 9378 | 8597 | 8480 |
| | 29 | 1066 | 5038 | 5153 | 5925 |
| | grp ave=> | 2044 | 7666 | 7865 | 8108 |
| | Std Dev=> | 678 | 1754 | 1556 | 1231 |
| eiHCV | 6 | 2554 | 8048 | 9233 | 8870 |
| | 9 | 2267 | 8420 | 9535 | 8338 |
| | 10 | 1704 | 8258 | 8761 | 7840 |
| | 30 | 1362 | 4171 | 5406 | 4920 |
| | grp ave=> | 1972 | 7224 | 8234 | 7492 |
| | Std Dev=> | 538 | 2041 | 1912 | 1765 |
| 2791 | 11 | 1262 | 2823 | 2276 | 2080 |
| | 12 | 1222 | 2549 | 2858 | 1593 |
| | 14 | 1056 | 1933 | 1143 | 792 |
| | 15 | 1275 | 8320 | 1920 | 2068 |
| | 27 | 779 | 4771 | 3782 | 1252 |
| | grp ave=> | 1119 | 4079 | 2396 | 1557 |
| | Std Dev=> | 209 | 2598 | 993 | 551 |

Hydrodynamic Delivery Studies: Experiment 4

This experiment was similar to the Experiment 3 of Example 1 except that two eiRNA constructs were evaluated: 2791-2811 and 1907-1927. In this experiment, HBsAg was measured on days 1 and 4 using the assay already described herein.

A Four-Promoter RNA Polymerase III-Based Expression Construct for Production of shRNAs which Reduce Hepatitis B RNA Production and Replication.

As described in more detail in PCT/US05/29976 filed 23 Aug. 2005, a plasmid expression vector, pHB4, containing 4 polymerase III promoter short hairpin dsRNA expression cassettes was constructed. Each expression cassette included a polymerase III promoter operably linked to a sequence encoding a short hairpin dsRNA, and a polymerase III termination sequence. The polymerase III promoters were U6, 7SK, and two copies of a 7SK sequence variant promoter, designated 7SK-4A. Each short hairpin dsRNA sequence comprised a double-stranded stem region homologous and complementary to a highly conserved HBV sequence as taught herein. The four dsRNA effector molecules comprised the sequences of SEQ ID NO: 49; SEQ ID NO: 23; SEQ ID NO:19; and SEQ ID NO: 18; which comprise, respectively; the sequences of SEQ ID NO: 62; SEQ ID NO: 59; SEQ ID NO:55; and SEQ ID NO: 54. As described in more detail in Example 1 of PCT/US05/29976, however, the sequence encoding the dsRNA hairpin effector molecule was inserted into an expression cassette of the plasmid expression vector at a restriction site which in effect resulted in several additional nucleotides being added to the 5' end of the ultimate transcript. The predicted transcript which includes the dsRNA hairpin actually contains additional 5' and 3' sequences: a 5' leader consisting of 6 bases (e.g., the Sal I or Hind III or other chosen recognition sequence), followed by the dsRNA hairpin sequences, followed by a short 3' terminal U tract, usually two (1, 2, 3, or 4) U residues incorporated during transcription termination. These differences in length and composition of 5' and 3' transcript sequences flanking the dsRNA hairpin did not appear to adversely affect the ability of the dsRNA hairpin to effect dsRNA-mediated silencing, which suggests that, unlike synthetic dsRNA duplexes, endogenously expressed dsRNA hairpin constructs are effective despite varying in a number of respects, e.g., length of dsRNA "stem" between about 19-29 bp, length and composition of single-stranded loop, presence or absence of additional short 5' and/or 3' sequences.

A luciferase assay as taught in Example 1 of PCT/US05/29976 and in WO 04/076629, published 10 Sep. 2004, "Methods and Constructs for Evaluation of RNAi Targets and Effector Molecules" indicated that all 4 promoter/shRNA cassettes were active in silencing their target sequences in a cell supplied with the vector and an assayable substrate. The IC50 value decreased substantially when increasing from a one promoter/shRNA cassette vector to the pHB4 expression vector containing 4 promoter/shRNA cassettes. The 1050 values may have also been affected by the relative potency and transcription levels of each shRNA molecule, and did not reflect a simple relationship to the concentration of the vector only, which in effect behaved as four drugs after entering the cell and expressing the four encoded dsRNA molecules. In other words, the increased potency reflected not only the greater number of total shRNA transcripts generated by the vector, but the also the individual potency that each shRNA has to effect the reduction of sAg or eAg production via degradation of the target viral RNA molecules. The progressive addition of shRNA cassettes increased the potency of the vector in an apparently quantitative manner, and furthermore increased the pharmacological activity against the HBV target by inhibiting four distinct sites of the HBV target. It is important to recognize, however, that the ability of the multiple polymerase III expression constructs to express multiple individual antiviral dsRNA hairpin molecules is of significant value in and of itself, not just because of associated increases in "potency". Where the level of antiviral efficacy is high, the incremental quantitative increase in viral inhibition seen with each additional dsRNA molecule may be less important per se than the ability of the constructs to deliver what is in effect a multi-drug regimen, with the inherent advantage of being highly resistant to the development of viral resistance.

The expression vectors, designed to deliver multiple dsRNA effector molecules targeting highly conserved HBV and/or HCV polynucleotide sequences, when delivered to a virally infected cell, have the unique ability to destroy the viral nucleic acid products directly. Moreover, inherent and integral to the design and intent of these multiple promoter vectors (which express a plurality of different inhibitory short hairpin dsRNAs targeting different portions of the viral genome), is the property of generating multiple different viral antagonists simultaneously. The antagonists (short hairpin dsRNA effector molecules) target different genome sequences in the viral genome. One of these antagonists would probably be sufficient to disable the virus; however, the redundancy serves as a "backup" mechanism such that if the viral sequence mutates to render one antagonist inert, there are 2, 3, 4 or more additional antagonists available. Additionally, by targeting multiple sites in the viral genome, different DNA or RNA products of the virus which play different roles in the disease pathology can be attacked at the same time.

In the case of Hepatitis B for example, in one embodiment, the instant invention uses 4, 5, or more shRNA molecules selected from the following sequences and other highly conserved HBV sequences as taught herein: e.g., "799" (SEQ ID No. 49); "1907" (SEQ ID No. 19); "2791" (SEQ ID No. 23); "1737" (SEQ ID No. 18), "1991" (SEQ ID No. 22), "1943" (SEQ ID No. 21). Other of the conserved HBV sequences disclosed herein, including sequences of e.g., 19 to 29 nucleotides, which comprise all or part of "799", "1907", "2791", "1737", "1991", or "1943", may be selected for inclusion in dsRNA hairpin effector molecules to be expressed by expression vectors comprising multiple promoters, including multiple polymerase III expression vectors. Due to the nature of HBV gene expression and overlapping transcriptional products this allows targeting of multiple RNA transcripts as well as the replicative template of the virus which will interfere with replication and expression of more than one of the viral proteins. One of the shRNA molecules, "1737" (SEQ ID No. 18) uniquely can disable the RNA encoding a product known as the X protein (HbX). Strong evidence exists in the biomedical literature that the X protein plays a role in establishment and/or maintenance of liver cancer. Because the existing drugs that can to some extent inhibit viral replication cannot eliminate the cell of integrated or other residual copies or portions of the viral genome, these drugs cannot shut off the production of HbX, even in patients "cured" of infectious HBV, and thus can not directly reduce any incidence of cancer that is mediated by dormant HbX. Multiple anti-HBV dsRNA hairpin expression constructs of the present invention can attack both the replication of the virus and the expression of all viral proteins, some which cause the inflammatory insult which results in hepatitis, and others such as HbX, which are believed to promote hepatocellular carcinoma via a distinct but not fully understood mechanism. It is recognized that the principles taught herein can be used to design constructs of the invention specifically tailored to treat such "post infection" patients, which express dsRNAs against Hbx and any other residual HBV antigens.

While the HBV target sequences of the invention were chosen expressly to represent those highly conserved or identical among a large number of different isolates (strains) of HBV, for reference purposes the identified sequences, e.g., shRNA sequences, can be mapped back to HBV isolate AYW. It should be recognized, therefore, that the dsRNAs and dsRNA expression constructs of the invention are expected to be effective not only against HBV AYW and related viral strains, but against nearly all if not all HBV strains encountered in infected human populations in widely dispersed geographical areas.

Example 2

Hepatitis C— Sequences for RNAi Therapeutic Development

Experiment 1

Brief Introduction

The hepatitis C virus (HCV) is the primary cause of non-A, non-B transfusion-associated hepatitis and accounts for more than 200 million hepatitis cases worldwide. The HCV genome has a high degree of sequence variability. There are six major genotypes comprising more than fifty subtypes and significant heterogeneity hallmarked by quasi-species has been found within patients. Great progress in understanding HCV replication has been made by using recombinant polymerases or cell-based subgenomic replicon systems. By using a replicon cell system, HCV-specific siRNA has been demonstrated to be able to suppress HCV protein expression and RNA replication. Sequences of the 5' NTR and both structural and nonstructural genes have been targeted successfully. The highly conserved nature of the 3' NTR sequence makes it a highly attractive target for siRNA based therapy. However, no study has been done to examine the feasibility of using the 3' NTR. Here we report the design and testing of several siRNAs that can inhibit HCV protein expression in the subgenomic replicon system. Exogenously synthesized HCV-specific siRNAs were transfected into the HCV replicon cell line as described below.

Cell Culture and Media:

The HCV replicon in hepatoma Huh7 cells was cultured in Dulbecco's Modified Eagle Media ("DMEM") (Invitrogen) containing 10% fetal calf serum (Invitrogen), 1% penicillin-streptomycin, 1% non-essential amino acids and 0.5 mg/mL Geneticin. Cells were grown to 75% confluency prior to splitting.

Western Blot Analysis:

Total cell lysates from replicon cells were harvested from replicon cells in 1×LDS Buffer (Invitrogen). The lysates were heated at 90° C. for 5 min in the presence of beta-mercaptoethanol before electrophoresis on a 10% Tris-Glycine polyacrylamide gel (Invitrogen). The protein was transferred to PVDF (Invitrogen) membrane. Following the transfer, the membrane was rinsed once with PBS containing 0.5% Tween-20 (PBS Tween) and blocked in PBS-Tween containing 5% non-fat milk for 1 hr. After washing with PBS-Tween, the membrane was incubated with the primary α-NS5A antibody (a gift from Dr. Chen Liu) at 1:1500 dilution for 1 hr at room temperature. Prior to incubation with HRP conjugated a-mouse IgG secondary antibody (Amersham) diluted 1:5000, the blot was washed in PBS-Tween 20. Following the secondary antibody incubation, the blot was washed again and treated with ECL (Amersham) according to the manufacturer's protocol.

Northern Blot:

Total cellular RNA was extracted by using the Rneasy® kit (Qiagen). Northern blot analysis was done according to the protocol of Guo et al. Briefly, 5 μg total RNA was electrophoresed through a 1.0% agarose gel containing 2.2 M formaldehyde, transferred to a nylon membrane and immobilized by UV cross-linking (Stratagene). Hybridization was carried out using α[$^{32}$P]CTP-labeled neomycin RNA in a solution containing 50% deionized formamide, 5×SSC (750 mM sodium chloride, 750 mM sodium citrate), Denhardt's solution, 0.02 M sodium phosphate (pH 6.8), 0.2% sodium dodecyl sulfate ("SDS"), 100 μg of sheared denatured salmon sperm DNA/ml, and 100 pg of yeast RNA/ml, for 16 hr at 58° C. The membranes were washed once in 2×SSC/0.1% SDS for 30 min at room temperature and twice in 0.1×SSC/0.1% SDS for 30 min at 68° C. Membranes were exposed to X-ray film.

Transfection of siRNA into Replicon Cells:

For transfection of siRNA into replicon cells the Lipofectamine® 2000 reagent (Invitrogen) was used according to the user manual. Briefly, 2×10$^4$ cells in 0.5 mL of DMEM was seeded in 24 well plates one day before the transfection. The indicated amount of siRNA was diluted in 50 μL OptiMEM and mixed with diluted Lipofectamine® 2000 reagent (1 μL in 50 μL of Optimem). The mixture was incubated at room temperature for 20 min before being applied onto the cell monolayer. 48-72 hr after transfection, cells were washed in PBS and lysed in 100 μL. SDS sample buffer.

TABLE 14

| siRNA number | SEQ ID NO | HCV sequence |
|---|---|---|
| #12 | 28 | GCTAAACACTCCAGGCCAATACCTGTCTC |
| #22 | 29 | TCCTTTGGTGGCTCCATCTTACCTGTCTC |
| #32 | 30 | GCTCCATCTTAGCCCTAGTCACCTGTCTC |
| #42 | 31 | TCTTAGCCCTAGTCACGGCTACCTGTCTC |
| #52 | 32 | CCTAGTCACGGCTAGCTGTGACCTGTCTC |
| #62 | 33 | CTAGTCACGGCTAGCTGTGAACCTGTCTC |
| #72 | 34 | CGTGAGCCGCTTGACTGCAGACCTGTCTC |
| #82 | 35 | GCTGATACTGGCCTCTCTGCACCTGTCTC |
| #102 | 36 | ACTGGCCTCTCTGCAGATCAACCTGTCTC |

Several short duplex dsRNAs comprising the HCV sequences identified above in Table 14 (in each case, the first 21 bases constitute conserved HCV sequences of the invention, followed by an 8-base "adapter" sequence, "CCTGTCTC", appended from the Ambion kit used in synthesis, but which do not appear in the dsRNA effector molecules) targeting the 3'UTR; siRNA #12 targeting the HCV NS5B gene (positive control); the identified HCV core siRNA (positive control); and the identified lamin siRNA (negative control) were synthesized using the Silencer siRNA construction kit, Catalog #1620 (Ambion Inc., Austin, Tex.). DNA oligonucleotides were synthesized by IDT (Coralville, Iowa).

TABLE 14A

| siRNA number | SEQ ID NO | HCV sequence |
|---|---|---|
| #12 | 63 | GCTAAACACTCCAGGCCAATA |
| #22 | 64 | TCCTTTGGTGGCTCCATCTTA |
| #32 | 65 | GCTCCATCTTAGCCCTAGTCA |
| #42 | 66 | TCTTAGCCCTAGTCACGGCTA |
| #52 | 67 | CCTAGTCACGGCTAGCTGTGA |
| #62 | 58 | CTAGTCACGGCTAGCTGTGAA |

TABLE 14A-continued

| siRNA number | SEQ ID NO | HCV sequence |
|---|---|---|
| #72 | 69 | CGTGAGCCGCTTGACTGCAGA |
| #82 | 70 | GCTGATACTGGCCTCTCTGCA |
| #102 | 71 | ACTGGCCTCTCTGCAGATCAA |

Several siRNAs comprising the HCV sequences identified above in Table 14 targeting the 3'UTR; siRNA #12 targeting the HCV NS5B gene (positive control); the identified HCV core siRNA (positive control); and the identified lamin siRNA (negative control) were synthesized using the Silencer siRNA construction kit, Catalog #1620 (Ambion Inc., Austin, Tex.). DNA oligonucleotides were synthesized by IDT (Coralville, Iowa).

Control siRNAs:

1. HCV core (positive control): SEQ ID NO:45
2. #12, shown in Table 14, targeting the HCV NS5B gene, also a positive control
3. lamin sequence (negative control): SEQ ID NO:46

Figure 13:
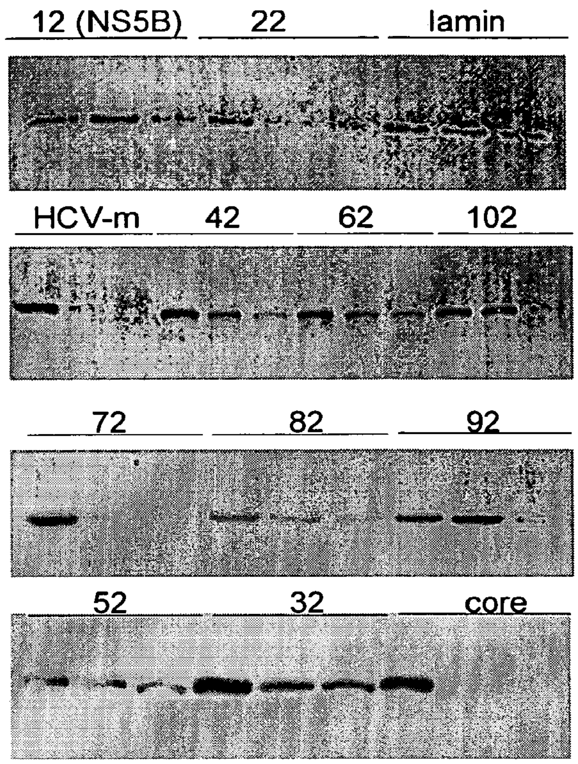
FIG. 13 is a Western Blot showing levels of HCV NS5A protein at (1 to r) 0, 9, and 20 pmole of the identified siRNAs, as described in more detail in Experiment 1 of Example 2.

Three siRNAs were used as controls: siRNA targeting the cellular gene Lamin for negative control; siRNA targeting the core sequence of HCV as a positive control; siRNA targeting the HCV NS5B gene as a positive control. Two concentrations of each siRNA (9 and 20 pmole) were used and the results were compared with transfection of no siRNA. Accordingly, the Western Blots in FIG. 13 represent 0, 9, and 20 pmoles of the identified siRNAs. siRNA #22, 32, 42, 62, and 72 were notably active in repressing HCV NS5A protein expression. Presumably, HCV RNA level is also decreased based on the results obtained previously with positive control siRNA for core. Several siRNAs had minimum effect at the concentrations tested and should be evaluated at higher concentrations. These include #12 (targeting NS5B), #102, #52, and #82.

Experiment 2

Figure 14:
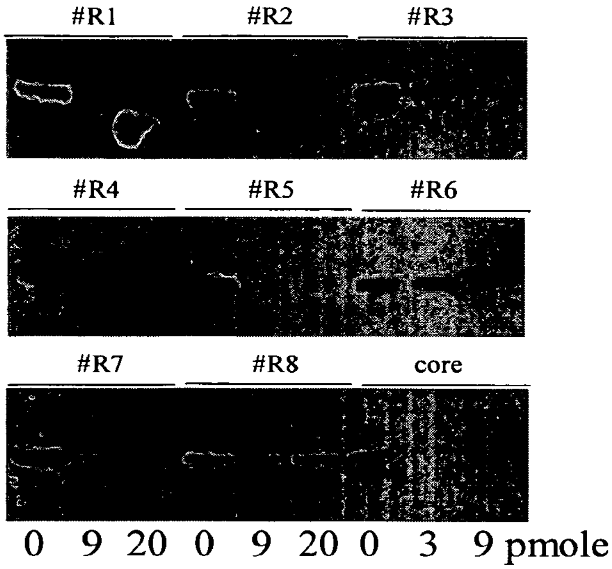
FIG. 14 is a Western Blot showing levels of HCV NS5A protein at 20 (I to r) 0, 9, and 20 pmole of the identified siRNA, and 0, 3, and 9 pmole of the "core" positive control siRNA, as described in more detail in Experiment 2 of Example 2.

Experiment 2 was performed as described in Experiment 1 of Hepatitis C-Sequences for RNAi Therapeutic Development except that siRNAs R1-R8, comprising the sequences (and their complements) set forth in Table 15 below, were used in transfections. The Western Blot assay performed here was as described in Example 2, Experiment 1. The control HCV core siRNA used as a positive control is the siRNA described in the previous HCV Experiment 1. All siRNAs were transfected at concentrations of 0, 9, and 20 pmole except the control "core" siRNA, which was transfected at levels of 0, 3, and 9 pmole. R1, R2, R3, R5, R7, and R8 all exhibited significant inhibition of HCV as can be seen in the Western Blot, FIG. 14.

TABLE 15

| siRNA | SEQ ID NO | HCV sequence |
|---|---|---|
| R1 | 37 | CTGGCCTCTCTGCAGATCAAG |
| R2 | 38 | TGCAGAGAGTGCTGATACTGG |
| R3 | 39 | TGAGCCGCTTGACTGCAGAGA |
| R4 | 40 | GAAAGGTCCGTGAGCCGCTT |
| R5 | 41 | TAGCTGTGAAAGGTCCGTGAG |
| R6 | 42 | TTAGCCCTAGTCACGGCTAGC |
| R7 | 43 | TCCATCTTAGCCCTAGTCACG |
| R8 | 44 | TTGGTGGCTCCATCTTAGCCC |

All siRNAs evaluated map to the 3'UTR of the HCV genome and are conserved amongst HCV genotypes and quasi-species. SEQ ID NO:27 represents this 101 nt sequence of the HCV 3'UTR, sometimes referred to as the "X" region.

Example 3

Silencing HBV Replication and Expression in a Replication Competent Cell Culture Model Brief Description of Cell Culture Model:

A human liver derived cell line such as the Huh7 cell line is transfected with an infectious molecular clone of HBV consisting of a terminally redundant viral genome that is capable of transcribing all of the viral RNAs and producing infectious virus [1-3]. The replicon used in these studies is derived from the virus sequence found in Gen Bank Accession #s V01460 and J02203. Following internalization into hepatocytes and nuclear localization, transcription of the infectious HBV plasmid from several viral promoters has been shown to initiate a cascade of events that mirrors HBV replication. These events include translation of transcribed viral mRNAs, packaging of transcribed pregenomic RNA into core particles, reverse transcription of pregenomic RNA, and assembly and secretion of virions and HBsAg (Hepatitis B Surface Antigen) particles into the media of transfected cells. This transfection model reproduces most aspects of HBV replication within infected liver cells and is therefore a good cell culture model with which to look at silencing of HBV expression and replication.

In this model, cells are co-transfected with the infectious molecular clone of HBV and the individual effector RNA constructs to be evaluated. The cells are then monitored for loss of HBV expression and replication as described below.

The following is an example of an experiment using eiRNA vectors encoding sequences derived from SEQ ID NO:1 and SEQ ID NO:5. The particular eiRNA vectors for this experiment are T7 RNA polymerase-based (See, e.g., the teaching of WO 0063364, with respect to T7 dsRNA expression systems, as well as U.S. Ser. No. 60/399,998P, filed 31 Jul. 2002 and U.S. Ser. No. 60/419,532, filed 18 Oct. 2002) and encode hairpin RNA structures (especially desirable are, e.g., "forced" hairpin constructs, partial hairpins capable of being extended by RNA-dependent RNA polymerase to form dsRNA hairpins, as taught in U.S. Ser. No. 60/399,998P, filed 31 Jul. 2002 and PCT/US2003/024028, filed 31 Jul. 2003, as well as the "udderly" structured hairpins (e.g., multi-hairpin long dsRNA vectors and multi-short hairpin structures), hairpins with mismatched regions, and multiepitope constructs as taught in U.S. Ser. No. 60/419,532, filed 18 Oct. 2002, and PCT/US2003/033466, filed 20 Oct. 2003). It is expected that similar results will be obtained using other expression and promoter systems, e.g., as described above, and/or vectors encoding alternative dsRNA structures (i.e. duplex).

Experimental Procedure: Transfection

Huh7 cells are seeded into six-well plates such that they are between 80-90% confluency at the time of transfection. All transfections are performed using Lipofectamine™ (Invitrogen) according to the manufacturer's directions. In this experiment, cells are transfected with 50 ng of the infectious HBV plasmid, 1 μg of a T7 RNA polymerase expression plasmid (description of plasmid below) 600 ng of an eiRNA vector encoding a hairpin RNA comprised of sequences derived from SEQ ID NO:1 (described below) and 600 ng of an eiRNA vector encoding a hairpin RNA comprised of sequences derived from SEQ ID NO:5 (described below). Control cells are transfected with 50 ng of the HBV plasmid and 1 μg of the T7 RNA polymerase expression plasmid. An inert filler DNA, pGL3-basic (Promega, Madison Wis.), is added to all transfections to bring total DNA/transfection up to 2.5 μg DNA.

Monitoring Cells for Loss of HBV Expression.

Following transfection, cells are monitored for the loss or reduction in HBV expression and replication by measuring HBsAg secretion and DNA-containing viral particle secretion. Cells are monitored by assaying the media of transfected cells beginning at 2 days post dsRNA administration and every other day thereafter for a period of three weeks. The Auszyme ELISA, commercially available from Abbott Labs (Abbott Park, Ill.), is used to detect hepatitis B surface antigen (HBsAg). HBsAg is measured since HBsAg is associated not only with viral replication but also with RNA polymerase II initiated transcription of the surface antigen cistron in the transfected infectious HBV clone. Since HBsAg synthesis can continue in the absence of HBV replication it is important to down-regulate not only viral replication but also replication-independent synthesis of HBsAg. Secretion of virion particles containing encapsidated HBV genomic DNA is also measured. Loss of virion particles containing encapsidated DNA is indicative of a loss of HBV replication. Analysis of virion secretion involves a technique that discriminates between naked, immature core particles and enveloped infectious HBV virions [6]. Briefly, pelleted viral particles from the media of cultured cells are subjected to Proteinase K digestion to degrade the core proteins. Following inactivation of Proteinase K, the sample is incubated with RQ1 DNase (Promega, Madison, Wis.) to degrade the DNA liberated from core particles. The sample is digested again with Proteinase K in the presence of SDS to inactivate the DNase as well as to disrupt and degrade the infectious enveloped virion particle. DNA is then purified by phenol/chloroform extraction and ethanol precipitated. HBV specific DNA is detected by gel electrophoresis followed by Southern Blot analysis.

Results will desirably indicate a 70-95% decrease in both HBsAg and viral particle secretion in the media of cells transfected with the HBV plasmid, T7 RNA polymerase expression plasmid and eiRNA constructs relative to cells transfected with only the HBV plasmid and T7 RNA polymerase expression plasmid.

Vectors Used in Experiment

Sequence of the T7 RNA Polymerase Gene

SEQ ID NO:47 represents the T7 RNA polymerase gene which is cloned into a mammalian expression vector such as pCEP4 (Invitrogen, Carlsbad, Calif.). Cloning can be easily done by one skilled in the art. One skilled in the art would also be aware that a leader sequence with a Kozak sequence needs to be cloned in directly upstream from the T7 RNA polymerase gene.

eiRNA Vector Encoding RNA Hairpin Derived from SEQ ID NO:1

The vector is T7-based as described above. The insert encodes a unimolecular hairpin comprised of sequences mapping from coordinate 3004-2950 (about 55 bp) of GenBank accession #s V01460 and J02203. One region of the hairpin encodes the sense version of the sequences and the second region of the hairpin encodes the antisense version of this sequence. Hairpins can easily be designed and made by those skilled in the art.

eiRNA Vector Encoding RNA Hairpin Derived from SEQ ID NO:5

The vector is T7-based as described above. The insert encodes a unimolecular hairpin comprised of sequences mapping from coordinate 730-786 of GenBank accession #s V01460 and J02203. The hairpin is designed as described for hairpin encoding sequences from SEQ ID NO:1.

Experiment 1

Rationale for Mouse Models:

Chimpanzees represent the only animal model in which to study human HBV infectivity. Mouse models are available, however, in which human HBV expression and replication occur. These models have been invaluable for the evaluation of anti-HBV therapeutic agents and have been shown to be a predictor for the efficacy of these agents in humans [4]. The first of these models are transgenic mouse models, in which the HBV genome or selected HBV genes are expressed [7,8]. Because HBV is integrated into the mouse genome, these animals serve as a model not only for viral replication but also for RT-independent expression of antigen. A similar model exists in which replication competent HBV is expressed transiently from episomal HBV DNA. This model is created by introducing replication competent HBV DNA into mouse liver by hydrodynamic delivery [1]. Unlike the transgenic animals, these mice are not immunotolerant to HBV antigens and immune-mediated clearance of HBV transfected hepatocytes can be studied.

Although woodchuck and duck models exist for the study of woodchuck hepatitis (WHBV) and duck hepatitis (DHBV) respectively, we have opted not to use these models for several reasons. 1) Human HBV cannot be studied in these models. As we are ultimately interested in down-regulating expression of human HBV, use of these models would at some point necessitate the re-design and evaluation of vectors and/or RNAs specific for human HBV. 2) the mice are isogenic and therefore noise due to genetic variables within the system does not arise. 3) Unlike human HBV, there are no validated WHBV/DHBV cell culture models that can be studied in parallel with their respective animal models.

The experiment described below utilizes hydrodynamic delivery as a method to co-deliver replication competent HBVayw plasmid with the various effector dsRNA (eiRNA) expression vectors. Hydrodynamic delivery is ideal for this experiment because it results in efficient delivery of nucleic acid to the liver [5]. Combination of the dsRNA effector plasmid and replication competent HBV plasmid into the same formulation increases the likelihood that both plasmids are taken up by the same cells. Because expressed effector dsRNA are present in the majority of cells bearing the replicating HBV plasmid, observed results can be attributed to the performance of the effector plasmid rather than to differences in delivery efficiencies. This experiment demonstrates only that a particular eiRNA is efficacious in an infected liver. Formulation and delivery are not addressed by this example. Formulation, dosing and delivery of the eiRNA vector are enabled in the example in which transgenic mice are used.

Experimental Procedure

Control B10.D2 mice are hydrodynamically injected with an infectious molecular clone of HBV (ayw subtype) consisting of a terminally redundant viral genome that is capable of transcribing all of the viral RNAs and producing infectious virus [1,2,3]. Following internalization into hepatocytes and nuclear localization, transcription of HBVayw plasmid from several viral promoters has been shown to initiate a cascade of events that mirror HBV replication [1]. These events include translation of transcribed viral mRNAs, packaging of transcribed pregenomic RNA into core particles, reverse transcription of pregenomic RNA, and assembly and secretion of virions and HBsAg particles into the sera of injected animals. Animals are injected with four doses of the HBV replicon plasmid (1 μg, 3 μg, 5 and 10 μg). These doses are chosen because they represent non-saturating doses capable of eliciting detectable expression of a reporter plasmid following hydrodynamic delivery. Animals are co-injected with the effector dsRNA expression vector (eiRNA) such that animals in each group receive a 10-19 μg dose of a particular effector construct(s) such that the total DNA dose is 20 μg. For example in mice receiving the 3 μg dose of the HBV replicon, 17 μg of the chosen eiRNA vector(s) is injected for a total of 20 μg injected DNA. The amount of this dose is therefore dependent upon the dose of HBV plasmid used. Control animals are injected with the HBV replicon but not with an eiRNA vector. Control mice are instead co-injected with an inert filler DNA, pGL3-basic (Promega, Madison, Wis.) such that the total amount of DNA in the formulation is 20 μg. eiRNA vectors in this study are the U6-based expression plasmids, e.g., Ambion, Inc., Austin, Tex., USA. These vectors encode short hairpin RNAs derived from SEQ ID NO:1 and SEQ ID NO:4. The exact sequences encoded by these vectors are described below. The vectors are co-injected in equal amounts (by weight). It is expected that similar results will be obtained using other expression and promoter systems as described elsewhere herein and/or vectors encoding alternative structures (i.e. duplex).

Description of U6-based eiRNA vector encoding sequences derived from SEQ ID NO:1: vector encodes a hairpin containing sequences mapping to coordinates 2905-2929 of accession #s V01460 and J02203 (i.e. the hairpin contains the sense and antisense version of this sequence, separated by a loop structure of TTCAAAAGA). Description of U6-based vector sequences can be found in Lee et al. [9]. The second eiRNA vector used in this experiment encodes a hairpin derived from SEQ ID NO:4 and encodes sequences mapping to coordinates 1215-1239 of Accession #V01460 and J02203.

Liver samples are taken from injected animals on day 1 following injection and analyzed for the presence of HBV RNA. This time point has been selected based on published results from Dr. Chisari's laboratory which detail the kinetics of HBVayw plasmid replication in mice following hydrodynamic delivery and demonstrates that peak RNA expression occurs in the liver on day 1 following hydrodynamic delivery [1]. The presence of HBV RNA in liver samples is ascertained by Northern blot analysis. Liver tissue will be evaluated for the down-regulation of HBV RNA expression. In addition, serum will be collected from day 4 mice for measurement of HBVsAg and DNA-containing viral particles. Assays will be as described for the cell culture replicon experiment (Example 3) and as in Yang et al. [1]. Each vector and control group will be comprised of 2 sets of animals, each set corresponding to a collection time point. There are 5 animals is each set.

Results:

Mice that are injected with the HBV replicon and the eiRNA constructs will have decreased HBV-specific RNA, and HBsAg and HBV viral particles as compared to the control animals. In individual animals, decreases will range from about 70% to near 100%.

Experiment 2

Transgenic Mouse Studies: Background.

We will be using the HBV transgenic mouse model developed in Dr. Chisari's laboratory [8]. These mice replicate appreciable amounts of HBV DNA and have demonstrated their utility as an antiviral screen that is a predictor of human efficacy [4]. These animals are also ideal in that they are a model for HBV-integrant-mediated expression of antigen and thus can serve as a model not only for viral replication but also for RT-independent expression of antigen. This is important as we are interested in targeting not only viral replication but integrant-mediated antigen expression as well.

These experiments differ from the hydrodynamic delivery experiments in that the effector plasmids are administered to animals using clinically relevant nucleic acid delivery methods. Effectiveness in this model demonstrates efficient delivery of the effector plasmids to mouse hepatocytes.

Experiment

Mice described in reference [8] will be injected IV with a formulation containing the eiRNA vectors described in the hydrodynamic delivery example. These are the U6-based eiRNA vectors encoding hairpins containing sequences derived from SEQ ID NO:1 and SEQ ID NO:4.

Formulation of DNA to be Injected.

DNA is formulated with trilactosyl spermine and cholesteryl spermine as described in PCT/US03/14288, "Methods for Delivery of Nucleic Acids", Satishchandran, filed 6 May 2003. Briefly, three formulations are made, all using a charge ratio of 1.2 (positive to negative charge). However, it should noted that formulations with charge ratios between 0.8 and 1.2 are all expected to exhibit efficacy. The DNA starting stock solution for each plasmid is 4 mg/ml. The two plasmid stock solutions are mixed together in equal amounts such that each plasmid is at 2 mg/ml. This plasmid mixture is used for the final formulating. Formulation is as described in PCT/US03/14288 (above): Formulation A) 35% trilactosyl spermine, 65% cholesteryl spermine, Formulation B) 50% trilactosyl spermine, 50% cholesteryl spermine and Formulation C) 80% trilactosysl spermine, 20% cholesteryl spermine. All resultant formulations now contain each plasmid at 1 mg/ml.

Mice are IV injected with 100 μl formulated DNA. One group of mice receives Formulation A, a second group receives Formulation B and a third group receives Formulation C. Three groups of control mice are similarly injected with formulations containing a control DNA, pGL3Basic (Promega, Madison Wis.), Formulations D, E and F. Injections are carried out once a day for four consecutive days.

Injecting for only 1-3 days is efficacious, however, more robust efficacy is seen with a four day injection protocol.

Following administration, HBV RNA and serum levels of HBsAg and DNA containing viral particles will be quantitated on days 5 and 9 post first injection. All analyses will be as described for the hydrodynamic delivery studies.

Results:

HBV-specific RNA levels, HBsAg and virus containing DNA particles will have decreased relative to controls in the Formulation A, B and C groups.

Example #4

Silencing HBV Replication and Expression in a Replication Competent Cell Culture Model Brief Description of Cell Culture Model:

A human liver derived cell line such as the Huh7 cell line is transfected with an infectious molecular clone of HBV consisting of a terminally redundant viral genome that is capable of transcribing all of the viral RNAs and producing infectious virus [1-3]. The replicon used in these studies is derived from the virus sequence found in Gen Bank Accession AF090840. Following internalization into hepatocytes and nuclear localization, transcription of the infectious HBV plasmid from several viral promoters has been shown to initiate a cascade of events that mirror HBV replication. These events include translation of transcribed viral mRNAs, packaging of transcribed pregenomic RNA into core particles, reverse transcription of pregenomic RNA, and assembly and secretion of virions and HBsAg particles into the media of transfected cells. This transfection model, reproduces most aspects of HBV replication within infected liver cells and is therefore a good cell culture model with which to look at silencing of HBV expression and replication.

In this model, cells were co-transfected with the infectious molecular clone of HBV and an eiRNA construct. The cells were then monitored for loss of HBV expression and replication as described below.

The following is an example of an experiment that was performed using an eiRNA vector encoding sequences derived from both SEQ ID NO:1 and SEQ ID NO:2. The particular eiRNA vector used for this experiment is T7 RNA polymerase-based and encodes a duplex RNA of about 650 by (See e.g., WO 00/63364, filed Apr. 19, 2000). It is expected that similar results would be obtained using other expression and promoter systems as described elsewhere herein and/or vectors encoding alternative structures (i.e. duplex).

Experimental Procedure: Transfection

Huh7 cells were seeded into six-well plates such that they were between 80-90% confluency at the time of transfection. All transfections were performed using Lipofectamine™ (InVitrogen) according to the manufacturer's directions. In this experiment, cells were transfected with A) 50 ng of the infectious HBV plasmid adw subtype, 1 μg of a T7 RNA polymerase expression plasmid (description of plasmid in Example 3), and 1.5 μg of the HBV-specific eiRNA vector (described below); B) 50 ng of the infectious HBV plasmid, 1 μg of the T7 RNA polymerase expression plasmid and 1.5 μg of an irrelevant dsRNA expression vector; C) 125 ng of the infectious HBV plasmid, 1 μg of the T7 RNA polymerase expression plasmid and 1.4 μg of the HBV-specific eiRNA vector; and D) 125 ng of the infectious HBV plasmid, 1 μg of the T7 RNA polymerase expression plasmid and 1.4 μg of an irrelevant dsRNA expression vector. All transfections were carried out in duplicate. In this experiment transfections B and D served as controls. Four days post-transfection, media was removed from transfected cells and assayed for the presence of HBsAg (see below). Media from untransfected cells was also assayed as a background control.

Monitoring Cells for Loss of HBV Expression.

Following transfection, cells were monitored for the loss or reduction in HBV expression and replication by measuring HBsAg secretion. Cells were monitored by assaying the media of transfected cells (and a media control) at 4 days post-dsRNA administration. The Auszyme ELISA, commercially available from Abbott Labs (Abbott Park, Ill.), was used to detect hepatitis B surface antigen (HBsAg). HBsAg was measured since it is associated not only with viral replication but also with RNA polymerase II initiated transcription of the surface Ag cistron in the transfected infectious HBV clone. Since HBsAg synthesis can continue in the absence of HBV replication it is important to down-regulate not only viral replication but also replication-independent synthesis of HB sAg.

Results:

Cells transfected with the HBV-specific eiRNA construct exhibited an 82-93% decrease in HBsAg at the four-day timepoint relative to the control transfections.

HBV-Specific eiRNA Used in this Experiment

The eiRNA vector encodes a dsRNA mapping to coordinates 2027-2674 of Gen Bank Accession #AF090840. The sequence therefore includes sequences derived from both SEQ ID NO:1 and SEQ ID NO:2. More specifically, the sequence includes all of SEQ ID NO:2 and 134 by derived from SEQ ID NO:1.

Example #5

The Down-Regulation of HCV in a Cell Culture Replicon Model

Brief Description

In this experiment, a cell line is created which expresses functional HCV replicons. Creation of the cell line is as detailed in Lohmann et al. [10]. In this experiment Huh7 cells are used as the parental cell line but in theory any human hepatocyte derived cell line can be used. The cells are then transfected with an HCV specific eiRNA vector. The presence of HCV-specific RNA is ascertained by Northern blot analysis as described in Lohmann et al. [10] at days 3-7 post-transfection of eiRNA.

Experimental Protocol: Transfection

Huh7 cells expressing HCV replicons are seeded into six-well plates such that they are between 80-90% confluency at the time of transfection. All transfections are performed using Lipofectamine™ (InVitrogen) according to the manufacturer's directions. In this experiment, cells are transfected with 1 μg of a T7 RNA polymerase expression plasmid (plasmid described in Example 3) and 1.5 μg of a T7-based eiRNA vector encoding a hairpin RNA comprised of sequences derived from SEQ ID NO:11 (vector described at end of example). Control cells are transfected with 1 μg T7 RNA polymerase expression plasmid and 1.5 μg of the HBV-specific (SEQ ID NO:1 specific) T7-based eiRNA vector described in Example 3. Untransfected replicon-expressing HuH 7 cells are included as a second control. Each transfection mix is made such that ten transfections can be performed/mix resulting in a total of 20 transfections (10 per mix). At days 3, 4, 5, 6, and 7, two wells of cells/each transfection are lysed and RNA is extracted using standard techniques. Samples are analyzed simultaneously by Northern blot analysis for the presence of HCV-specific RNA as described in Lohmann et al. [10].

Results

Cells transfected with the HCV-specific eiRNA vector will show decreased HCV-specific RNA levels relative to the control cells at every time-point analyzed.

HCV-Specific eiRNA Vector.

The eiRNA vector is T7-based and encodes a hairpin RNA. One side of the hairpin comprises SEQ ID NO:48.

This sequence is followed by a loop structure of 9 Ts. The second side of the hairpin contains a sequence that is complementary to the first side of the hairpin. One skilled in the art can easily design and construct hairpin constructs. Note: it is anticipated that other types of eiRNA vectors driven by other promoters and encoding other types of RNA structures will have similar effects.

Example #6

Treatment of an HBV/HCV Co-Infection

Brief Description

In this example, cells that are replicating both HBV and HCV replicons are transfected with an eiRNA vector that encodes both HBV and HCV-specific eiRNA.

Experimental Protocol

Creation of Cell Lines that Contain Both HBV and HCV Replicons.

HuH 7 cells are first engineered to express functional HCV replicons. Creation of the cell line is as detailed in Lohmann et al. [10]. After cell line establishment, the cells are transfected with an infectious HBV replicon plasmid as described in Example 3 and below in the "Transfection of cells" section. In this example, the replicon is derived from the virus sequence found in Gen Bank Accession #s V01460 and J02203. Theoretically, it is also possible to first create a cell line that stably expresses the HBV replicon and then use this cell line to create one that also expresses HCV replicons. It is also possible to transfect the cells simultaneously with both the HBV and HCV replicons and select and expand cells that are replicating both HBV and HCV replicons.

Transfection of Cells.

In this example, the HBV and HCV eiRNAs are encoded by separate cistrons within the same vector. However, similar results are expected if the eiRNAs are encoded within the same cistron or provided by separate vectors. In this example, transcription from each cistron is driven by the T7 RNA polymerase promoter and T7 RNA polymerase. Each promoter is followed by a hairpin eiRNA which in turn is followed by a T7 terminator (FIG. 1). The cistrons in this example are converging but one could also use diverging cistrons. It should also be noted that one could use other expression systems (including viral) to produce these RNAs and one could also use other promoters, e.g., as described elsewhere herein, to drive expression of these RNAs without significantly affecting efficacy. Selection of the appropriate expression systems and promoters is within the skill in this art. Also one could express other eiRNA structures, e.g., as described elsewhere herein, as well as others, described in the literature in this area. In this example, the HBV eiRNA vector encodes sequences derived from SEQ ID NO:1 and the HCV eiRNA vector encodes sequences derived from SEQ ID NO:11. Description of vector inserts is located at the end of this example.

Huh7 cells are seeded into six-well plates such that they are between 80-90% confluency at the time of transfection. All transfections are performed using Lipofectamine™ (Invitrogen) according to the manufacturer's directions. In this experiment, cells are transfected with 50 ng of the infectious HBV plasmid, 1 μg of a T7 RNA polymerase expression plasmid (description of plasmid is in Example 3), 600 ng of an eiRNA vector encoding a hairpin RNA comprised of sequences derived from SEQ ID NO:1 (described below and in Example 3), and 600 ng of an eiRNA vector encoding a hairpin RNA comprised of sequences derived from SEQ ID NO:11 (described below). Control cells are transfected with 50 ng of the HBV plasmid and 1 μg of the T7 RNA polymerase expression plasmid. An inert filler DNA, pGL3-basic (Promega, Madison Wis.), is added to all transfections where needed to bring total DNA/transfection up to 2.5 μg DNA. Each transfection mix is made such that ten transfections can be performed/mix resulting in a total of 20 transfections (10 per mix).

Analyses.

Following transfection, cells are monitored for the loss or reduction in HBV expression and replication by measuring HBsAg secretion and DNA-containing viral particle secretion. Cells are monitored by assaying the media of transfected cells beginning at 2 days post dsRNA administration and every other day thereafter for a period of three weeks. The Auszyme ELISA, commercially available from Abbott Labs (Abbott Park, Ill.), is used to detect hepatitis B surface antigen (HBsAg). HBsAg is measured since it is associated not only with viral replication but also with RNA polymerase II initiated transcription of the surface Ag cistron in the transfected infectious HBV clone. Since HBsAg synthesis can continue in the absence of HBV replication it is important to down-regulate not only viral replication but also replication-independent synthesis of HBsAg. Secretion of virion particles containing encapsidated HBV genomic DNA is also measured. Loss of virion particles containing encapsidated DNA is indicative of a loss of HBV replication. Analysis of virion secretion involves a technique that discriminates between naked, immature core particles and enveloped infectious HBV virions [6]. Briefly, pelleted viral particles from the media of cultured cells are subjected to Proteinase K digestion to degrade the core proteins. Following inactivation of Proteinase K, the sample is incubated with RQ1 DNase (Promega, Madison, Wis.) to degrade the DNA liberated from core particles. The sample is digested again with Proteinase K in the presence of SDS to inactivate the DNase as well as to disrupt and degrade the infectious enveloped virion particle. DNA is then purified by phenol/chloroform extraction and precipitated. HBV specific DNA is detected by gel electrophoresis followed by Southern Blot analysis.

At days 3, 4, 5, 6 and 7, two wells of cells/each transfection (experimental and control) are lysed and RNA is extracted using standard techniques. Samples are also analyzed by Northern blot analysis for the presence of HCV-specific RNA as described in Lohmann et al. [10].

Results.

Cells transfected with the HBV-HCV-specific eiRNA vector will show decreased HCV-specific RNA levels relative to the control cells at every time-point analyzed. In addition, the levels of HBsAg and HBV viral particles will also decrease relative to the control transfections.

HCV-Specific eiRNA Sequence.

The eiRNA vector is T7-based and encodes a hairpin RNA. One side of the hairpin comprises SEQ ID NO:48.

This sequence is followed by a loop structure of 9 Ts. The second side of the hairpin contains a sequence that is complementary to the first side of the hairpin. One skilled in the art can easily design and construct hairpin constructs. Note: it is anticipated that other types of eiRNA vectors driven by other promoters, including RNA polymerase III promoters, and encoding other types of RNA structures, including various hairpin structures will have similar effects. Especially desirable are, e.g., "forced" hairpin constructs, partial hairpins capable of being extended by RNA-dependent RNA polymerase to form dsRNA hairpins, as taught in U.S. Ser. No. 60/399,998P, filed 31 Jul. 2002 and PCT/US2003/024028, filed 31 Jul. 2003, as well as the "udderly" structured hairpins (e.g., multi-hairpin long dsRNA vectors and multi-short hairpin structures), hairpins with mismatched regions, and multiepitope constructs as taught in U.S. Ser. No. 60/419,532, filed 18 Oct. 2002, and PCT/US2003/033466, filed 20 Oct. 2003, as well as a variety of other dsRNA structures known to those of skill in the art.

HBV-Specific eiRNA-SEQ ID NO:1

The vector is T7-based as described above. The insert encodes a unimolecular hairpin comprised of sequences mapping from coordinate 3004-2950 (About 55 bp) of GenBank accession #s V01460 and J02203. One region of the hairpin encodes the sense version of the sequences and the second region of the hairpin encodes the antisense version of this sequence. Hairpins can easily be designed and made by those skilled in the art.

Example #7

Silencing HBV Replication and Expression in a Replication Competent Cell Culture Model (See Example 1) Using Combinations of HBV-Specific eiRNAs in Multiple Promoter Vectors As disclosed in PCT/US05/29976, filed 23 Aug. 2005 and in U.S. Provisional Applications entitled "Multiple RNA Pol III Promoter Expression Constructs" (Ser. No. 60/603,622, filed Aug. 23, 2004, and Ser. No. 60/629,942, filed Nov. 22, 2004) the teaching of which is hereby incorporated by reference, two or more (preferably 3, 4, 5, 6 or more) of the shRNA sequences shown in Table I and SEQ ID NO:49 may be encoded in the same plasmid vector in separate cistrons under the control of separate promoters for each shRNA. SEQ ID NO:49 is:

GCCTCGCAGACGAAGGTCTCAAGAGAACTTTGAGACCTTCGTCTGCGAGG

C

SEQ ID NO:49 represents the coding strand of a DNA sequence which encodes an shRNA molecule that targets an HBV conserved region. The first 21 bases of the sequence above are identical to the sense sequence of HBV mRNA from position 799 to 779 in the HBV genome, strain AYW (numbered according to the complement strand given in Genbank Accession No. V01460). This sequence is followed by 9 bases (i.e., AGAGAACTT) representing the loop portion of the shRNA, followed by 21 bases of the reverse complementary sequence to the first 21 bases. (It will be understood that the loop sequence serves only to join the complementary sequences which form the double-stranded "stem" and therefore considerable variation in length and nucleotide sequence is acceptable within the loop region.) In a preferred embodiment, this DNA sequence will be placed in an appropriate expression vector operably under the control of a promoter, preferably an RNA polymerase III promoter such 7SK, U6, etc. The resulting RNA transcript:

GCCUCGCAGACGAAGGUCUCAAGAGAACUUUGAGACCUUCGUCUGCGAGG

C will assume a hairpin or stem-loop structure having 21 basepairs in a double-stranded conformation.

Using methods commonly employed by one skilled in the art of molecular biology, a single vector encoding two or more, preferably three or more, more preferably four or more, five or more, or all of SEQ ID NO:49, SEQ ID NO:18, SEQ ID NO:19, SEQ ID NO:21, SEQ ID NO:22, and SEQ ID NO:23 is constructed. A particularly preferred embodiment for pharmaceutical applications of dsRNA-mediated silencing of the HBV target comprises a single expression construct encoding under the control of separate RNA polymerase III promoters, shRNAs corresponding to at least SEQ ID NO:19, SEQ ID NO:23, and SEQ ID NO:18, and optionally, SEQ ID NO:49 and/or SEQ ID NO:21. Such shRNA-expression vectors may advantageously utilize one or more RNA polymerase III promoters, including U6, 7SK, and H1 promoters in several alternative orientations and combinations. Particularly preferred constructs will utilize one or more of the 7SK promoters as taught in U.S. Provisional Ser. Nos. 60/603,622 and 60/629,942. The instant example is thus analogous to Experiment 1 in Example 1 except that instead of introducing one vector with one shRNA at a time, the applicants deliver a single plasmid construct which expresses multiple shRNAs.

The advantages of this approach for therapeutic applications of dsRNA silencing are principally in the economy, simplicity and coordinated delivery of a single drug entity which comprises multiple different shRNAs each targeting a different site of the HBV genome. The ability to simultaneously target multiple sites of a viral genome is highly advantageous in preventing the clinically widespread phenomenon of drug resistance (by viral mutation), and the ability to combine dsRNA drug entities against these different target sites in a single delivery agent (the plasmid vectors of this invention) makes this conceptual approach uniquely feasible. While shRNAs, e.g., RNAs corresponding to SEQ ID NO:49, SEQ ID NO:18, SEQ ID NO:19, SEQ ID NO:21, SEQ ID NO:22, and SEQ ID NO:23 may be produced, e.g., through chemical synthesis or in vitro expression, and delivered into an animal cell singly and in combination, there are significant advantages in some applications to express within the animal cell multiple shRNAs from a single expression vector. In this example, the potency of the multiple shRNA expression vectors significantly exceeded that of any one of the single vectors used in Experiment 1, as measured by similar assays.

Example #8

Inhibition of Infectious Virions of HCV by dsRNA Effector Molecules

As a further example of HCV-targeted dsRNAs, the sequences given in Table 16 represent highly conserved coding region sequitopes from the 5' and 3' untranslated regions of HCV. Each sequence is written as the coding strand and is used to specify the design of a short hairpin dsRNA effector molecule comprising the coding sequence as shown in Table 16 connected to its reverse complement by a loop or linker sequence as described elsewhere herein. The sequences shown are predicted to be particularly efficacious as antiviral therapeutic agents because they were tested in a newly available in vitro HCV replication system capable of producing whole, infectious virions (disclosed in Wakita T, Pietschmann T, Kato T, Date T, Miyamoto M, Zhao Z, Murthy K, Habermann A, Krausslich H G, Mizokami M, Bartenschlager R, Liang T J., "Production of infectious hepatitis C virus in tissue culture from a cloned viral genome", Nat Med 2005 July; 11 (7):791-6; and in Zhong J, Gastaminza P, Cheng G, Kapadia S, Kato T, Burton D R, Wieland S F, Uprichard S L, Wakita T, Chisari F V., "Robust hepatitis C virus infection in vitro", Proc Natl Acad Sci USA 2005 Jun. 28; 102(26):9294-9). In this system, all viral proteins and viral nucleic acid sequences are present in a cell, as in a natural infection. In less complete replicon systems, dsRNA silencing molecules cannot be as rigorously tested as in the new system. It is expected that one or more (2, 3, 4, 5, or more) of the HCV sequitopes and their complements could be utilized as duplex dsRNA effector molecules, short hairpin dsRNA effector molecules, and/or encoded into dsRNA expression vectors capable of expression in vivo in a mammalian cell, including a human cell or organism.

TABLE 16

| Seq Name | SEQ ID NO | Sequence (5' to 3') |
|---|---|---|
| HCV5M-5.1 | 72 | AAAGGCCTTGTGGTACTGCCT |
| HCV5M-5.3 | 73 | TTGTGGTACTGCCTGATAGGG |
| HCVXM-13 | 74 | TAGCTGTGAAAGGTCCGTGAG |
| HCVXM-34 | 75 | ATCTTAGCCCTAGTCACGGCTAGCTG |
| HCVXM-35 | 76 | TAGTCACGGCTAGCTGTGAAAGGTCCG |

The sequences in Table 17 represent additional preferred highly conserved at least 19 contiguous base pair HCV sequences from the 5' UTR of the virus (SEQ ID NO: 11). To generate the dsRNA effector molecules of the invention, these sequences are used in conjunction with their reverse complement and, optionally, a loop or linker sequence joining the sequence to its reverse complement, when it is desired to form a hairpin dsRNA effector molecule. One or more double-stranded RNA molecules comprising said conserved 5' UTR sequences (from SEQ ID NO: 11) may advantageously be used in combination with one or more other dsRNA effector molecules of the invention, including e.g., one or more highly conserved sequences from the 3' UTR (SEQ ID NO:27) and/or one or more at least 19 contiguous base pair sequences from SEQ ID NO. 12.

TABLE 17

| HCV 5' UTR siRNAs Sequence Name | Sequence (5' to 3') | SEQ ID NO |
|---|---|---|
| HCV5P-1.1 | CCTGTGAGGAACTACTGTCTT | 77 |
| HCV5P-1.2 | ACGCAGAAAGCGTCTAGCCAT | 78 |
| HCV5P-1.3 | CGTCTAGCCATGGCGTTAGTA | 79 |
| HCV5P-1.4 | GTCTAGCCATGGCGTTAGTAT | 80 |
| HCV5P-1.5 | CTCCCCTGTGAGGAACTACTGTCTT | 81 |
| HCV5P-1.6 | GAGGAACTACTGTCTTCACGCAGAA | 82 |
| HCV5P-1.7 | GTGAGGAACTACTGTCTTCACGCAGAA | 83 |
| HCV5P-2.1 | GAGCCATAGTGGTCTGCGGAA | 84 |
| HCV5P-2.2 | GAACCGGTGAGTACACCGGAA | 85 |
| HCV5P-2.3 | ACCGGTGAGTACACCGGAAT | 86 |
| HCV5P-2.4 | GGGAGAGCCATAGTGGTCTGCGGAA | 87 |
| HCV5P-5.1 | GGCCTTGTGGTACTGCCTGAT | 88 |
| HCV5P-5.2 | GCCTTGTGGTACTGCCTGATA | 89 |
| HCV5P-5.3 | GTACTGCCTGATAGGGTGCTT | 90 |
| HCV5P-5.4 | AAGGCCTTGTGGTACTGCCTGATAGGG | 91 |
| HCV5P-5.5 | CGAAAGGCCTTGTGGTACTGCCTGATA | 92 |
| HCV5P-5.6 | CTTGCGAGTGCCCCGGGAGGTCTCGTA | 93 |
| HCV5M-1.1 | ATCACTCCCCTGTGAGGAACT | 94 |
| HCV5M-1.2 | TTCACGCAGAAAGCGTCTAGC | 95 |
| HCV5M-1.3 | TAGCCATGGCGTTAGTATGAG | 96 |
| HCV5M-1.4 | ATCACTCCCCTGTGAGGAACTACTG | 97 |
| HCV5M-1.5 | ATCACTCCCCTGTGAGGAACTACTGTC | 98 |
| HCV5M-1.6 | AACTACTGTCTTCACGCAGAAAGCG | 99 |
| HCV5M-1.7 | AACTACTGTCTTCACGCAGAAAGCGTC | 100 |
| HCV5M-2.1 | ATAGTGGTCTGCGGAACCGGT | 101 |
| HCV5M-2.2 | TAGTGGTCTGCGGAACCGGTG | 102 |
| HCV5M-2.3 | AACCGGTGAGTACACCGGAATTGCC | 103 |
| HCV5M-5.2 | AAGGCCTTGTGGTACTGCCTG | 104 |
| HCV5M-5.4 | TACTGCCTGATAGGGTGCTTG | 105 |
| HCV5M-5.5 | TTGTGGTACTGCCTGATAGGGTGCTTG | 106 |
| HCV5M-5.6 | TACTGCCTGATAGGGTGCTTGCGAG | 107 |
| HCV5M-5.7 | TAGGGTGCTTGCGAGTGCCCCGGG | 108 |
| HCV5M-5.8 | TTGCGAGTGCCCCGGGAGGTCTCGTAG | 109 |

REFERENCES

1. Yang, P. L., et al., *Hydrodynamic injection of viral DNA: a mouse model of acute hepatitis B virus infection*. Proc Natl Acad Sci USA, 2002. 99(21): p. 13825-30.
2. Guidotti, L. G., et al., *Viral clearance without destruction of infected cells during acute HBV infection*. Science, 1999. 284(5415): p. 825-9.

3. Thimme, R., et al., *CD8(+) T cells mediate viral clearance and disease pathogenesis during acute hepatitis B virus infection*. J Virol, 2003. 77(1): p. 68-76.
4. Morrey, J. D., et al., *Transgenic mice as a chemotherapeutic model for Hepatitis B infection*" In "Therapies for Viral Hepatitis" Eds. Schinazi, R. F., Sommadossi, J-P. and Thomas, H. C., International medical Press, Holborn, London WC 1V 6QA, UK, 1998.
5. Liu, F., Y. Song, and D. Liu, *Hydrodynamics-based transfection in animals by systemic administration of plasmid DNA*. Gene Ther, 1999. 6(7): p. 1258-66.
6. Delaney, W. E. t. and H. C. Isom, *Hepatitis B virus replication in human HepG2 cells mediated by hepatitis B virus recombinant baculovirus*. Hepatology, 1998. 28(4): p. 1134-46.
7. Chisari, F. V., et al., *A transgenic mouse model of the chronic hepatitis B surface antigen carrier state*. Science, 1985. 230(4730): p. 1157-60.
8. Guidotti, L. G., et al., *High-level hepatitis B virus replication in transgenic mice*. J Virol, 1995. 69(10): p. 6158-69.
9. Lee, N S, Dohjima, T., Bauer G., Li, H. Li, M. J., Ehsani, A., Salvaterra, P. and Rossi, J. *Expression of small interfering RNAs targeted against HIV-1 rev transcripts in human cells*. Nature Biotechnology, 2002, p. 500-505.
10. Lohmann, V., Korner, F., Koch, J.-O., Herian, U., Theilmann, L. and Bartenschlager. R. *Replication of Subgenomic Hepatitis C Virus RNAs in a Hepatoma Cell Line*. Science. 1999. 285: 110-113.

---

The invention claimed is:

1. A composition for inhibiting the expression of a polynucleotide sequence of hepatitis B virus in an in vivo mammalian cell comprising a double-stranded RNA effector molecule, wherein the double-stranded RNA effector molecule comprises (a) SEQ ID NO: 52 and the reverse complement of SEQ ID NO: 52, wherein U is substituted for T; or (b) SEQ ID NO: 53 and the reverse complement of SEQ ID NO: 53, wherein U is substituted for T.

2. The composition of claim 1, wherein the double-stranded effector molecule comprises SEQ ID NO: 52 and the reverse complement of SEQ ID NO: 52, wherein U is substituted for T.

3. The composition of claim 1, wherein the double-stranded effector molecules comprises SEQ ID NO: 53 and the reverse complement of SEQ ID NO: 53, wherein U is substituted for T.

4. The composition of claim 1, wherein the double-stranded RNA effector molecule comprises SEQ ID NO: 16, wherein U is substituted for T.

5. The composition of claim 1, wherein the double-stranded RNA effector molecule comprises SEQ ID NO: 17, wherein U is substituted for T.

6. A method for inhibiting expression of a polynucleotide sequence of hepatitis B virus in an in vivo mammalian cell comprising administering to said cell the double-stranded RNA effector molecule of claim 1.

7. The method of claim 6, wherein the double-stranded effector molecule comprises SEQ ID NO: 52 and the reverse complement of SEQ ID NO: 52, wherein U is substituted for T.

8. The method of claim 6, wherein the double stranded effector molecule comprises SEQ ID NO: 53 and the reverse complement of SEQ ID NO: 53, wherein U is substituted for T.

9. The method of claim 6, wherein the double-stranded RNA effector molecule comprises SEQ ID NO: 16, wherein U is substituted for T.

10. The method of claim 6, wherein the double-stranded RNA effector molecule comprises SEQ ID NO: 17, wherein U is substituted for T.

* * * * *

SEQUENCE LISTING

```
<160> NUMBER OF SEQ ID NOS: 266

<210> SEQ ID NO 1
<211> LENGTH: 138
<212> TYPE: DNA
<213> ORGANISM: Hepatitis B virus
<220> FEATURE:
<221> NAME/KEY: modified_base
<222> LOCATION: (137)..(137)
<223> OTHER INFORMATION: a, c, t or g

<400> SEQUENCE: 1

gaacatggag arcayhdcat caggaytcct aggacccctg ctcgtgttac aggcggkgtk      60

tttctygttg acaaraatcc tcacaatacc dcagagtcta gactcgtggt ggacttctct     120

caattttcta ggggdany                                                   138


<210> SEQ ID NO 2
<211> LENGTH: 26
<212> TYPE: DNA
<213> ORGANISM: Hepatitis B virus

<400> SEQUENCE: 2

tggatgtgtc trcggcgttt tatcat                                           26


<210> SEQ ID NO 3
<211> LENGTH: 206
<212> TYPE: DNA
<213> ORGANISM: Hepatitis B virus
<220> FEATURE:
<221> NAME/KEY: modified_base
<222> LOCATION: (63)..(63)
<223> OTHER INFORMATION: a, c, t or g
<220> FEATURE:
<221> NAME/KEY: modified_base
<222> LOCATION: (111)..(111)
<223> OTHER INFORMATION: a, c, t or g
<220> FEATURE:
<221> NAME/KEY: modified_base
<222> LOCATION: (140)..(140)
<223> OTHER INFORMATION: a, c, t or g
<220> FEATURE:
<221> NAME/KEY: modified_base
<222> LOCATION: (174)..(174)
<223> OTHER INFORMATION: a, c, t or g
<220> FEATURE:
<221> NAME/KEY: modified_base
<222> LOCATION: (177)..(177)
<223> OTHER INFORMATION: a, c, t or g

<400> SEQUENCE: 3

aaggcctttc tvhgtmaaca rtaymtgmmc ctttaccccg ttgcymggca acggychggy      60
```

-continued

```
ctntgccaag tgtttgctga cgcaaccccc actgghtggg gcttggybat nggccatcrs    120

cgcatgcgtg gaacctttbn gkctcctctg ccgatccata ctgcggaact cctngcngcb    180

tgtttygctc gcagcmggtc tggrgc                                         206


<210> SEQ ID NO 4
<211> LENGTH: 119
<212> TYPE: DNA
<213> ORGANISM: Hepatitis B virus

<400> SEQUENCE: 4

yactgttcaa gcctcaagct gtgccttggg tggctttrgg rcatggacat tgacmcktat     60

aaagaatttg gagctwctgt ggagttactc tcdtttttgc cttcygactt ytttccttc     119


<210> SEQ ID NO 5
<211> LENGTH: 102
<212> TYPE: DNA
<213> ORGANISM: Hepatitis B virus

<400> SEQUENCE: 5

cgabgcaggt cccctagaag aagaactccc tcgcctcgca gacgmagrtc tcaatcgmcg     60

cgtcgcagaa gatctcaaty tcgggaatct yaatgttagt at                       102


<210> SEQ ID NO 6
<211> LENGTH: 100
<212> TYPE: DNA
<213> ORGANISM: Hepatitis B virus

<400> SEQUENCE: 6

abgcaggtcc cctagaagaa gaactccctc gcctcgcaga cgmagrtctc aatcgmcgcg     60

tcgcagaaga tctcaatytc gggaatctya atgttagtat                         100


<210> SEQ ID NO 7
<211> LENGTH: 101
<212> TYPE: DNA
<213> ORGANISM: Hepatitis B virus

<400> SEQUENCE: 7

cabgcaggtc ccctagaaga agaactccct cgcctcgcag acgmagrtct caatcgmcgc     60

gtcgcagaag atctcaatyt cgggaatcty aatgttagta t                        101


<210> SEQ ID NO 8
<211> LENGTH: 101
<212> TYPE: DNA
<213> ORGANISM: Hepatitis B virus

<400> SEQUENCE: 8

gabgcaggtc ccctagaaga agaactccct cgcctcgcag acgmagrtct caatcgmcgc     60

gtcgcagaag atctcaatyt cgggaatcty aatgttagta t                        101


<210> SEQ ID NO 9
<211> LENGTH: 104
<212> TYPE: DNA
<213> ORGANISM: Hepatitis B virus
<220> FEATURE:
<221> NAME/KEY: modified_base
<222> LOCATION: (9)..(9)
<223> OTHER INFORMATION: a, c, t or g
<220> FEATURE:
<221> NAME/KEY: modified_base
<222> LOCATION: (38)..(38)
<223> OTHER INFORMATION: a, c, t or g
```

<220> FEATURE:
<221> NAME/KEY: modified_base
<222> LOCATION: (72)..(72)
<223> OTHER INFORMATION: a, c, t or g
<220> FEATURE:
<221> NAME/KEY: modified_base
<222> LOCATION: (75)..(75)
<223> OTHER INFORMATION: a, c, t or g

<400> SEQUENCE: 9
ttggybatng gccatcrscg catgcgtgga acctttbngk ctcctctgcc gatccatact 60
gcggaactcc tngcngcbtg tttygctcgc agcmggtctg grgc 104

<210> SEQ ID NO 10
<211> LENGTH: 71
<212> TYPE: DNA
<213> ORGANISM: Hepatitis B virus
<220> FEATURE:
<221> NAME/KEY: modified_base
<222> LOCATION: (71)..(71)
<223> OTHER INFORMATION: a, c, t or g

<400> SEQUENCE: 10
ctgccaactg gathcthcgc gggacgtcct ttgtytacgt cccgtcrgcg ctgaatcchg 60
cggacgaccc n 71

<210> SEQ ID NO 11
<211> LENGTH: 490
<212> TYPE: DNA
<213> ORGANISM: Hepatitis C virus
<220> FEATURE:
<221> NAME/KEY: modified_base
<222> LOCATION: (86)..(86)
<223> OTHER INFORMATION: a, c, t or g
<220> FEATURE:
<221> NAME/KEY: modified_base
<222> LOCATION: (434)..(434)
<223> OTHER INFORMATION: a, c, t or g
<220> FEATURE:
<221> NAME/KEY: modified_base
<222> LOCATION: (455)..(455)
<223> OTHER INFORMATION: a, c, t or g
<220> FEATURE:
<221> NAME/KEY: modified_base
<222> LOCATION: (476)..(476)
<223> OTHER INFORMATION: a, c, t or g
<220> FEATURE:
<221> NAME/KEY: modified_base
<222> LOCATION: (488)..(488)
<223> OTHER INFORMATION: a, c, t or g

<400> SEQUENCE: 11
ddatcactcc cctgtgagga actactgtct tcacgcagaa agcgtctagc catggcgtta 60
gtatgagtgt ygtgcagcyt ccaggncccc ccctcccggg agagccatag tggtctgcgg 120
aaccggtgag tacaccggaa ttgccrggah gaccgggtcc tttcttggat daacccgctc 180
watgccygga vatttgggcg tgcccccgcr agacygctag ccgagtagyg ttgggtygcg 240
aaaggccttg tggtactgcc tgatagggtg cttgcgagtg ccccgggagg tctcgtagac 300
cgtgcahcat gagcacrmwt cchaaacchc aaagaaaaac caaamgwaac accaaccgyc 360
gcccacagga cgthaagttc ccgggyggyg ghcagatcgt tggbggagth tacbtgttgc 420
cgcgcagggg cccnmvdttg ggtgtgcgcg cgacnaggaa gacttcbgar cggtcncarc 480 chcghggnag 490

<210> SEQ ID NO 12

-continued

<211> LENGTH: 29
<212> TYPE: DNA
<213> ORGANISM: Hepatitis C virus
<220> FEATURE:
<221> NAME/KEY: modified_base
<222> LOCATION: (6)..(6)
<223> OTHER INFORMATION: a, c, t or g

<400> SEQUENCE: 12
atggcntggg atatgatgat gaactggyc 29

<210> SEQ ID NO 13
<211> LENGTH: 265
<212> TYPE: DNA
<213> ORGANISM: Homo sapiens

<400> SEQUENCE: 13
aaggtcgggc aggaagaggg cctatttccc atgattcctt catatttgca tatacgatac 60
aaggctgtta gagagataat tagaattaat ttgactgtaa acacaaagat attagtacaa 120
aatacgtgac gtagaaagta ataatttctt gggtagtttg cagttttaaa attatgtttt 180
aaaatggact atcatatgct taccgtaact tgaaagtatt tcgatttctt ggctttatat 240
atcttgtgga aaggacgaaa caccg 265

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: eiRNA encoding sequence mapping to HBV-AYW coordinates 788-808 in GenBank accession # V01460

<400> SEQUENCE: 14
cgtctgcgag gcgagggagt tagagaactt aactccctcg cctcgcagac g 51

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: eiRNA encoding sequence mapping to HBV-AYW coordinates 807-827 in GenBank accession # V01460

<400> SEQUENCE: 15
ttcttcttct aggggacctg cagagaactt gcaggtcccc tagaagaaga a 51

<210> SEQ ID NO 16
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: eiRNA encoding sequence mapping to HBV-AYW coordinates 1291-1311 in GenBank accession # V01460

<400> SEQUENCE: 16
aagccaccca aggcacagct tagagaactt aagctgtgcc ttgggtggct t 51

```
<210> SEQ ID NO 17
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: eiRNA encoding sequence mapping to HBV-AYW
      coordinates 1299-1319 in GenBank accession # V01460

<400> SEQUENCE: 17

caaggcacag cttggaggct tagagaactt aagcctccaa gctgtgcctt g              51


<210> SEQ ID NO 18
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: eiRNA encoding sequence mapping to HBV-AYW
      coordinates 1737-1757 in GenBank accession # V01460

<400> SEQUENCE: 18

ggattcagcg ccgacgggac gagagaactt cgtcccgtcg gcgctgaatc c              51


<210> SEQ ID NO 19
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: eiRNA encoding sequence mapping to HBV-AYW
      coordinates 1907-1927 in GenBank accession # V01460

<400> SEQUENCE: 19

ttccgcagta tggatcggca gagagaactt ctgccgatcc atactgcgga a              51


<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: eiRNA encoding sequence mapping to HBV-AYW
      coordinates 1912-1932 in GenBank accession # V01460

<400> SEQUENCE: 20

cagtatggat cggcagagga gagagaactt ctcctctgcc gatccatact g              51


<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: eiRNA encoding sequence mapping to HBV-AYW
      coordinates 1943-1963 in GenBank accession # V01460

<400> SEQUENCE: 21

tccacgcatg cgctgatggc cagagaactt ggccatcagc gcatgcgtgg a              51
```

<210> SEQ ID NO 22
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: eiRNA encoding sequence mapping to HBV-AYW
coordinates 1991-2011 in GenBank accession # V01460

<400> SEQUENCE: 22
tgcgtcagca aacacttggc aagagaactt tgccaagtgt ttgctgacgc a 51

<210> SEQ ID NO 23
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: eiRNA encoding sequence mapping to HBV-AYW
coordinates 2791-2811 in GenBank accession # V01460

<400> SEQUENCE: 23
aaaacgccgc agacacatcc aagagaactt tggatgtgtc tgcggcgttt t 51

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: eiRNA encoding sequence mapping to HBV-AYW
coordinates 2791-2811mut in GenBank accession # V01460

<400> SEQUENCE: 24
aaaacaccac acacgcatcc aagagaactt tggatgcgtg tgtggtgttt t 51

<210> SEQ ID NO 25
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: eiRNA encoding sequence mapping to HBV-AYW
coordinates 2912-2932 in GenBank accession # V01460

<400> SEQUENCE: 25
ttgagagaag tccaccacga gagagaactt ctcgtggtgg acttctctca a 51

<210> SEQ ID NO 26
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: eiRNA encoding sequence mapping to HBV-AYW
coordinates 2919-2939 in GenBank accession # V01460

<400> SEQUENCE: 26
aagtccacca cgagtctaga cagagaactt gtctagactc gtggtggact t 51

<210> SEQ ID NO 27
<211> LENGTH: 101
<212> TYPE: DNA
<213> ORGANISM: Hepatitis C virus

<400> SEQUENCE: 27
tttggtggct ccatcttagc cctagtcacg gctagctgtg aaaggtccgt gagccgcttg 60
actgcagaga gtgctgatac tggcctctct gcagatcaag t 101

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: siRNA encoding sequence mapping to X region of Hepatitis C Virus

<400> SEQUENCE: 28
gctaaacact ccaggccaat acctgtctc 29

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: siRNA encoding sequence mapping to X region of Hepatitis C Virus

<400> SEQUENCE: 29
tcctttggtg gctccatctt acctgtctc 29

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: siRNA encoding sequence mapping to X region of Hepatitis C Virus

<400> SEQUENCE: 30
gctccatctt agccctagtc acctgtctc 29

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: siRNA encoding sequence mapping to X region of Hepatitis C Virus

<400> SEQUENCE: 31
tcttagccct agtcacggct acctgtctc 29

<210> SEQ ID NO 32

<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: siRNA encoding sequence mapping to X region of Hepatitis C Virus

<400> SEQUENCE: 32
cctagtcacg gctagctgtg acctgtctc 29

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: siRNA encoding sequence mapping to X region of Hepatitis C Virus

<400> SEQUENCE: 33
ctagtcacgg ctagctgtga acctgtctc 29

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: siRNA encoding sequence mapping to X region of Hepatitis C Virus

<400> SEQUENCE: 34
cgtgagccgc ttgactgcag acctgtctc 29

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: siRNA encoding sequence mapping to X region of Hepatitis C Virus

<400> SEQUENCE: 35
gctgatactg gcctctctgc acctgtctc 29

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: siRNA encoding sequence mapping to X region of Hepatitis C Virus

<400> SEQUENCE: 36
actggcctct ctgcagatca acctgtctc 29

-continued

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: siRNA encoding sequence mapping to X region of Hepatitis C Virus

<400> SEQUENCE: 37
ctggcctctc tgcagatcaa g 21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: siRNA encoding sequence mapping to X region of Hepatitis C Virus

<400> SEQUENCE: 38
tgcagagagt gctgatactg g 21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: siRNA encoding sequence mapping to X region of Hepatitis C Virus

<400> SEQUENCE: 39
tgagccgctt gactgcagag a 21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: siRNA encoding sequence mapping to X region of Hepatitis C Virus

<400> SEQUENCE: 40
gaaaggtccg tgagccgctt 20

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: siRNA encoding sequence mapping to X region of Hepatitis C Virus

<400> SEQUENCE: 41
tagctgtgaa aggtccgtga g 21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: siRNA encoding sequence mapping to X region of Hepatitis C Virus

<400> SEQUENCE: 42
ttagccctag tcacggctag c 21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: siRNA encoding sequence mapping to X region of Hepatitis C Virus

<400> SEQUENCE: 43
tccatcttag ccctagtcac g 21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: siRNA encoding sequence mapping to X region of Hepatitis C Virus

<400> SEQUENCE: 44
ttggtggctc catcttagcc c 21

<210> SEQ ID NO 45
<211> LENGTH: 21
<212> TYPE: RNA
<213> ORGANISM: Hepatitis C virus

<400> SEQUENCE: 45
aaccucaaag aaaaaccaaa c 21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: lamin siRNA

<400> SEQUENCE: 46
aacuggacuu ccagaagaac a 21

<210> SEQ ID NO 47
<211> LENGTH: 2652
<212> TYPE: DNA
<213> ORGANISM: Bacteriophage T7

-continued

<400> SEQUENCE: 47

```
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag gacatccctg cgattgagcg tgaagaactc   1080
ccgatgaaac cggaagacat cgacatgaat cctgaggctc tcaccgcgtg gaaacgtgct   1140
gccgctgctg tgtaccgcaa ggacagggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagata ttattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
```

-continued aactttgtac acagccaaga cggtagccac cttcgtaaga ctgtagtgtg ggcacacgag 2400
aagtacggaa tcgaatcttt tgcactgatt cacgactcct tcggtaccat tccggctgac 2460
gctgcgaacc tgttcaaagc agtgcgcgaa actatggttg acacatatga gtcttgtgat 2520
gtactggctg atttctacga ccagttcgct gaccagttgc acgagtctca attggacaaa 2580
atgccagcac ttccggctaa aggtaacttg aacctccgtg acatcttaga gtcggacttc 2640
gcgttcgcgt aa 2652

<210> SEQ ID NO 48
<211> LENGTH: 323
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: T7 polymerase-based eiRNA

<400> SEQUENCE: 48
atcactcccc tgtgaggaac tactgtcttc acgcagaaag cgtctagcca tggcgttagt 60
atgagtgtcg tgcagcctcc aggacccccc ctcccgggag agccatagtg gtctgcggaa 120
ccggtgagta caccggaatt gccaggacga ccgggtcctt tcttggatga acccgctcaa 180
tgcctggaga tttgggcgtg cccccgcgag actgctagcc gagtagtgtt gggtcgcgaa 240
aggccttgtg gtactgcctg atagggtgct tgcgagtgcc ccgggaggtc tcgtagaccg 300
tgcaccatga gcacaaatcc taa 323

<210> SEQ ID NO 49
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: eiRNA encoding sequence mapping to HBV-AYW
coordinates 799-779 in GenBank accession # V01460

<400> SEQUENCE: 49
gcctcgcaga cgaaggtctc aagagaactt tgagaccttc gtctgcgagg c 51

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: eiRNA encoding sequence mapping to HBV-AYW
coordinates 788-808 in GenBank accession # V01460

<400> SEQUENCE: 50
cgtctgcgag gcgagggagt t 21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:

-continued

<223> OTHER INFORMATION: eiRNA encoding sequence mapping to HBV-AYW coordinates 807-827 in GenBank accession # V01460

<400> SEQUENCE: 51
ttcttcttct aggggacctg c 21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: eiRNA encoding sequence mapping to HBV-AYW coordinates 1291-1311 in GenBank accession # V01460

<400> SEQUENCE: 52
aagccaccca aggcacagct t 21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: eiRNA encoding sequence mapping to HBV-AYW coordinates 1299-1319 in GenBank accession # V01460

<400> SEQUENCE: 53
caaggcacag cttggaggct t 21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: eiRNA encoding sequence mapping to HBV-AYW coordinates 1737-1757 in GenBank accession # V01460

<400> SEQUENCE: 54
ggattcagcg ccgacgggac g 21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: eiRNA encoding sequence mapping to HBV-AYW coordinates 1907-1927 in GenBank accession # V01460

<400> SEQUENCE: 55
ttccgcagta tggatcggca g 21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide -continued
<220> FEATURE:
<223> OTHER INFORMATION: eiRNA encoding sequence mapping to HBV-AYW
coordinates 1912-1932 in GenBank accession # V01460

<400> SEQUENCE: 56
cagtatggat cggcagagga g 21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: eiRNA encoding sequence mapping to HBV-AYW
coordinates 1943-1963 in GenBank accession # V01460

<400> SEQUENCE: 57
tccacgcatg cgctgatggc c 21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: eiRNA encoding sequence mapping to HBV-AYW
coordinates 1991-2011 in GenBank accession # V01460

<400> SEQUENCE: 58
tgcgtcagca aacacttggc a 21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: eiRNA encoding sequence mapping to HBV-AYW
coordinates 2791-2811 in GenBank accession # V01460

<400> SEQUENCE: 59
aaaacgccgc agacacatcc a 21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: eiRNA encoding sequence mapping to HBV-AYW
coordinates 2912-2932 in GenBank accession # V01460

<400> SEQUENCE: 60
ttgagagaag tccaccacga g 21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic -continued

```
      oligonucleotide
<220> FEATURE:
<223> OTHER INFORMATION: eiRNA encoding sequence mapping to HBV-AYW
      coordinates 2919-2939 in GenBank accession # V01460

<400> SEQUENCE: 61

aagtccacca cgagtctaga c                                              21


<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: eiRNA encoding sequence mapping to HBV-AYW
      coordinates 799-779 in GenBank accession # V01460

<400> SEQUENCE: 62

gcctcgcaga cgaaggtctc a                                              21


<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: siRNA encoding sequence mapping to X region of
      Hepatitis C Virus

<400> SEQUENCE: 63

gctaaacact ccaggccaat a                                              21


<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: siRNA encoding sequence mapping to X region of
      Hepatitis C Virus

<400> SEQUENCE: 64

tcctttggtg gctccatctt a                                              21


<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: siRNA encoding sequence mapping to X region of
      Hepatitis C Virus

<400> SEQUENCE: 65

gctccatctt agccctagtc a                                              21


<210> SEQ ID NO 66
<211> LENGTH: 21
<212> TYPE: DNA
<213> ORGANISM: Artificial Sequence
<220> FEATURE:
```

<223> OTHER INFORMATION: Description of Artificial Sequence: Synthetic
oligonucleotide
<220> FEATURE:
<223> OTHER INFORMATION: siRNA encoding sequence mapping to X region of
Hepatitis C Virus

<400> SEQUENCE: 66
tcttagccct agtcacggct a 21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: siRNA encoding sequence mapping to X region of
Hepatitis C Virus

<400> SEQUENCE: 67
cctagtcacg gctagctgtg a 21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: siRNA encoding sequence mapping to X region of
Hepatitis C Virus

<400> SEQUENCE: 68
ctagtcacgg ctagctgtga a 21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: siRNA encoding sequence mapping to X region of
Hepatitis C Virus

<400> SEQUENCE: 69
cgtgagccgc ttgactgcag a 21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: siRNA encoding sequence mapping to X region of
Hepatitis C Virus

<400> SEQUENCE: 70
gctgatactg gcctctctgc a 21

<210> SEQ ID NO 71
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: siRNA encoding sequence mapping to X region of
      Hepatitis C Virus

<400> SEQUENCE: 71

actggcctct ctgcagatca a                                              21


<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HCV5M-5.1 dsRNA

<400> SEQUENCE: 72

aaaggccttg tggtactgcc t                                              21


<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HCV5M-5.3 dsRNA

<400> SEQUENCE: 73

ttgtggtact gcctgatagg g                                              21


<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HCVXM-13 dsRNA

<400> SEQUENCE: 74

tagctgtgaa aggtccgtga g                                              21


<210> SEQ ID NO 75
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HCVXM-34 dsRNA

<400> SEQUENCE: 75

atcttagccc tagtcacggc tagctg                                         26


<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: HCVXM-35 dsRNA

<400> SEQUENCE: 76

tagtcacggc tagctgtgaa aggtccg                                          27


<210> SEQ ID NO 77
<211> LENGTH: 21
<212> TYPE: DNA
<213> ORGANISM: Hepatitis C virus

<400> SEQUENCE: 77

cctgtgagga actactgtct t                                                21


<210> SEQ ID NO 78
<211> LENGTH: 21
<212> TYPE: DNA
<213> ORGANISM: Hepatitis C virus

<400> SEQUENCE: 78

acgcagaaag cgtctagcca t                                                21


<210> SEQ ID NO 79
<211> LENGTH: 21
<212> TYPE: DNA
<213> ORGANISM: Hepatitis C virus

<400> SEQUENCE: 79

cgtctagcca tggcgttagt a                                                21


<210> SEQ ID NO 80
<211> LENGTH: 21
<212> TYPE: DNA
<213> ORGANISM: Hepatitis C virus

<400> SEQUENCE: 80

gtctagccat ggcgttagta t                                                21


<210> SEQ ID NO 81
<211> LENGTH: 25
<212> TYPE: DNA
<213> ORGANISM: Hepatitis C virus

<400> SEQUENCE: 81

ctcccctgtg aggaactact gtctt                                            25


<210> SEQ ID NO 82
<211> LENGTH: 25
<212> TYPE: DNA
<213> ORGANISM: Hepatitis C virus

<400> SEQUENCE: 82

gaggaactac tgtcttcacg cagaa                                            25


<210> SEQ ID NO 83
<211> LENGTH: 27
<212> TYPE: DNA
<213> ORGANISM: Hepatitis C virus

<400> SEQUENCE: 83

gtgaggaact actgtcttca cgcagaa                                          27


<210> SEQ ID NO 84
```

<211> LENGTH: 21
<212> TYPE: DNA
<213> ORGANISM: Hepatitis C virus

<400> SEQUENCE: 84
gagccatagt ggtctgcgga a 21

<210> SEQ ID NO 85
<211> LENGTH: 21
<212> TYPE: DNA
<213> ORGANISM: Hepatitis C virus

<400> SEQUENCE: 85
gaaccggtga gtacaccgga a 21

<210> SEQ ID NO 86
<211> LENGTH: 21
<212> TYPE: DNA
<213> ORGANISM: Hepatitis C virus

<400> SEQUENCE: 86
accggtgagt acaccggaat t 21

<210> SEQ ID NO 87
<211> LENGTH: 25
<212> TYPE: DNA
<213> ORGANISM: Hepatitis C virus

<400> SEQUENCE: 87
gggagagcca tagtggtctg cggaa 25

<210> SEQ ID NO 88
<211> LENGTH: 21
<212> TYPE: DNA
<213> ORGANISM: Hepatitis C virus

<400> SEQUENCE: 88
ggccttgtgg tactgcctga t 21

<210> SEQ ID NO 89
<211> LENGTH: 21
<212> TYPE: DNA
<213> ORGANISM: Hepatitis C virus

<400> SEQUENCE: 89
gccttgtggt actgcctgat a 21

<210> SEQ ID NO 90
<211> LENGTH: 21
<212> TYPE: DNA
<213> ORGANISM: Hepatitis C virus

<400> SEQUENCE: 90
gtactgcctg atagggtgct t 21

<210> SEQ ID NO 91
<211> LENGTH: 27
<212> TYPE: DNA
<213> ORGANISM: Hepatitis C virus

<400> SEQUENCE: 91
aaggccttgt ggtactgcct gataggg 27

<210> SEQ ID NO 92
<211> LENGTH: 27
<212> TYPE: DNA
<213> ORGANISM: Hepatitis C virus

<400> SEQUENCE: 92
cgaaaggcct tgtggtactg cctgata 27

<210> SEQ ID NO 93
<211> LENGTH: 27
<212> TYPE: DNA
<213> ORGANISM: Hepatitis C virus

<400> SEQUENCE: 93
cttgcgagtg ccccgggagg tctcgta 27

<210> SEQ ID NO 94
<211> LENGTH: 21
<212> TYPE: DNA
<213> ORGANISM: Hepatitis C virus

<400> SEQUENCE: 94
atcactcccc tgtgaggaac t 21

<210> SEQ ID NO 95
<211> LENGTH: 21
<212> TYPE: DNA
<213> ORGANISM: Hepatitis C virus

<400> SEQUENCE: 95
ttcacgcaga aagcgtctag c 21

<210> SEQ ID NO 96
<211> LENGTH: 21
<212> TYPE: DNA
<213> ORGANISM: Hepatitis C virus

<400> SEQUENCE: 96
tagccatggc gttagtatga g 21

<210> SEQ ID NO 97
<211> LENGTH: 25
<212> TYPE: DNA
<213> ORGANISM: Hepatitis C virus

<400> SEQUENCE: 97
atcactcccc tgtgaggaac tactg 25

<210> SEQ ID NO 98
<211> LENGTH: 27
<212> TYPE: DNA
<213> ORGANISM: Hepatitis C virus

<400> SEQUENCE: 98
atcactcccc tgtgaggaac tactgtc 27

<210> SEQ ID NO 99
<211> LENGTH: 25
<212> TYPE: DNA
<213> ORGANISM: Hepatitis C virus

<400> SEQUENCE: 99
aactactgtc ttcacgcaga aagcg 25

<210> SEQ ID NO 100
<211> LENGTH: 27
<212> TYPE: DNA
<213> ORGANISM: Hepatitis C virus

<400> SEQUENCE: 100
aactactgtc ttcacgcaga aagcgtc 27

<210> SEQ ID NO 101
<211> LENGTH: 21
<212> TYPE: DNA
<213> ORGANISM: Hepatitis C virus

<400> SEQUENCE: 101
atagtggtct gcggaaccgg t 21

<210> SEQ ID NO 102
<211> LENGTH: 21
<212> TYPE: DNA
<213> ORGANISM: Hepatitis C virus

<400> SEQUENCE: 102
tagtggtctg cggaaccggt g 21

<210> SEQ ID NO 103
<211> LENGTH: 25
<212> TYPE: DNA
<213> ORGANISM: Hepatitis C virus

<400> SEQUENCE: 103
aaccggtgag tacaccggaa ttgcc 25

<210> SEQ ID NO 104
<211> LENGTH: 21
<212> TYPE: DNA
<213> ORGANISM: Hepatitis C virus

<400> SEQUENCE: 104
aaggccttgt ggtactgcct g 21

<210> SEQ ID NO 105
<211> LENGTH: 21
<212> TYPE: DNA
<213> ORGANISM: Hepatitis C virus

<400> SEQUENCE: 105
tactgcctga tagggtgctt g 21

<210> SEQ ID NO 106
<211> LENGTH: 27
<212> TYPE: DNA
<213> ORGANISM: Hepatitis C virus

<400> SEQUENCE: 106
ttgtggtact gcctgatagg gtgcttg 27

<210> SEQ ID NO 107
<211> LENGTH: 25
<212> TYPE: DNA
<213> ORGANISM: Hepatitis C virus

<400> SEQUENCE: 107
tactgcctga tagggtgctt gcgag 25

<210> SEQ ID NO 108
<211> LENGTH: 24
<212> TYPE: DNA
<213> ORGANISM: Hepatitis C virus

<400> SEQUENCE: 108
tagggtgctt gcgagtgccc cggg 24

<210> SEQ ID NO 109
<211> LENGTH: 27
<212> TYPE: DNA
<213> ORGANISM: Hepatitis C virus

<400> SEQUENCE: 109
ttgcgagtgc cccgggaggt ctcgtag 27

<210> SEQ ID NO 110
<211> LENGTH: 52
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (23)..(31)
<223> OTHER INFORMATION: a, c, u, g, unknown or other

<400> SEQUENCE: 110
aaagguccgu gagccgcuug acnnnnnnnn ngucaagcgg ucacggaccu uu 52

<210> SEQ ID NO 111
<211> LENGTH: 206
<212> TYPE: DNA
<213> ORGANISM: Hepatitis B virus
<220> FEATURE:
<221> NAME/KEY: modified_base
<222> LOCATION: (63)..(63)
<223> OTHER INFORMATION: a, c, t or g
<220> FEATURE:
<221> NAME/KEY: modified_base
<222> LOCATION: (111)..(111)
<223> OTHER INFORMATION: a, c, t or g
<220> FEATURE:
<221> NAME/KEY: modified_base
<222> LOCATION: (140)..(140)
<223> OTHER INFORMATION: a, c, t or g
<220> FEATURE:
<221> NAME/KEY: modified_base
<222> LOCATION: (174)..(174)
<223> OTHER INFORMATION: a, c, t or g
<220> FEATURE:
<221> NAME/KEY: modified_base
<222> LOCATION: (177)..(177)
<223> OTHER INFORMATION: a, c, t or g

<400> SEQUENCE: 111
aaggcctttc tvhgtmaaca rtaymtgmmc atttaccccg ttgcymggca acggychggy 60
ctntgccaag tgtttgctga cgcaaccccc actgghtggg gcttggybat nggccatcrs 120
cgcatgcgtg gaacctttbn gkctcctctg ccgatccata ctgcggaact cctngcngcb 180
tgtttygctc gcagcmggtc tggrgc 206

<210> SEQ ID NO 112
<211> LENGTH: 489
<212> TYPE: DNA
<213> ORGANISM: Hepatitis C virus

```
<220> FEATURE:
<221> NAME/KEY: modified_base
<222> LOCATION: (86)..(86)
<223> OTHER INFORMATION: a, c, t or g
<220> FEATURE:
<221> NAME/KEY: modified_base
<222> LOCATION: (433)..(433)
<223> OTHER INFORMATION: a, c, t or g
<220> FEATURE:
<221> NAME/KEY: modified_base
<222> LOCATION: (454)..(454)
<223> OTHER INFORMATION: a, c, t or g
<220> FEATURE:
<221> NAME/KEY: modified_base
<222> LOCATION: (475)..(475)
<223> OTHER INFORMATION: a, c, t or g
<220> FEATURE:
<221> NAME/KEY: modified_base
<222> LOCATION: (487)..(487)
<223> OTHER INFORMATION: a, c, t or g

<400> SEQUENCE: 112

ddatcactcc cctgtgagga actactgtct tcacgcagaa agcgtctagc catggcgtta     60

gtatgagtgt ygtgcagcyt ccaggncccc ccctcccggg agagccatag tggtctgcgg    120

aaccggtgag tacaccggaa ttgccrggah gaccgggtcc tttcttggat daacccgctc    180

watgccygga vatttgggcg tgcccccgcr agacygctag ccgagtagyg ttgggtygcg    240

aaaggccttg tggtactgcc tgatagggtg cttgcgagtg ccccgggagg tctcgtagac    300

cgtgcahcat gagcacrmwt cchaaacchc aaagaaaaac caaamgwaac accaaccgyc    360

gcccacagga cgthaagtmc cgggyggygg hcagatcgtt ggbggagtht acbtgttgcc    420

gcgcaggggc ccnmvdttgg gtgtgcgcgc gacnaggaag acttcbgarc ggtcncarcc    480

hcghggnag                                                            489


<210> SEQ ID NO 113
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113

gccucgcaga cgaaggucuc aagagaacuu ugagaccuuc gucugcgagg c              51


<210> SEQ ID NO 114
<211> LENGTH: 20
<212> TYPE: DNA
<213> ORGANISM: Hepatitis C virus

<400> SEQUENCE: 114

accggtgagt acaccggaat                                                 20


<210> SEQ ID NO 115
<211> LENGTH: 22
<212> TYPE: DNA
<213> ORGANISM: Hepatitis C virus

<400> SEQUENCE: 115

tggctccatc ttagccctag tc                                              22


<210> SEQ ID NO 116
<211> LENGTH: 24
<212> TYPE: DNA
<213> ORGANISM: Hepatitis C virus
```

<400> SEQUENCE: 116
tggctccatc ttagccctag tcac 24

<210> SEQ ID NO 117
<211> LENGTH: 25
<212> TYPE: DNA
<213> ORGANISM: Hepatitis C virus

<400> SEQUENCE: 117
tggctccatc ttagccctag tcacg 25

<210> SEQ ID NO 118
<211> LENGTH: 26
<212> TYPE: DNA
<213> ORGANISM: Hepatitis C virus

<400> SEQUENCE: 118
tggctccatc ttagccctag tcacgg 26

<210> SEQ ID NO 119
<211> LENGTH: 27
<212> TYPE: DNA
<213> ORGANISM: Hepatitis C virus

<400> SEQUENCE: 119
tggctccatc ttagccctag tcacggc 27

<210> SEQ ID NO 120
<211> LENGTH: 21
<212> TYPE: DNA
<213> ORGANISM: Hepatitis C virus

<400> SEQUENCE: 120
tccatcttag ccctagtcac g 21

<210> SEQ ID NO 121
<211> LENGTH: 22
<212> TYPE: DNA
<213> ORGANISM: Hepatitis C virus

<400> SEQUENCE: 121
tccatcttag ccctagtcac gg 22

<210> SEQ ID NO 122
<211> LENGTH: 23
<212> TYPE: DNA
<213> ORGANISM: Hepatitis C virus

<400> SEQUENCE: 122
tccatcttag ccctagtcac ggc 23

<210> SEQ ID NO 123
<211> LENGTH: 26
<212> TYPE: DNA
<213> ORGANISM: Hepatitis C virus

<400> SEQUENCE: 123
tccatcttag ccctagtcac ggctag 26

<210> SEQ ID NO 124
<211> LENGTH: 27
<212> TYPE: DNA

<213> ORGANISM: Hepatitis C virus

<400> SEQUENCE: 124
tccatcttag ccctagtcac ggctagc 27

<210> SEQ ID NO 125
<211> LENGTH: 29
<212> TYPE: DNA
<213> ORGANISM: Hepatitis C virus

<400> SEQUENCE: 125
tccatcttag ccctagtcac ggctagctg 29

<210> SEQ ID NO 126
<211> LENGTH: 23
<212> TYPE: DNA
<213> ORGANISM: Hepatitis C virus

<400> SEQUENCE: 126
atcttagccc tagtcacggc tag 23

<210> SEQ ID NO 127
<211> LENGTH: 24
<212> TYPE: DNA
<213> ORGANISM: Hepatitis C virus

<400> SEQUENCE: 127
atcttagccc tagtcacggc tagc 24

<210> SEQ ID NO 128
<211> LENGTH: 26
<212> TYPE: DNA
<213> ORGANISM: Hepatitis C virus

<400> SEQUENCE: 128
atcttagccc tagtcacggc tagctg 26

<210> SEQ ID NO 129
<211> LENGTH: 28
<212> TYPE: DNA
<213> ORGANISM: Hepatitis C virus

<400> SEQUENCE: 129
atcttagccc tagtcacggc tagctgtg 28

<210> SEQ ID NO 130
<211> LENGTH: 22
<212> TYPE: DNA
<213> ORGANISM: Hepatitis C virus

<400> SEQUENCE: 130
tcttagccct agtcacggct ag 22

<210> SEQ ID NO 131
<211> LENGTH: 23
<212> TYPE: DNA
<213> ORGANISM: Hepatitis C virus

<400> SEQUENCE: 131
tcttagccct agtcacggct agc 23

<210> SEQ ID NO 132
<211> LENGTH: 25

-continued

<212> TYPE: DNA
<213> ORGANISM: Hepatitis C virus

<400> SEQUENCE: 132
tcttagccct agtcacggct agctg 25

<210> SEQ ID NO 133
<211> LENGTH: 27
<212> TYPE: DNA
<213> ORGANISM: Hepatitis C virus

<400> SEQUENCE: 133
tcttagccct agtcacggct agctgtg 27

<210> SEQ ID NO 134
<211> LENGTH: 21
<212> TYPE: DNA
<213> ORGANISM: Hepatitis C virus

<400> SEQUENCE: 134
ttagccctag tcacggctag c 21

<210> SEQ ID NO 135
<211> LENGTH: 23
<212> TYPE: DNA
<213> ORGANISM: Hepatitis C virus

<400> SEQUENCE: 135
ttagccctag tcacggctag ctg 23

<210> SEQ ID NO 136
<211> LENGTH: 25
<212> TYPE: DNA
<213> ORGANISM: Hepatitis C virus

<400> SEQUENCE: 136
ttagccctag tcacggctag ctgtg 25

<210> SEQ ID NO 137
<211> LENGTH: 29
<212> TYPE: DNA
<213> ORGANISM: Hepatitis C virus

<400> SEQUENCE: 137
ttagccctag tcacggctag ctgtgaaag 29

<210> SEQ ID NO 138
<211> LENGTH: 22
<212> TYPE: DNA
<213> ORGANISM: Hepatitis C virus

<400> SEQUENCE: 138
tagccctagt cacggctagc tg 22

<210> SEQ ID NO 139
<211> LENGTH: 24
<212> TYPE: DNA
<213> ORGANISM: Hepatitis C virus

<400> SEQUENCE: 139
tagccctagt cacggctagc tgtg 24

<210> SEQ ID NO 140

<211> LENGTH: 28
<212> TYPE: DNA
<213> ORGANISM: Hepatitis C virus

<400> SEQUENCE: 140
tagccctagt cacggctagc tgtgaaag 28

<210> SEQ ID NO 141
<211> LENGTH: 29
<212> TYPE: DNA
<213> ORGANISM: Hepatitis C virus

<400> SEQUENCE: 141
tagccctagt cacggctagc tgtgaaagg 29

<210> SEQ ID NO 142
<211> LENGTH: 21
<212> TYPE: DNA
<213> ORGANISM: Hepatitis C virus

<400> SEQUENCE: 142
agccctagtc acggctagct g 21

<210> SEQ ID NO 143
<211> LENGTH: 23
<212> TYPE: DNA
<213> ORGANISM: Hepatitis C virus

<400> SEQUENCE: 143
agccctagtc acggctagct gtg 23

<210> SEQ ID NO 144
<211> LENGTH: 27
<212> TYPE: DNA
<213> ORGANISM: Hepatitis C virus

<400> SEQUENCE: 144
agccctagtc acggctagct gtgaaag 27

<210> SEQ ID NO 145
<211> LENGTH: 28
<212> TYPE: DNA
<213> ORGANISM: Hepatitis C virus

<400> SEQUENCE: 145
agccctagtc acggctagct gtgaaagg 28

<210> SEQ ID NO 146
<211> LENGTH: 22
<212> TYPE: DNA
<213> ORGANISM: Hepatitis C virus

<400> SEQUENCE: 146
tagtcacggc tagctgtgaa ag 22

<210> SEQ ID NO 147
<211> LENGTH: 23
<212> TYPE: DNA
<213> ORGANISM: Hepatitis C virus

<400> SEQUENCE: 147
tagtcacggc tagctgtgaa agg 23

<210> SEQ ID NO 148
<211> LENGTH: 25
<212> TYPE: DNA
<213> ORGANISM: Hepatitis C virus

<400> SEQUENCE: 148
tagtcacggc tagctgtgaa aggtc 25

<210> SEQ ID NO 149
<211> LENGTH: 26
<212> TYPE: DNA
<213> ORGANISM: Hepatitis C virus

<400> SEQUENCE: 149
tagtcacggc tagctgtgaa aggtcc 26

<210> SEQ ID NO 150
<211> LENGTH: 27
<212> TYPE: DNA
<213> ORGANISM: Hepatitis C virus

<400> SEQUENCE: 150
tagtcacggc tagctgtgaa aggtccg 27

<210> SEQ ID NO 151
<211> LENGTH: 29
<212> TYPE: DNA
<213> ORGANISM: Hepatitis C virus

<400> SEQUENCE: 151
tagtcacggc tagctgtgaa aggtccgtg 29

<210> SEQ ID NO 152
<211> LENGTH: 21
<212> TYPE: DNA
<213> ORGANISM: Hepatitis C virus

<400> SEQUENCE: 152
agtcacggct agctgtgaaa g 21

<210> SEQ ID NO 153
<211> LENGTH: 22
<212> TYPE: DNA
<213> ORGANISM: Hepatitis C virus

<400> SEQUENCE: 153
agtcacggct agctgtgaaa gg 22

<210> SEQ ID NO 154
<211> LENGTH: 24
<212> TYPE: DNA
<213> ORGANISM: Hepatitis C virus

<400> SEQUENCE: 154
agtcacggct agctgtgaaa ggtc 24

<210> SEQ ID NO 155
<211> LENGTH: 25
<212> TYPE: DNA
<213> ORGANISM: Hepatitis C virus

<400> SEQUENCE: 155
agtcacggct agctgtgaaa ggtcc 25

```
<210> SEQ ID NO 156
<211> LENGTH: 26
<212> TYPE: DNA
<213> ORGANISM: Hepatitis C virus

<400> SEQUENCE: 156

agtcacggct agctgtgaaa ggtccg                                          26


<210> SEQ ID NO 157
<211> LENGTH: 28
<212> TYPE: DNA
<213> ORGANISM: Hepatitis C virus

<400> SEQUENCE: 157

agtcacggct agctgtgaaa ggtccgtg                                        28


<210> SEQ ID NO 158
<211> LENGTH: 22
<212> TYPE: DNA
<213> ORGANISM: Hepatitis C virus

<400> SEQUENCE: 158

tcacggctag ctgtgaaagg tc                                              22


<210> SEQ ID NO 159
<211> LENGTH: 23
<212> TYPE: DNA
<213> ORGANISM: Hepatitis C virus

<400> SEQUENCE: 159

tcacggctag ctgtgaaagg tcc                                             23


<210> SEQ ID NO 160
<211> LENGTH: 24
<212> TYPE: DNA
<213> ORGANISM: Hepatitis C virus

<400> SEQUENCE: 160

tcacggctag ctgtgaaagg tccg                                            24


<210> SEQ ID NO 161
<211> LENGTH: 26
<212> TYPE: DNA
<213> ORGANISM: Hepatitis C virus

<400> SEQUENCE: 161

tcacggctag ctgtgaaagg tccgtg                                          26


<210> SEQ ID NO 162
<211> LENGTH: 28
<212> TYPE: DNA
<213> ORGANISM: Hepatitis C virus

<400> SEQUENCE: 162

tcacggctag ctgtgaaagg tccgtgag                                        28


<210> SEQ ID NO 163
<211> LENGTH: 29
<212> TYPE: DNA
<213> ORGANISM: Hepatitis C virus

<400> SEQUENCE: 163

tcacggctag ctgtgaaagg tccgtgagc                                       29
```

<210> SEQ ID NO 164
<211> LENGTH: 21
<212> TYPE: DNA
<213> ORGANISM: Hepatitis C virus

<400> SEQUENCE: 164
acggctagct gtgaaaggtc c 21

<210> SEQ ID NO 165
<211> LENGTH: 22
<212> TYPE: DNA
<213> ORGANISM: Hepatitis C virus

<400> SEQUENCE: 165
acggctagct gtgaaaggtc cg 22

<210> SEQ ID NO 166
<211> LENGTH: 24
<212> TYPE: DNA
<213> ORGANISM: Hepatitis C virus

<400> SEQUENCE: 166
acggctagct gtgaaaggtc cgtg 24

<210> SEQ ID NO 167
<211> LENGTH: 26
<212> TYPE: DNA
<213> ORGANISM: Hepatitis C virus

<400> SEQUENCE: 167
acggctagct gtgaaaggtc cgtgag 26

<210> SEQ ID NO 168
<211> LENGTH: 27
<212> TYPE: DNA
<213> ORGANISM: Hepatitis C virus

<400> SEQUENCE: 168
acggctagct gtgaaaggtc cgtgagc 27

<210> SEQ ID NO 169
<211> LENGTH: 28
<212> TYPE: DNA
<213> ORGANISM: Hepatitis C virus

<400> SEQUENCE: 169
acggctagct gtgaaaggtc cgtgagcc 28

<210> SEQ ID NO 170
<211> LENGTH: 29
<212> TYPE: DNA
<213> ORGANISM: Hepatitis C virus

<400> SEQUENCE: 170
acggctagct gtgaaaggtc cgtgagccg 29

<210> SEQ ID NO 171
<211> LENGTH: 21
<212> TYPE: DNA
<213> ORGANISM: Hepatitis C virus

<400> SEQUENCE: 171
tagctgtgaa aggtccgtga g 21

<210> SEQ ID NO 172
<211> LENGTH: 22
<212> TYPE: DNA
<213> ORGANISM: Hepatitis C virus

<400> SEQUENCE: 172
tagctgtgaa aggtccgtga gc 22

<210> SEQ ID NO 173
<211> LENGTH: 23
<212> TYPE: DNA
<213> ORGANISM: Hepatitis C virus

<400> SEQUENCE: 173
tagctgtgaa aggtccgtga gcc 23

<210> SEQ ID NO 174
<211> LENGTH: 24
<212> TYPE: DNA
<213> ORGANISM: Hepatitis C virus

<400> SEQUENCE: 174
tagctgtgaa aggtccgtga gccg 24

<210> SEQ ID NO 175
<211> LENGTH: 25
<212> TYPE: DNA
<213> ORGANISM: Hepatitis C virus

<400> SEQUENCE: 175
tagctgtgaa aggtccgtga gccgc 25

<210> SEQ ID NO 176
<211> LENGTH: 28
<212> TYPE: DNA
<213> ORGANISM: Hepatitis C virus

<400> SEQUENCE: 176
tagctgtgaa aggtccgtga gccgcttg 28

<210> SEQ ID NO 177
<211> LENGTH: 21
<212> TYPE: DNA
<213> ORGANISM: Hepatitis C virus

<400> SEQUENCE: 177
agctgtgaaa ggtccgtgag c 21

<210> SEQ ID NO 178
<211> LENGTH: 22
<212> TYPE: DNA
<213> ORGANISM: Hepatitis C virus

<400> SEQUENCE: 178
agctgtgaaa ggtccgtgag cc 22

<210> SEQ ID NO 179
<211> LENGTH: 23
<212> TYPE: DNA
<213> ORGANISM: Hepatitis C virus

<400> SEQUENCE: 179
agctgtgaaa ggtccgtgag ccg 23

<210> SEQ ID NO 180
<211> LENGTH: 24
<212> TYPE: DNA
<213> ORGANISM: Hepatitis C virus

<400> SEQUENCE: 180
agctgtgaaa ggtccgtgag ccgc 24

<210> SEQ ID NO 181
<211> LENGTH: 27
<212> TYPE: DNA
<213> ORGANISM: Hepatitis C virus

<400> SEQUENCE: 181
agctgtgaaa ggtccgtgag ccgcttg 27

<210> SEQ ID NO 182
<211> LENGTH: 29
<212> TYPE: DNA
<213> ORGANISM: Hepatitis C virus

<400> SEQUENCE: 182
agctgtgaaa ggtccgtgag ccgcttgac 29

<210> SEQ ID NO 183
<211> LENGTH: 21
<212> TYPE: DNA
<213> ORGANISM: Hepatitis C virus

<400> SEQUENCE: 183
tgtgaaaggt ccgtgagccg c 21

<210> SEQ ID NO 184
<211> LENGTH: 24
<212> TYPE: DNA
<213> ORGANISM: Hepatitis C virus

<400> SEQUENCE: 184
tgtgaaaggt ccgtgagccg cttg 24

<210> SEQ ID NO 185
<211> LENGTH: 26
<212> TYPE: DNA
<213> ORGANISM: Hepatitis C virus

<400> SEQUENCE: 185
tgtgaaaggt ccgtgagccg cttgac 26

<210> SEQ ID NO 186
<211> LENGTH: 28
<212> TYPE: DNA
<213> ORGANISM: Hepatitis C virus

<400> SEQUENCE: 186
tgtgaaaggt ccgtgagccg cttgactg 28

<210> SEQ ID NO 187
<211> LENGTH: 29
<212> TYPE: DNA
<213> ORGANISM: Hepatitis C virus

<400> SEQUENCE: 187
tgtgaaaggt ccgtgagccg cttgactgc 29

<210> SEQ ID NO 188
<211> LENGTH: 22
<212> TYPE: DNA
<213> ORGANISM: Hepatitis C virus

<400> SEQUENCE: 188
tgaaaggtcc gtgagccgct tg 22

<210> SEQ ID NO 189
<211> LENGTH: 24
<212> TYPE: DNA
<213> ORGANISM: Hepatitis C virus

<400> SEQUENCE: 189
tgaaaggtcc gtgagccgct tgac 24

<210> SEQ ID NO 190
<211> LENGTH: 26
<212> TYPE: DNA
<213> ORGANISM: Hepatitis C virus

<400> SEQUENCE: 190
tgaaaggtcc gtgagccgct tgactg 26

<210> SEQ ID NO 191
<211> LENGTH: 27
<212> TYPE: DNA
<213> ORGANISM: Hepatitis C virus

<400> SEQUENCE: 191
tgaaaggtcc gtgagccgct tgactgc 27

<210> SEQ ID NO 192
<211> LENGTH: 29
<212> TYPE: DNA
<213> ORGANISM: Hepatitis C virus

<400> SEQUENCE: 192
tgaaaggtcc gtgagccgct tgactgcag 29

<210> SEQ ID NO 193
<211> LENGTH: 22
<212> TYPE: DNA
<213> ORGANISM: Hepatitis C virus

<400> SEQUENCE: 193
aaaggtccgt gagccgcttg ac 22

<210> SEQ ID NO 194
<211> LENGTH: 24
<212> TYPE: DNA
<213> ORGANISM: Hepatitis C virus

<400> SEQUENCE: 194
aaaggtccgt gagccgcttg actg 24

<210> SEQ ID NO 195
<211> LENGTH: 25
<212> TYPE: DNA
<213> ORGANISM: Hepatitis C virus

<400> SEQUENCE: 195
aaaggtccgt gagccgcttg actgc 25

<210> SEQ ID NO 196
<211> LENGTH: 27
<212> TYPE: DNA
<213> ORGANISM: Hepatitis C virus

<400> SEQUENCE: 196
aaaggtccgt gagccgcttg actgcag 27

<210> SEQ ID NO 197
<211> LENGTH: 29
<212> TYPE: DNA
<213> ORGANISM: Hepatitis C virus

<400> SEQUENCE: 197
aaaggtccgt gagccgcttg actgcagag 29

<210> SEQ ID NO 198
<211> LENGTH: 21
<212> TYPE: DNA
<213> ORGANISM: Hepatitis C virus

<400> SEQUENCE: 198
aaggtccgtg agccgcttga c 21

<210> SEQ ID NO 199
<211> LENGTH: 23
<212> TYPE: DNA
<213> ORGANISM: Hepatitis C virus

<400> SEQUENCE: 199
aaggtccgtg agccgcttga ctg 23

<210> SEQ ID NO 200
<211> LENGTH: 24
<212> TYPE: DNA
<213> ORGANISM: Hepatitis C virus

<400> SEQUENCE: 200
aaggtccgtg agccgcttga ctgc 24

<210> SEQ ID NO 201
<211> LENGTH: 26
<212> TYPE: DNA
<213> ORGANISM: Hepatitis C virus

<400> SEQUENCE: 201
aaggtccgtg agccgcttga ctgcag 26

<210> SEQ ID NO 202
<211> LENGTH: 28
<212> TYPE: DNA
<213> ORGANISM: Hepatitis C virus

<400> SEQUENCE: 202
aaggtccgtg agccgcttga ctgcagag 28

<210> SEQ ID NO 203
<211> LENGTH: 22
<212> TYPE: DNA

-continued

<213> ORGANISM: Hepatitis C virus

<400> SEQUENCE: 203
aggtccgtga gccgcttgac tg 22

<210> SEQ ID NO 204
<211> LENGTH: 23
<212> TYPE: DNA
<213> ORGANISM: Hepatitis C virus

<400> SEQUENCE: 204
aggtccgtga gccgcttgac tgc 23

<210> SEQ ID NO 205
<211> LENGTH: 25
<212> TYPE: DNA
<213> ORGANISM: Hepatitis C virus

<400> SEQUENCE: 205
aggtccgtga gccgcttgac tgcag 25

<210> SEQ ID NO 206
<211> LENGTH: 27
<212> TYPE: DNA
<213> ORGANISM: Hepatitis C virus

<400> SEQUENCE: 206
aggtccgtga gccgcttgac tgcagag 27

<210> SEQ ID NO 207
<211> LENGTH: 29
<212> TYPE: DNA
<213> ORGANISM: Hepatitis C virus

<400> SEQUENCE: 207
aggtccgtga gccgcttgac tgcagagag 29

<210> SEQ ID NO 208
<211> LENGTH: 22
<212> TYPE: DNA
<213> ORGANISM: Hepatitis C virus

<400> SEQUENCE: 208
tccgtgagcc gcttgactgc ag 22

<210> SEQ ID NO 209
<211> LENGTH: 24
<212> TYPE: DNA
<213> ORGANISM: Hepatitis C virus

<400> SEQUENCE: 209
tccgtgagcc gcttgactgc agag 24

<210> SEQ ID NO 210
<211> LENGTH: 26
<212> TYPE: DNA
<213> ORGANISM: Hepatitis C virus

<400> SEQUENCE: 210
tccgtgagcc gcttgactgc agagag 26

<210> SEQ ID NO 211
<211> LENGTH: 28

<212> TYPE: DNA
<213> ORGANISM: Hepatitis C virus

<400> SEQUENCE: 211
tccgtgagcc gcttgactgc agagagtg 28

<210> SEQ ID NO 212
<211> LENGTH: 29
<212> TYPE: DNA
<213> ORGANISM: Hepatitis C virus

<400> SEQUENCE: 212
tccgtgagcc gcttgactgc agagagtgc 29

<210> SEQ ID NO 213
<211> LENGTH: 22
<212> TYPE: DNA
<213> ORGANISM: Hepatitis C virus

<400> SEQUENCE: 213
tgagccgctt gactgcagag ag 22

<210> SEQ ID NO 214
<211> LENGTH: 24
<212> TYPE: DNA
<213> ORGANISM: Hepatitis C virus

<400> SEQUENCE: 214
tgagccgctt gactgcagag agtg 24

<210> SEQ ID NO 215
<211> LENGTH: 25
<212> TYPE: DNA
<213> ORGANISM: Hepatitis C virus

<400> SEQUENCE: 215
tgagccgctt gactgcagag agtgc 25

<210> SEQ ID NO 216
<211> LENGTH: 27
<212> TYPE: DNA
<213> ORGANISM: Hepatitis C virus

<400> SEQUENCE: 216
tgagccgctt gactgcagag agtgctg 27

<210> SEQ ID NO 217
<211> LENGTH: 22
<212> TYPE: DNA
<213> ORGANISM: Hepatitis C virus

<400> SEQUENCE: 217
agccgcttga ctgcagagag tg 22

<210> SEQ ID NO 218
<211> LENGTH: 23
<212> TYPE: DNA
<213> ORGANISM: Hepatitis C virus

<400> SEQUENCE: 218
agccgcttga ctgcagagag tgc 23

<210> SEQ ID NO 219

<211> LENGTH: 25
<212> TYPE: DNA
<213> ORGANISM: Hepatitis C virus

<400> SEQUENCE: 219
agccgcttga ctgcagagag tgctg 25

<210> SEQ ID NO 220
<211> LENGTH: 29
<212> TYPE: DNA
<213> ORGANISM: Hepatitis C virus

<400> SEQUENCE: 220
agccgcttga ctgcagagag tgctgatac 29

<210> SEQ ID NO 221
<211> LENGTH: 23
<212> TYPE: DNA
<213> ORGANISM: Hepatitis C virus

<400> SEQUENCE: 221
ttgactgcag agagtgctga tac 23

<210> SEQ ID NO 222
<211> LENGTH: 25
<212> TYPE: DNA
<213> ORGANISM: Hepatitis C virus

<400> SEQUENCE: 222
ttgactgcag agagtgctga tactg 25

<210> SEQ ID NO 223
<211> LENGTH: 26
<212> TYPE: DNA
<213> ORGANISM: Hepatitis C virus

<400> SEQUENCE: 223
ttgactgcag agagtgctga tactgg 26

<210> SEQ ID NO 224
<211> LENGTH: 27
<212> TYPE: DNA
<213> ORGANISM: Hepatitis C virus

<400> SEQUENCE: 224
ttgactgcag agagtgctga tactggc 27

<210> SEQ ID NO 225
<211> LENGTH: 28
<212> TYPE: DNA
<213> ORGANISM: Hepatitis C virus

<400> SEQUENCE: 225
ttgactgcag agagtgctga tactggcc 28

<210> SEQ ID NO 226
<211> LENGTH: 22
<212> TYPE: DNA
<213> ORGANISM: Hepatitis C virus

<400> SEQUENCE: 226
tgactgcaga gagtgctgat ac 22

<210> SEQ ID NO 227
<211> LENGTH: 24
<212> TYPE: DNA
<213> ORGANISM: Hepatitis C virus

<400> SEQUENCE: 227
tgactgcaga gagtgctgat actg 24

<210> SEQ ID NO 228
<211> LENGTH: 25
<212> TYPE: DNA
<213> ORGANISM: Hepatitis C virus

<400> SEQUENCE: 228
tgactgcaga gagtgctgat actgg 25

<210> SEQ ID NO 229
<211> LENGTH: 26
<212> TYPE: DNA
<213> ORGANISM: Hepatitis C virus

<400> SEQUENCE: 229
tgactgcaga gagtgctgat actggc 26

<210> SEQ ID NO 230
<211> LENGTH: 27
<212> TYPE: DNA
<213> ORGANISM: Hepatitis C virus

<400> SEQUENCE: 230
tgactgcaga gagtgctgat actggcc 27

<210> SEQ ID NO 231
<211> LENGTH: 29
<212> TYPE: DNA
<213> ORGANISM: Hepatitis C virus

<400> SEQUENCE: 231
tgactgcaga gagtgctgat actggcctc 29

<210> SEQ ID NO 232
<211> LENGTH: 22
<212> TYPE: DNA
<213> ORGANISM: Hepatitis C virus

<400> SEQUENCE: 232
actgcagaga gtgctgatac tg 22

<210> SEQ ID NO 233
<211> LENGTH: 23
<212> TYPE: DNA
<213> ORGANISM: Hepatitis C virus

<400> SEQUENCE: 233
actgcagaga gtgctgatac tgg 23

<210> SEQ ID NO 234
<211> LENGTH: 24
<212> TYPE: DNA
<213> ORGANISM: Hepatitis C virus

<400> SEQUENCE: 234
actgcagaga gtgctgatac tggc 24

<210> SEQ ID NO 235
<211> LENGTH: 25
<212> TYPE: DNA
<213> ORGANISM: Hepatitis C virus

<400> SEQUENCE: 235
actgcagaga gtgctgatac tggcc 25

<210> SEQ ID NO 236
<211> LENGTH: 27
<212> TYPE: DNA
<213> ORGANISM: Hepatitis C virus

<400> SEQUENCE: 236
actgcagaga gtgctgatac tggcctc 27

<210> SEQ ID NO 237
<211> LENGTH: 29
<212> TYPE: DNA
<213> ORGANISM: Hepatitis C virus

<400> SEQUENCE: 237
actgcagaga gtgctgatac tggcctctc 29

<210> SEQ ID NO 238
<211> LENGTH: 21
<212> TYPE: DNA
<213> ORGANISM: Hepatitis C virus

<400> SEQUENCE: 238
tgcagagagt gctgatactg g 21

<210> SEQ ID NO 239
<211> LENGTH: 22
<212> TYPE: DNA
<213> ORGANISM: Hepatitis C virus

<400> SEQUENCE: 239
tgcagagagt gctgatactg gc 22

<210> SEQ ID NO 240
<211> LENGTH: 23
<212> TYPE: DNA
<213> ORGANISM: Hepatitis C virus

<400> SEQUENCE: 240
tgcagagagt gctgatactg gcc 23

<210> SEQ ID NO 241
<211> LENGTH: 25
<212> TYPE: DNA
<213> ORGANISM: Hepatitis C virus

<400> SEQUENCE: 241
tgcagagagt gctgatactg gcctc 25

<210> SEQ ID NO 242
<211> LENGTH: 27
<212> TYPE: DNA
<213> ORGANISM: Hepatitis C virus

<400> SEQUENCE: 242
tgcagagagt gctgatactg gcctctc 27

<210> SEQ ID NO 243
<211> LENGTH: 29
<212> TYPE: DNA
<213> ORGANISM: Hepatitis C virus

<400> SEQUENCE: 243
tgcagagagt gctgatactg gcctctctg 29

<210> SEQ ID NO 244
<211> LENGTH: 22
<212> TYPE: DNA
<213> ORGANISM: Hepatitis C virus

<400> SEQUENCE: 244
agagagtgct gatactggcc tc 22

<210> SEQ ID NO 245
<211> LENGTH: 24
<212> TYPE: DNA
<213> ORGANISM: Hepatitis C virus

<400> SEQUENCE: 245
agagagtgct gatactggcc tctc 24

<210> SEQ ID NO 246
<211> LENGTH: 26
<212> TYPE: DNA
<213> ORGANISM: Hepatitis C virus

<400> SEQUENCE: 246
agagagtgct gatactggcc tctctg 26

<210> SEQ ID NO 247
<211> LENGTH: 27
<212> TYPE: DNA
<213> ORGANISM: Hepatitis C virus

<400> SEQUENCE: 247
agagagtgct gatactggcc tctctgc 27

<210> SEQ ID NO 248
<211> LENGTH: 29
<212> TYPE: DNA
<213> ORGANISM: Hepatitis C virus

<400> SEQUENCE: 248
agagagtgct gatactggcc tctctgcag 29

<210> SEQ ID NO 249
<211> LENGTH: 22
<212> TYPE: DNA
<213> ORGANISM: Hepatitis C virus

<400> SEQUENCE: 249
agagtgctga tactggcctc tc 22

<210> SEQ ID NO 250
<211> LENGTH: 24
<212> TYPE: DNA
<213> ORGANISM: Hepatitis C virus

<400> SEQUENCE: 250
agagtgctga tactggcctc tctg 24

<210> SEQ ID NO 251
<211> LENGTH: 25
<212> TYPE: DNA
<213> ORGANISM: Hepatitis C virus

<400> SEQUENCE: 251
agagtgctga tactggcctc tctgc 25

<210> SEQ ID NO 252
<211> LENGTH: 27
<212> TYPE: DNA
<213> ORGANISM: Hepatitis C virus

<400> SEQUENCE: 252
agagtgctga tactggcctc tctgcag 27

<210> SEQ ID NO 253
<211> LENGTH: 22
<212> TYPE: DNA
<213> ORGANISM: Hepatitis C virus

<400> SEQUENCE: 253
agtgctgata ctggcctctc tg 22

<210> SEQ ID NO 254
<211> LENGTH: 23
<212> TYPE: DNA
<213> ORGANISM: Hepatitis C virus

<400> SEQUENCE: 254
agtgctgata ctggcctctc tgc 23

<210> SEQ ID NO 255
<211> LENGTH: 25
<212> TYPE: DNA
<213> ORGANISM: Hepatitis C virus

<400> SEQUENCE: 255
agtgctgata ctggcctctc tgcag 25

<210> SEQ ID NO 256
<211> LENGTH: 28
<212> TYPE: DNA
<213> ORGANISM: Hepatitis C virus

<400> SEQUENCE: 256
agtgctgata ctggcctctc tgcagatc 28

<210> SEQ ID NO 257
<211> LENGTH: 21
<212> TYPE: DNA
<213> ORGANISM: Hepatitis C virus

<400> SEQUENCE: 257
tgctgatact ggcctctctg c 21

<210> SEQ ID NO 258
<211> LENGTH: 23
<212> TYPE: DNA
<213> ORGANISM: Hepatitis C virus

<400> SEQUENCE: 258
tgctgatact ggcctctctg cag 23

<210> SEQ ID NO 259
<211> LENGTH: 26
<212> TYPE: DNA
<213> ORGANISM: Hepatitis C virus

<400> SEQUENCE: 259
tgctgatact ggcctctctg cagatc 26

<210> SEQ ID NO 260
<211> LENGTH: 29
<212> TYPE: DNA
<213> ORGANISM: Hepatitis C virus

<400> SEQUENCE: 260
tgctgatact ggcctctctg cagatcaag 29

<210> SEQ ID NO 261
<211> LENGTH: 23
<212> TYPE: DNA
<213> ORGANISM: Hepatitis C virus

<400> SEQUENCE: 261
tgatactggc ctctctgcag atc 23

<210> SEQ ID NO 262
<211> LENGTH: 26
<212> TYPE: DNA
<213> ORGANISM: Hepatitis C virus

<400> SEQUENCE: 262
tgatactggc ctctctgcag atcaag 26

<210> SEQ ID NO 263
<211> LENGTH: 21
<212> TYPE: DNA
<213> ORGANISM: Hepatitis C virus

<400> SEQUENCE: 263
atactggcct ctctgcagat c 21

<210> SEQ ID NO 264
<211> LENGTH: 24
<212> TYPE: DNA
<213> ORGANISM: Hepatitis C virus

<400> SEQUENCE: 264
atactggcct ctctgcagat caag 24

<210> SEQ ID NO 265
<211> LENGTH: 22
<212> TYPE: DNA
<213> ORGANISM: Hepatitis C virus

<400> SEQUENCE: 265
actggcctct ctgcagatca ag 22

<210> SEQ ID NO 266
<211> LENGTH: 3182
<212> TYPE: DNA
<213> ORGANISM: Hepatitis B virus -continued

<400> SEQUENCE: 266

```
aattccacaa ccttccacca aactctgcaa gatcccagag tgagaggcct gtatttccct     60
gctggtggct ccagttcagg aacagtaaac cctgttctga ctactgcctc tcccttatcg    120
tcaatcttct cgaggattgg ggaccctgcg ctgaacatgg agaacatcac atcaggattc    180
ctaggacccc ttctcgtgtt acaggcgggg tttttcttgt tgacaagaat cctcacaata    240
ccgcagagtc tagactcgtg gtggacttct ctcaattttc tagggggaac taccgtgtgt    300
cttggccaaa attcgcagtc cccaacctcc aatcactcac caacctcttg tcctccaact    360
tgtcctggtt atcgctggat gtgtctgcgg cgttttatca tcttcctctt catcctgctg    420
ctatgcctca tcttcttgtt ggttcttctg gactatcaag gtatgttgcc cgtttgtcct    480
ctaattccag gatcctcaac aaccagcacg ggaccatgcc ggacctgcat gactactgct    540
caaggaacct ctatgtatcc ctcctgttgc tgtaccaaac cttcggacgg aaattgcacc    600
tgtattccca tcccatcatc ctgggctttc ggaaaattcc tatgggagtg ggcctcagcc    660
cgtttctcct ggctcagttt actagtgcca tttgttcagt ggttcgtagg gctttccccc    720
actgtttggc tttcagttat atggatgatg tggtattggg ggccaagtct gtacagcatc    780
ttgagtccct ttttaccgct gttaccaatt ttcttttgtc tttgggtata catttaaacc    840
ctaacaaaac aaagagatgg ggttactctc taaattttat gggttatgtc attggatgtt    900
atgggtcctt gccacaagaa cacatcatac aaaaaatcaa agaatgtttt agaaaacttc    960
ctattaacag gcctattgat tggaaagtat gtcaacgaat tgtgggtctt ttgggttttg   1020
ctgccccttt tacacaatgt ggttatcctg cgttgatgcc tttgtatgca tgtattcaat   1080
ctaagcaggc tttcactttc tcgccaactt acaaggcctt tctgtgtaaa caatacctga   1140
acctttaccc cgttgcccgg caacggccag gtctgtgcca agtgtttgct gacgcaaccc   1200
ccactggctg gggcttggtc atgggccatc agcgcatgcg tggaaccttt tcggctcctc   1260
tgccgatcca tactgcggaa ctcctagccg cttgttttgc tcgcagcagg tctggagcaa   1320
acattatcgg gactgataac tctgttgtcc tatcccgcaa atatacatcg tttccatggc   1380
tgctaggctg tgctgccaac tggatcctgc gcgggacgtc ctttgtttac gtcccgtcgg   1440
cgctgaatcc tgcggacgac ccttctcggg gtcgcttggg actctctcgt ccccttctcc   1500
gtctgccgtt ccgaccgacc acggggcgca cctctcttta cgcggactcc ccgtctgtgc   1560
cttctcatct gccggaccgt gtgcacttcg cttcacctct gcacgtcgca tggagaccac   1620
cgtgaacgcc caccaaatat tgcccaaggt cttacataag aggactcttg gactctcagc   1680
aatgtcaacg accgaccttg aggcatactt caaagactgt ttgtttaaag actgggagga   1740
gttgggggag gagattaggt taaaggtctt tgtactagga ggctgtaggc ataaattggt   1800
ctgcgcacca gcaccatgca actttttcac ctctgcctaa tcatctcttg ttcatgtcct   1860
actgttcaag cctccaagct gtgccttggg tggctttggg gcatggacat cgacccttat   1920
aaagaatttg gagctactgt ggagttactc tcgtttttgc cttctgactt ctttccttca   1980
gtacgagatc ttctagatac cgcctcagct ctgtatcggg aagccttaga gtctcctgag   2040
cattgttcac ctcaccatac tgcactcagg caagcaattc tttgctgggg ggaactaatg   2100
actctagcta cctgggtggg tgttaatttg gaagatccag cgtctagaga cctagtagtc   2160
agttatgtca acactaatat gggcctaaag ttcaggcaac tcttgtggtt tcacatttct   2220
tgtctcactt ttggaagaga aacagttata gagtatttgg tgtctttcgg agtgtggatt   2280
cgcactcctc cagcttatag accaccaaat gcccctatcc tatcaacact tccggagact   2340
```

-continued

```
actgttgtta gacgacgagg caggtcccct agaagaagaa ctccctcgcc tcgcagacga   2400

aggtctcaat cgccgcgtcg cagaagatct caatctcggg aatctcaatg ttagtattcc   2460

ttggactcat aaggtgggga actttactgg gctttattct tctactgtac ctgtctttaa   2520

tcctcattgg aaaacaccat cttttcctaa tatacattta caccaagaca ttatcaaaaa   2580

atgtgaacag tttgtaggcc cactcacagt taatgagaaa agaagattgc aattgattat   2640

gcctgccagg ttttatccaa aggttaccaa atatttacca ttggataagg gtattaaacc   2700

ttattatcca gaacatctag ttaatcatta cttccaaact agacactatt tacacactct   2760

atggaaggcg ggtatattat ataagagaga aacaacacat agcgcctcat tttgtgggtc   2820

accatattct tgggaacaag atctacagca tggggcagaa tctttccacc agcaatcctc   2880

tgggattctt tcccgaccac cagttggatc cagccttcag agcaaacacc gcaaatccag   2940

attgggactt caatcccaac aaggacacct ggccagacgc caacaaggta ggagctggag   3000

cattcgggct gggtttcacc ccaccgcacg gaggcctttt ggggtggagc cctcaggctc   3060

agggcatact acaaactttg ccagcaaatc cgcctcctgc ctccaccaat cgccagtcag   3120

gaaggcagcc taccccgctg tctccacctt tgagaaacac tcatcctcag gccatgcagt   3180

gg                                                                  3182
```